(12) United States Patent
Lewis

(10) Patent No.: US 8,188,048 B2
(45) Date of Patent: May 29, 2012

(54) COMBINATION THERAPY

(75) Inventor: Richard James Lewis, Wooloongabba (AU)

(73) Assignee: Xenome Limited, Queensland (AU)

( * ) Notice: Subject to any disclaimer, the term of this patent is extended or adjusted under 35 U.S.C. 154(b) by 1376 days.

(21) Appl. No.: 11/821,525

(22) Filed: Jun. 22, 2007

(65) Prior Publication Data

US 2009/0105129 A1 Apr. 23, 2009

Related U.S. Application Data

(60) Provisional application No. 60/816,124, filed on Jun. 23, 2006.

(51) Int. Cl.
*A61K 38/04* (2006.01)
*A61K 38/10* (2006.01)

(52) U.S. Cl. ........ 514/18.3; 514/1.1; 514/21.5; 530/300

(58) Field of Classification Search .................. None
See application file for complete search history.

(56) References Cited

U.S. PATENT DOCUMENTS

| 6,767,896 B1 | 7/2004 | McIntosh et al. |
| 2005/0143560 A1 | 6/2005 | McIntosh et al. |

FOREIGN PATENT DOCUMENTS

| WO | WO 93/13128 | 7/1993 |
| WO | WO 97/01351 | 1/1997 |
| WO | WO 99/54350 | 10/1999 |
| WO | WO 00/15654 | 3/2000 |
| WO | WO 00/20444 | 4/2000 |
| WO | WO 00/44769 | 8/2000 |
| WO | WO 02/16317 A1 | 2/2002 |
| WO | WO 02/16318 A1 | 2/2002 |
| WO | WO 2004/050688 A1 | 6/2004 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Hassenbusch S, J. et al., "Polyanalgesic Consensus Conference 2003: An Update on the Management of Pain by Intraspinal Drug Delivery—Report of an Expert Panel", *J. Pain & Symptom Management 27*(6): 540-563 (2004).
Bohn L. M. et al., "Potentiated Opioid Analgesia in Norepinephrine Transporter Knock-Out Mice", *J. Neuroscience 20*(24): 9040-9045 (2000).
Nielsen C. K. et al., "Anti-allodynic efficacy of the χ-conopeptide, Xen2174, in rats with neuropathic pain", *Pain 118*: 112-124 (2005).
Obata H. et al., "Spinal noradrenaline transporter inhibition by reboxetine and Xen2174 reduces tactile hypersensitivity after surgery in rats", *Pain 113*: 271-276 (2005).
Smith M.T. et al., "Lack of Anti-Allodynic Cross-Tolerance Between Intrathecal XEN2174 and Morphine in the CCI-Rat Model of Neuropathic Pain", *Poster presented as part of the 11th World Congress on Pain*, Sydney, Australia., Aug. 21-26, 2005.
Smith M.T. et al., "Intrathecal XEN2174 Produces Significant Anti-Allodynia in Morphine-Tolerant Rates Using the CCI-Model of Persistent Neuropathic Pain", *Abstract, 11th World Congress on Pain*, Sydney, Australia., Aug. 21-26, 2005.

* cited by examiner

*Primary Examiner* — Christine J Saoud
*Assistant Examiner* — Jon M Lockard
(74) *Attorney, Agent, or Firm* — Scully, Scott, Murphy & Presser, P.C.

(57) ABSTRACT

The present invention relates generally to methods for inducing, promoting or otherwise facilitating pain relief. More particularly, the present invention relates to a synergistic combination of a selective inhibitor of the neuronal norepinephrine transporter and an analgesic agent in the therapeutic management of vertebrate animals, including humans, for producing analgesia or for the prevention or alleviation of pain.

24 Claims, 5 Drawing Sheets

(A) CCI-rats: combined dosing with i.t. SEQ ID NO: 6 (0.2 nmol) and i.t. Morphine (0.7 nmol)

(B) CCI-rats: combined dosing with i.t. SEQ ID NO: 6 (0.4 nmol) and i.t. Morphine (3.5 nmol)

(A) SEQ ID NO: 167 (0.18mcg/kg;$ED_{20}$) in CCI rats (B) SEQ ID NO: 167 (0.18 mcg/kg) + SEQ ID NO: 6 (0.4nmol)

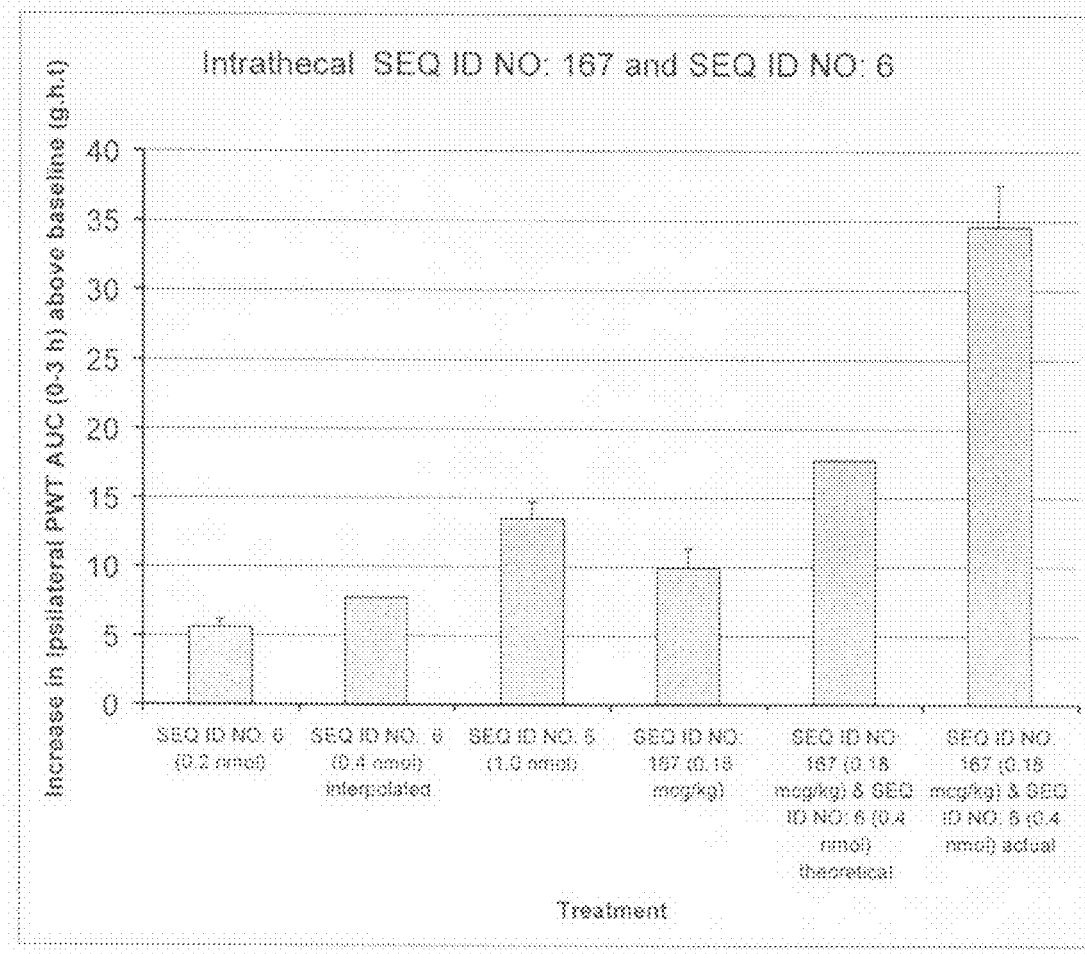

SEQUENCE LISTING

```
<160> NUMBER OF SEQ ID NOS: 168

<210> SEQ ID NO 1
<211> LENGTH: 13
<212> TYPE: PRT
<213> ORGANISM: conus marmoneus
<220> FEATURE:
<221> NAME/KEY: MISC_FEATURE
<222> LOCATION: (12)..(12)
<223> OTHER INFORMATION: Xaa is 4Hyp

<400> SEQUENCE: 1

Asn Gly Val Cys Cys Gly Tyr Lys Leu Cys His Xaa Cys
1               5                   10

<210> SEQ ID NO 2
<211> LENGTH: 13
<212> TYPE: PRT
<213> ORGANISM: conus marmoneus
<220> FEATURE:
<221> NAME/KEY: MISC_FEATURE
<222> LOCATION: (12)..(12)
<223> OTHER INFORMATION: Xaa is 4Hyp

<400> SEQUENCE: 2

Val Gly Val Cys Cys Gly Tyr Lys Leu Cys His Xaa Cys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (8)..(8)
<223> OTHER INFORMATION: Xaa is any amino acid residue except Cys, or
      such a sequence in which Gly, Tyr, Lys or Leu are subject to
      conservative amino acid substitution or side chain modification,
      or a salt, ester, amide, prodrug or cyclised derivative thereof
<220> FEATURE:
<221> NAME/KEY: MISC_FEATURE
<222> LOCATION: (9)..(9)
<223> OTHER INFORMATION: Xaa is any amino acid residue except Cys, or
      such a sequence in which  Gly, Tyr, Lys or Leu are subject to
      conservative amino acid substitution or side chain modification,
      or a salt, ester, amide, prodrug or cyclised derivative thereof

<400> SEQUENCE: 3

Cys Cys Gly Tyr Lys Leu Cys Xaa Xaa Cys
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: xaa is selected from Ala, Lys, Phe, Tyr, pGlu,
```

```
            Gln, Asp, Asn, Leu, Orn, Trp, hPhe and a deletion
<220> FEATURE:
<221> NAME/KEY: MISC_FEATURE
<222> LOCATION: (2)..(2)
<223> OTHER INFORMATION: Xaa is selected from Trp, DTrp, Tyr, Phe, hPhe,
      Ala, MeY, Arg, Ben, Nap, Orn, pGlu, DpGlu, Gln, Asp, Asn, Pro, Hyp
      and a deletion
<220> FEATURE:
<221> NAME/KEY: MISC_FEATURE
<222> LOCATION: (3)..(3)
<223> OTHER INFORMATION: Xaa is selected from Arg, Ala, Asn, Lys, Phe,
      BHK, Orn, DArg, Nle, DLys, DMK, DAsn, Thr, ABZ, Nap, Cit, Val,
      Tyr, Trp, pGlu, DpGlu, Gln, Thr, Glu, Asp and a deletion
<220> FEATURE:
<221> NAME/KEY: MISC_FEATURE
<222> LOCATION: (4)..(4)
<223> OTHER INFORMATION: Xaa is selected from Gly, Asp, Lys, Arg, Ala,
      Nle, Ser, Phe, Leu, Glu, Gla, Asn, Thr, g-Asn, g-Ser, g-Thr and a
      deletion
<220> FEATURE:
<221> NAME/KEY: MISC_FEATURE
<222> LOCATION: (5)..(5)
<223> OTHER INFORMATION: Xaa is selected from Val, Leu, Nle, Ile, Thr,
      Ala, Asn, Trp, Phe, Gly, Ser, Abu, g Asn, g-Ser and g-Thr
<220> FEATURE:
<221> NAME/KEY: MISC_FEATURE
<222> LOCATION: (9)..(9)
<223> OTHER INFORMATION: Xaa is selected from Tyr, MeY, Phe, m-Tyr,
      o-Tyr, norTyr, mono-halo-Tyr, di halo-Tyr, O-sulpho-Tyr,
      O-phospho-Tyr, nitro-Tyr, Trp, DTrp, neo-Trp, halo Trp (D and L),
      any non-natural aromatic amino acid, an aliphatic amino acid
      bearing
<220> FEATURE:
<221> NAME/KEY: MISC_FEATURE
<222> LOCATION: (10)..(10)
<223> OTHER INFORMATION: Xaa is selected from Lys, Arg, homoLys,
      homoArg, Orn, nor-Lys, His, N-methyl lysine, DMK, TMK, any
      non-natural basic amino acid, Ser, Thr, g-Ser, g-Thr and any
      non-natural hydroxylated amino acid
<220> FEATURE:
<221> NAME/KEY: MISC_FEATURE
<222> LOCATION: (11)..(11)
<223> OTHER INFORMATION: Xaa is selected from Leu, DLeu, Nle, Ile, Hle,
      Val, Ala, Met, Phe, Tyr, m-Tyr, o Tyr, norTyr, mono-halo-Tyr,
      di-halo-Tyr, O-sulpho-Tyr, O-phospho-Tyr, nitro Tyr, Trp, DTrp,
      neo-Trp, halo-Trp (D and L) and any non-natural aromatic amino
      acid
<220> FEATURE:
<221> NAME/KEY: MISC_FEATURE
<222> LOCATION: (13)..(13)
<223> OTHER INFORMATION: Xaa is any amino acid residue except Cys, or
      such a sequence in which Gly, Tyr, Lys or Leu are subject to
      conservative amino acid substitution or side chain modification,
      or a salt, ester, amide, prodrug or cyclised derivative thereof
<220> FEATURE:
<221> NAME/KEY: MISC_FEATURE
<222> LOCATION: (14)..(14)
<223> OTHER INFORMATION: Xaa is any amino acid residue except Cys, or
      such a sequence in which Gly, Tyr, Lys or Leu are subject to
      conservative amino acid substitution or side chain modification,
      or a salt, ester, amide, prodrug or cyclised derivative thereof
<220> FEATURE:
<221> NAME/KEY: MISC_FEATURE
<222> LOCATION: (16)..(16)
<223> OTHER INFORMATION: Xaa is selected from Gly, Ala, Lys, Arg,
      homoLys, homoArg, Orn, nor-Lys, His, N-methyl Lysine, DMK, TMK and
      any non natural basic amino acid or Xaa10 is a deletion

<400> SEQUENCE: 4

Xaa Xaa Xaa Xaa Xaa Cys Cys Gly Xaa Xaa Xaa Cys Xaa Xaa Cys Xaa
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic or recombinant peptide
```

```
<220> FEATURE:
<221> NAME/KEY: MISC_FEATURE
<222> LOCATION: (1)..(1)
<223> OTHER INFORMATION: Xaa is selected from Ala, Lys, Phe, Tyr, pGlu,
      Gln, Asp, Asn, Leu, Orn, Trp, hPhe and a deletion
<220> FEATURE:
<221> NAME/KEY: MISC_FEATURE
<222> LOCATION: (2)..(2)
<223> OTHER INFORMATION: Xaa is selected from Trp, DTrp, Tyr, Phe, hPhe,
      Ala, MeY, Arg, Ben, Nap, Orn, pGlu, DpGlu, Gln, Asp, Asn, Pro, Hyp
      and a deletion
<220> FEATURE:
<221> NAME/KEY: MISC_FEATURE
<222> LOCATION: (3)..(3)
<223> OTHER INFORMATION: Xaa is selected from Arg, Ala, Asn, Lys, Phe,
      BHK, Orn, DArg, Nle, DLys, DMK, DAsn, Thr, ABZ, Nap, Cit, Val,
      Tyr, Trp, pGlu, DpGlu, Gln, Thr, Glu, Asp and a deletion
<220> FEATURE:
<221> NAME/KEY: MISC_FEATURE
<222> LOCATION: (4)..(4)
<223> OTHER INFORMATION: Xaa is selected from Gly, Asp, Lys, Arg, Ala,
      Nle, Ser, Phe, Leu, Glu, Gla, Asn, Thr, g-Asn, g-Ser, g-Thr and a
      deletion
<220> FEATURE:
<221> NAME/KEY: MISC_FEATURE
<222> LOCATION: (5)..(5)
<223> OTHER INFORMATION: Xaa is selected from Gly, Asp, Lys, Arg, Ala,
      Nle, Ser, Phe, Leu, Glu, Gla, Asn, Thr, g-Asn, g-Ser, g-Thr and a
      deletion
<220> FEATURE:
<221> NAME/KEY: MISC_FEATURE
<222> LOCATION: (13)..(13)
<223> OTHER INFORMATION: xAA is any amino acid residue except Cys, or
      such a sequence in which Gly, Tyr, Lys or Leu are subject to
      conservative amino acid substitution or side chain modification,
      or a salt, ester, amide, prodrug or cyclised derivative thereof
<220> FEATURE:
<221> NAME/KEY: MISC_FEATURE
<222> LOCATION: (14)..(14)
<223> OTHER INFORMATION: Xaa is any amino acid residue except Cys, or
      such a sequence in which Gly, Tyr, Lys or Leu are subject to
      conservative amino acid substitution or side chain modification,
      or a salt, ester, amide, prodrug or cyclised derivative thereof

<400> SEQUENCE: 5

Xaa Xaa Xaa Xaa Xaa Cys Cys Gly Tyr Lys Leu Cys Xaa Xaa Cys
1               5                   10                  15

<210> SEQ ID NO 6
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is L-pyroglutamic acid
<220> FEATURE:
<221> NAME/KEY: MISC_FEATURE
<222> LOCATION: (12)..(12)
<223> OTHER INFORMATION: Xaa is 4Hyp

<400> SEQUENCE: 6

Xaa Gly Val Cys Cys Gly Tyr Lys Leu Cys His Xaa Cys
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (11)..(11)
```

<223> OTHER INFORMATION: Xaa is 4Hyp

<400> SEQUENCE: 7

Gly Val Cys Cys Gly Tyr Lys Leu Cys His Xaa Cys
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (11)..(11)
<223> OTHER INFORMATION: Xaa is 4Hyp

<400> SEQUENCE: 8

Gly Ile Cys Cys Gly Val Ser Phe Cys Tyr Xaa Cys
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (10)..(10)
<223> OTHER INFORMATION: Xaa is 4Hyp

<400> SEQUENCE: 9

Ala Cys Cys Gly Tyr Lys Leu Cys Ser Xaa Cys
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (11)..(11)
<223> OTHER INFORMATION: Xaa is 4Hyp

<400> SEQUENCE: 10

Gln Thr Cys Cys Gly Tyr Arg Met Cys Val Xaa Cys Gly
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (11)..(11)
<223> OTHER INFORMATION: Xaa is 4Hyp

<400> SEQUENCE: 11

Ser Thr Cys Cys Gly Phe Lys Met Cys Ile Xaa Cys
1               5                   10

<210> SEQ ID NO 12
<211> LENGTH: 11
<212> TYPE: PRT
<213> ORGANISM: Artificial Sequence

```
<220> FEATURE:
<223> OTHER INFORMATION: Synthetic or recombinant peptide
<220> FEATURE:
<221> NAME/KEY: MISC_FEATURE
<222> LOCATION: (10)..(10)
<223> OTHER INFORMATION: Xaa is 4Hyp

<400> SEQUENCE: 12

Val Cys Cys Gly Tyr Lys Leu Cys His Xaa Cys
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (11)..(11)
<223> OTHER INFORMATION: Xaa is 4Hyp

<400> SEQUENCE: 13

Gly Ile Cys Cys Gly Tyr Lys Leu Cys Tyr Xaa Cys
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (8)..(8)
<223> OTHER INFORMATION: Xaa is O-methyl-L-tyrosine
<220> FEATURE:
<221> NAME/KEY: MISC_FEATURE
<222> LOCATION: (13)..(13)
<223> OTHER INFORMATION: Xaa is 4Hyp

<400> SEQUENCE: 14

Tyr Arg Gly Leu Cys Cys Gly Xaa Lys Leu Cys Arg Xaa Cys
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (4)..(4)
<223> OTHER INFORMATION: Xaa is Nle
<220> FEATURE:
<221> NAME/KEY: MISC_FEATURE
<222> LOCATION: (8)..(8)
<223> OTHER INFORMATION: Xaa is O-methyl-L-tyrosine
<220> FEATURE:
<221> NAME/KEY: MISC_FEATURE
<222> LOCATION: (13)..(13)
<223> OTHER INFORMATION: xaa is 4Hyp

<400> SEQUENCE: 15

Tyr Arg Gly Xaa Cys Cys Gly Xaa Lys Leu Cys Arg Xaa Cys
1               5                   10

<210> SEQ ID NO 16
<211> LENGTH: 15
<212> TYPE: PRT
<213> ORGANISM: Artificial Sequence
```

-continued

```
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is Orn
<220> FEATURE:
<221> NAME/KEY: MISC_FEATURE
<222> LOCATION: (5)..(5)
<223> OTHER INFORMATION: Xaa is Nle
<220> FEATURE:
<221> NAME/KEY: MISC_FEATURE
<222> LOCATION: (9)..(9)
<223> OTHER INFORMATION: Xaa is O-methyl-L-tyrosine
<220> FEATURE:
<221> NAME/KEY: MIsc_Feature
<222> LOCATION: (14)..(14)
<223> OTHER INFORMATION: Xaa is 4Hyp

<400> SEQUENCE: 16

Xaa Tyr Arg Gly Xaa Cys Cys Gly Xaa Lys Leu Cys Arg Xaa Cys
1               5                   10                  15

<210> SEQ ID NO 17
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (8)..(8)
<223> OTHER INFORMATION: Xaa is O-methyl-L-tyrosine
<220> FEATURE:
<221> NAME/KEY: MISC_FEATURE
<222> LOCATION: (13)..(13)
<223> OTHER INFORMATION: Xaa is 4Hyp

<400> SEQUENCE: 17

Trp Arg Gly Leu Cys Cys Gly Xaa Lys Leu Cys His Xaa Cys
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is Orn
<220> FEATURE:
<221> NAME/KEY: MISC_FEATURE
<222> LOCATION: (4)..(4)
<223> OTHER INFORMATION: Xaa is Nle
<220> FEATURE:
<221> NAME/KEY: MISC_FEATURE
<222> LOCATION: (8)..(8)
<223> OTHER INFORMATION: Xaa is O-methyl-L-tyrosine
<220> FEATURE:
<221> NAME/KEY: MISC_FEATURE
<222> LOCATION: (13)..(13)
<223> OTHER INFORMATION: Xaa is 4Hyp

<400> SEQUENCE: 18

Xaa Arg Gly Xaa Cys Cys Gly Xaa Lys Leu Cys Arg Xaa Cys
1               5                   10

<210> SEQ ID NO 19
<211> LENGTH: 15
<212> TYPE: PRT
<213> ORGANISM: Artificial Sequence
<220> FEATURE:
```

<223> OTHER INFORMATION: Synthetic or recombinant peptide
<220> FEATURE:
<221> NAME/KEY: MISC_FEATURE
<222> LOCATION: (5)..(5)
<223> OTHER INFORMATION: Xaa is Nle
<220> FEATURE:
<221> NAME/KEY: MISC_FEATURE
<222> LOCATION: (9)..(9)
<223> OTHER INFORMATION: Xaa is O-methyl-L-tyrosine
<220> FEATURE:
<221> NAME/KEY: MISC_FEATURE
<222> LOCATION: (14)..(14)
<223> OTHER INFORMATION: Xaa is 4Hyp

<400> SEQUENCE: 19

Lys Tyr Arg Gly Xaa Cys Cys Gly Xaa Lys Leu Cys Arg Xaa Cys
1               5                   10                  15

<210> SEQ ID NO 20
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is L-beta-homolysine
<220> FEATURE:
<221> NAME/KEY: MISC_FEATURE
<222> LOCATION: (3)..(3)
<223> OTHER INFORMATION: Xaa is Nle
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: MISC_FEATURE
<222> LOCATION: (9)..(9)
<223> OTHER INFORMATION: Xaa is L-homoleucine
<220> FEATURE:
<221> NAME/KEY: MISC_FEATURE
<222> LOCATION: (12)..(12)
<223> OTHER INFORMATION: Xaa is 4Hyp

<400> SEQUENCE: 20

Xaa Gly Xaa Cys Cys Gly Xaa Lys Xaa Cys His Xaa Cys
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (8)..(8)
<223> OTHER INFORMATION: Xaa is O-methyl-L-tyrosine
<220> FEATURE:
<221> NAME/KEY: MISC_FEATURE
<222> LOCATION: (13)..(13)
<223> OTHER INFORMATION: Xaa is 4Hyp

<400> SEQUENCE: 21

Trp Arg Gly Val Cys Cys Gly Xaa Lys Leu Cys His Xaa Cys
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Synthetic or recombinant peptide

```
<220> FEATURE:
<221> NAME/KEY: MISC_FEATURE
<222> LOCATION: (8)..(8)
<223> OTHER INFORMATION: Xaa is O-methyl-L-tyrosine
<220> FEATURE:
<221> NAME/KEY: MISC_FEATURE
<222> LOCATION: (13)..(13)
<223> OTHER INFORMATION: Xaa is 4Hyp

<400> SEQUENCE: 22

Trp Lys Gly Val Cys Cys Gly Xaa Lys Leu Cys His Xaa Cys
1               5                   10

<210> SEQ ID NO 23
<211> LENGTH: 15
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (5)..(5)
<223> OTHER INFORMATION: Xaa is Nle
<220> FEATURE:
<221> NAME/KEY: MISC_FEATURE
<222> LOCATION: (9)..(9)
<223> OTHER INFORMATION: Xaa is O-methyl-L-tyrosine
<220> FEATURE:
<221> NAME/KEY: MISC_FEATURE
<222> LOCATION: (14)..(14)
<223> OTHER INFORMATION: Xaa is 4Hyp

<400> SEQUENCE: 23

Phe Arg Tyr Gly Xaa Cys Cys Gly Xaa Lys Leu Cys Arg Xaa Cys
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (2)..(2)
<223> OTHER INFORMATION: Xaa is Orn
<220> FEATURE:
<221> NAME/KEY: MISC_FEATURE
<222> LOCATION: (5)..(5)
<223> OTHER INFORMATION: Xaa is Nle
<220> FEATURE:
<221> NAME/KEY: MISC_FEATURE
<222> LOCATION: (9)..(9)
<223> OTHER INFORMATION: Xaa is O-methyl-L-tyrosine
<220> FEATURE:
<221> NAME/KEY: MISC_FEATURE
<222> LOCATION: (14)..(14)
<223> OTHER INFORMATION: Xaa is 4Hyp

<400> SEQUENCE: 24

Tyr Xaa Arg Gly Xaa Cys Cys Gly Xaa Lys Leu Cys Arg Xaa Cys
1               5                   10                  15

<210> SEQ ID NO 25
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is D-tryptophan
<220> FEATURE:
```

```
<221> NAME/KEY: MISC_FEATURE
<222> LOCATION: (8)..(8)
<223> OTHER INFORMATION: Xaa is O-methyl-L-tyrosine

<400> SEQUENCE: 25

Xaa Arg Gly Leu Cys Cys Gly Xaa Lys Leu Cys Arg Ala Cys
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (8)..(8)
<223> OTHER INFORMATION: Xaa is O-methyl-L-tyrosine
<220> FEATURE:
<221> NAME/KEY: MISC_FEATURE
<222> LOCATION: (13)..(13)
<223> OTHER INFORMATION: Xaa is 4Hyp

<400> SEQUENCE: 26

Trp Arg Gly Val Cys Cys Gly Xaa Lys Leu Cys His Xaa Cys
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (13)..(13)
<223> OTHER INFORMATION: Xaa is 4Hyp

<400> SEQUENCE: 27

Trp Arg Gly Leu Cys Cys Gly Tyr Lys Leu Cys His Xaa Cys
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is L-beta-homolysine
<220> FEATURE:
<221> NAME/KEY: MISC_FEATURE
<222> LOCATION: (3)..(3)
<223> OTHER INFORMATION: Xaa is Nle
<220> FEATURE:
<221> NAME/KEY: MISC_FEATURE
<222> LOCATION: (9)..(9)
<223> OTHER INFORMATION: Xaa is L-homoleucine
<220> FEATURE:
<221> NAME/KEY: MISC_FEATURE
<222> LOCATION: (12)..(12)
<223> OTHER INFORMATION: Xaa is 4Hyp

<400> SEQUENCE: 28

Xaa Gly Xaa Cys Cys Gly Tyr Lys Xaa Cys His Xaa Cys
1               5                   10

<210> SEQ ID NO 29
<211> LENGTH: 15
<212> TYPE: PRT
```

```
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (5)..(5)
<223> OTHER INFORMATION: Xaa is Nle
<220> FEATURE:
<221> NAME/KEY: MISC_FEATURE
<222> LOCATION: (9)..(9)
<223> OTHER INFORMATION: Xaa is O-methyl-L-tyrosine
<220> FEATURE:
<221> NAME/KEY: MISC_FEATURE
<222> LOCATION: (14)..(14)
<223> OTHER INFORMATION: Xaa is 4Hyp

<400> SEQUENCE: 29

Tyr Phe Arg Gly Xaa Cys Cys Gly Xaa Lys Leu Cys Arg Xaa Cys
1               5                   10                  15

<210> SEQ ID NO 30
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (8)..(8)
<223> OTHER INFORMATION: Xaa is O-methyl-L-tyrosine

<400> SEQUENCE: 30

Trp Arg Gly Val Cys Cys Gly Xaa Lys Leu Cys Arg Ala Cys
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (13)..(13)
<223> OTHER INFORMATION: Xaa is 4Hyp

<400> SEQUENCE: 31

Trp Arg Gly Val Cys Cys Gly Tyr Lys Leu Cys His Xaa Cys
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (7)..(7)
<223> OTHER INFORMATION: Xaa is O-methyl-L-tyrosine

<400> SEQUENCE: 32

Trp Gly Leu Cys Cys Gly Xaa Lys Leu Cys Arg Tyr Cys
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
```

```
<221> NAME/KEY: MISC_FEATURE
<222> LOCATION: (1)..(1)
<223> OTHER INFORMATION: L-beta-homolysine
<220> FEATURE:
<221> NAME/KEY: MISC_FEATURE
<222> LOCATION: (3)..(3)
<223> OTHER INFORMATION: Xaa is Nle
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: MISC_FEATURE
<222> LOCATION: (12)..(12)
<223> OTHER INFORMATION: Xaa is 4Hyp

<400> SEQUENCE: 33

Xaa Gly Xaa Cys Cys Gly Xaa Lys Leu Cys His Xaa Cys
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (13)..(13)
<223> OTHER INFORMATION: Xaa is 4Hyp

<400> SEQUENCE: 34

Trp Asn Gly Val Cys Cys Gly Tyr Lys Leu Cys His Xaa Cys
1               5                   10

<210> SEQ ID NO 35
<211> LENGTH: 15
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is acetyl
<220> FEATURE:
<221> NAME/KEY: MISC_FEATURE
<222> LOCATION: (9)..(9)
<223> OTHER INFORMATION: Xaa is O-methyl-L-tyrosine
<220> FEATURE:
<221> NAME/KEY: MISC_FEATURE
<222> LOCATION: (14)..(14)
<223> OTHER INFORMATION: Xaa is 4Hyp

<400> SEQUENCE: 35

Xaa Tyr Arg Gly Leu Cys Cys Gly Xaa Lys Leu Cys Arg Xaa Cys
1               5                   10                  15

<210> SEQ ID NO 36
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: MISC_FEATURE
<222> LOCATION: (12)..(12)
<223> OTHER INFORMATION: Xaa is 4Hyp

<400> SEQUENCE: 36
```

Trp Gly Leu Cys Cys Gly Xaa Lys Leu Cys Arg Xaa Cys
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (8)..(8)
<223> OTHER INFORMATION: Xaa is O-methyl-L-tyrosine

<400> SEQUENCE: 37

Trp Arg Gly Leu Cys Cys Gly Xaa Lys Leu Cys Arg Lys Cys
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (8)..(8)
<223> OTHER INFORMATION: Xaa is O-methyl-L-tyrosine

<400> SEQUENCE: 38

Trp Arg Gly Leu Cys Cys Gly Xaa Lys Leu Cys Arg Ala Cys
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Synthetic or recombinant peptide

<400> SEQUENCE: 39

Trp Arg Gly Val Cys Cys Gly Tyr Lys Leu Cys Arg Ala Cys
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (13)..(13)
<223> OTHER INFORMATION: Xaa is 4Hyp

<400> SEQUENCE: 40

Trp Asn Gly Val Cys Cys Gly Tyr Lys Leu Cys Arg Xaa Cys
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (8)..(8)
<223> OTHER INFORMATION: Xaa is O-methyl-L-tyrosine

```
<400> SEQUENCE: 41

Trp Arg Gly Val Cys Cys Gly Xaa Lys Leu Cys His Ala Cys
1               5                   10

<210> SEQ ID NO 42
<211> LENGTH: 15
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is L-pyroglutamic acid
<220> FEATURE:
<221> NAME/KEY: MISC_FEATURE
<222> LOCATION: (5)..(5)
<223> OTHER INFORMATION: Xaa is Nle
<220> FEATURE:
<221> NAME/KEY: MISC_FEATURE
<222> LOCATION: (9)..(9)
<223> OTHER INFORMATION: Xaa is O-methyl-L-tyrosine
<220> FEATURE:
<221> NAME/KEY: MISC_FEATURE
<222> LOCATION: (14)..(14)
<223> OTHER INFORMATION: Xaa is 4Hyp

<400> SEQUENCE: 42

Xaa Tyr Arg Gly Xaa Cys Cys Gly Xaa Lys Leu Cys Arg Xaa Cys
1               5                   10                  15

<210> SEQ ID NO 43
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is Orn
<220> FEATURE:
<221> NAME/KEY: MISC_FEATURE
<222> LOCATION: (3)..(3)
<223> OTHER INFORMATION: Xaa is Nle
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: MISC_FEATURE
<222> LOCATION: (9)..(9)
<223> OTHER INFORMATION: Xaa is L-homoleucine
<220> FEATURE:
<221> NAME/KEY: MISC_FEATURE
<222> LOCATION: (12)..(12)
<223> OTHER INFORMATION: Xaa is 4Hyp

<400> SEQUENCE: 43

Xaa Gly Xaa Cys Cys Gly Xaa Lys Xaa Cys His Xaa Cys
1               5                   10

<210> SEQ ID NO 44
<211> LENGTH: 15
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (13)..(13)
<223> OTHER INFORMATION: Xaa is 4Hyp

<400> SEQUENCE: 44
```

Trp Arg Gly Val Cys Cys Gly Tyr Lys Leu Cys His Xaa Cys Tyr
1               5                   10                  15

<210> SEQ ID NO 45
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: MISC_FEATURE
<222> LOCATION: (12)..(12)
<223> OTHER INFORMATION: Xaa is 4Hyp

<400> SEQUENCE: 45

Trp Gly Leu Cys Cys Gly Xaa Lys Leu Cys Arg Xaa Cys Tyr
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is Orn
<220> FEATURE:
<221> NAME/KEY: MISC_FEATURE
<222> LOCATION: (3)..(3)
<223> OTHER INFORMATION: Xaa is Nle
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: MISC_FEATURE
<222> LOCATION: (12)..(12)
<223> OTHER INFORMATION: Xaa is 4Hyp

<400> SEQUENCE: 46

Xaa Gly Xaa Cys Cys Gly Xaa Lys Leu Cys His Xaa Cys
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (8)..(8)
<223> OTHER INFORMATION: Xaa is O-methyl-L-tyrosine
<220> FEATURE:
<221> NAME/KEY: MISC_FEATURE
<222> LOCATION: (13)..(13)
<223> OTHER INFORMATION: Xaa is 4Hyp

<400> SEQUENCE: 47

Trp Asn Gly Val Cys Cys Gly Xaa Lys Leu Cys His Xaa Cys
1               5                   10

<210> SEQ ID NO 48
<211> LENGTH: 13
<212> TYPE: PRT
<213> ORGANISM: Artificial Sequence

```
<220> FEATURE:
<223> OTHER INFORMATION: Synthetic or recombinant peptide
<220> FEATURE:
<221> NAME/KEY: MISC_FEATURE
<222> LOCATION: (3)..(3)
<223> OTHER INFORMATION: Xaa is Nle
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: MISC_FEATURE
<222> LOCATION: (9)..(9)
<223> OTHER INFORMATION: Xaa is L-homoleucine
<220> FEATURE:
<221> NAME/KEY: MISC_FEATURE
<222> LOCATION: (12)..(12)
<223> OTHER INFORMATION: Xaa is 4Hyp

<400> SEQUENCE: 48

Asn Gly Xaa Cys Cys Gly Xaa Lys Xaa Cys His Xaa Cys
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is Orn
<220> FEATURE:
<221> NAME/KEY: MISC_FEATURE
<222> LOCATION: (3)..(3)
<223> OTHER INFORMATION: Xaa is Nle
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: MISC_FEATURE
<222> LOCATION: (9)..(9)
<223> OTHER INFORMATION: Xaa is Nle
<220> FEATURE:
<221> NAME/KEY: MISC_FEATURE
<222> LOCATION: (12)..(12)
<223> OTHER INFORMATION: Xaa is 4Hyp

<400> SEQUENCE: 49

Xaa Gly Xaa Cys Cys Gly Xaa Lys Xaa Cys His Xaa Cys
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is L-beta-homolysine
<220> FEATURE:
<221> NAME/KEY: MISC_FEATURE
<222> LOCATION: (9)..(9)
<223> OTHER INFORMATION: Xaa is L-homoleucine
<220> FEATURE:
<221> NAME/KEY: MISC_FEATURE
<222> LOCATION: (12)..(12)
<223> OTHER INFORMATION: Xaa is 4Hyp

<400> SEQUENCE: 50

Xaa Gly Val Cys Cys Gly Tyr Lys Xaa Cys His Xaa Cys
```

-continued

<210> SEQ ID NO 51
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (4)..(4)
<223> OTHER INFORMATION: Xaa is Nle

<400> SEQUENCE: 51

Tyr Asn Gly Xaa Cys Cys Gly Tyr Lys Leu Cys His Pro Cys
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is Orn
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: MISC_FEATURE
<222> LOCATION: (12)..(12)
<223> OTHER INFORMATION: Xaa is 4Hyp

<400> SEQUENCE: 52

Xaa Gly Leu Cys Cys Gly Xaa Lys Leu Cys His Xaa Cys
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is Orn
<220> FEATURE:
<221> NAME/KEY: MISC_FEATURE
<222> LOCATION: (3)..(3)
<223> OTHER INFORMATION: Xaa is Nle
<220> FEATURE:
<221> NAME/KEY: MISC_FEATURE
<222> LOCATION: (9)..(9)
<223> OTHER INFORMATION: Xaa is L-homoleucine
<220> FEATURE:
<221> NAME/KEY: MISC_FEATURE
<222> LOCATION: (12)..(12)
<223> OTHER INFORMATION: Xaa is 4Hyp

<400> SEQUENCE: 53

Xaa Gly Xaa Cys Cys Gly Tyr Lys Xaa Cys His Xaa Cys
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Synthetic or recombinant peptide

```
<220> FEATURE:
<221> NAME/KEY: MISC_FEATURE
<222> LOCATION: (8)..(8)
<223> OTHER INFORMATION: Xaa is O-methyl-L-tyrosine

<400> SEQUENCE: 54

Trp Asn Gly Val Cys Cys Gly Xaa Lys Leu Cys His Pro Cys
 1               5                  10

<210> SEQ ID NO 55
<211> LENGTH: 14
<212> TYPE: PRT
<213> ORGANISM: Artificial Sequence
<220> FEATURE:
<223> OTHER INFORMATION: Synthetic or recombinant peptide

<400> SEQUENCE: 55

Trp Arg Gly Val Cys Cys Gly Tyr Lys Leu Cys His Ala Cys
 1               5                  10

<210> SEQ ID NO 56
<211> LENGTH: 15
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (5)..(5)
<223> OTHER INFORMATION: Xaa is Nle
<220> FEATURE:
<221> NAME/KEY: MISC_FEATURE
<222> LOCATION: (9)..(9)
<223> OTHER INFORMATION: Xaa is O-methyl-L-tyrosine
<220> FEATURE:
<221> NAME/KEY: MISC_FEATURE
<222> LOCATION: (14)..(14)
<223> OTHER INFORMATION: Xaa is 4Hyp

<400> SEQUENCE: 56

Asp Tyr Arg Gly Xaa Cys Cys Gly Xaa Lys Leu Cys Arg Xaa Cys
 1               5                  10                  15

<210> SEQ ID NO 57
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (10)..(10)
<223> OTHER INFORMATION: Xaa is L-homoleucine

<400> SEQUENCE: 57

Tyr Asn Gly Val Cys Cys Gly Tyr Lys Xaa Cys His Pro Cys
 1               5                  10

<210> SEQ ID NO 58
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (3)..(3)
<223> OTHER INFORMATION: Xaa is Nle
<220> FEATURE:
<221> NAME/KEY: MISC_FEATURE
<222> LOCATION: (9)..(9)
<223> OTHER INFORMATION: Xaa is Nle
```

```
<220> FEATURE:
<221> NAME/KEY: MISC_FEATURE
<222> LOCATION: (12)..(12)
<223> OTHER INFORMATION: Xaa is 4Hyp

<400> SEQUENCE: 58

Asn Gly Xaa Cys Cys Gly Tyr Lys Xaa Cys His Xaa Cys
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is L-beta-homolysine
<220> FEATURE:
<221> NAME/KEY: MISC_FEATURE
<222> LOCATION: (3)..(3)
<223> OTHER INFORMATION: Xaa is Nle
<220> FEATURE:
<221> NAME/KEY: MISC_FEATURE
<222> LOCATION: (12)..(12)
<223> OTHER INFORMATION: Xaa is 4Hyp

<400> SEQUENCE: 59

Xaa Gly Xaa Cys Cys Gly Tyr Lys Leu Cys His Xaa Cys
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Synthetic or recombinant peptide

<400> SEQUENCE: 60

Asn Gly Val Cys Cys Gly Tyr Lys Leu Cys Trp Pro Cys
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Synthetic or recombinant peptide

<400> SEQUENCE: 61

Trp Asn Gly Val Cys Cys Gly Tyr Lys Leu Cys Arg Pro Cys
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (3)..(3)
<223> OTHER INFORMATION: Xaa is Nle
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: MISC_FEATURE
<222> LOCATION: (9)..(9)
<223> OTHER INFORMATION: Xaa is Nle
```

```
<220> FEATURE:
<221> NAME/KEY: MISC_FEATURE
<222> LOCATION: (12)..(12)
<223> OTHER INFORMATION: Xaa is 4Hyp

<400> SEQUENCE: 62

Asn Gly Xaa Cys Cys Gly Xaa Lys Xaa Cys His Xaa Cys
1               5                   10

<210> SEQ ID NO 63
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (8)..(8)
<223> OTHER INFORMATION: Xaa is O-methyl-L-tyrosine

<400> SEQUENCE: 63

Tyr Asn Gly Val Cys Cys Gly Xaa Lys Leu Cys Arg Ala Cys
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Synthetic or recombinant peptide

<400> SEQUENCE: 64

Asn Asp Val Cys Cys Gly Tyr Lys Leu Cys His Pro Cys
1               5                   10

<210> SEQ ID NO 65
<211> LENGTH: 14
<212> TYPE: PRT
<213> ORGANISM: Artificial Sequence
<220> FEATURE:
<223> OTHER INFORMATION: Synthetic or recombinant peptide

<400> SEQUENCE: 65

Trp Arg Gly Leu Cys Cys Gly Tyr Lys Leu Cys Arg Gly Cys
1               5                   10

<210> SEQ ID NO 66
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is L-pyroglutamic acid
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: MISC_FEATURE
<222> LOCATION: (12)..(12)
<223> OTHER INFORMATION: Xaa is 4Hyp

<400> SEQUENCE: 66

Xaa Gly Leu Cys Cys Gly Xaa Lys Leu Cys Arg Xaa Cys Tyr
1               5                   10

<210> SEQ ID NO 67
```

```
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is Orn
<220> FEATURE:
<221> NAME/KEY: MISC_FEATURE
<222> LOCATION: (3)..(3)
<223> OTHER INFORMATION: Xaa is Nle
<220> FEATURE:
<221> NAME/KEY: MISC_FEATURE
<222> LOCATION: (9)..(9)
<223> OTHER INFORMATION: Xaa is Nle
<220> FEATURE:
<221> NAME/KEY: MISC_FEATURE
<222> LOCATION: (12)..(12)
<223> OTHER INFORMATION: Xaa is 4Hyp

<400> SEQUENCE: 67

Xaa Gly Xaa Cys Cys Gly Tyr Lys Xaa Cys His Xaa Cys
 1               5                  10

<210> SEQ ID NO 68
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is L-homophenylalanine
<220> FEATURE:
<221> NAME/KEY: MISC_FEATURE
<222> LOCATION: (13)..(13)
<223> OTHER INFORMATION: Xaa is 4Hyp

<400> SEQUENCE: 68

Xaa Asn Gly Val Cys Cys Gly Tyr Lys Leu Cys His Xaa Cys
 1               5                  10

<210> SEQ ID NO 69
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (13)..(13)
<223> OTHER INFORMATION: Xaa is 4Hyp

<400> SEQUENCE: 69

Tyr Asn Gly Val Cys Cys Gly Tyr Lys Leu Cys Arg Xaa Cys
 1               5                  10

<210> SEQ ID NO 70
<211> LENGTH: 14
<212> TYPE: PRT
<213> ORGANISM: Artificial Sequence
<220> FEATURE:
<223> OTHER INFORMATION: Synthetic or recombinant peptide

<400> SEQUENCE: 70

Trp Asn Gly Val Cys Cys Gly Tyr Lys Leu Cys Arg Ala Cys
 1               5                  10

<210> SEQ ID NO 71
```

```
<211> LENGTH: 15
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (9)..(9)
<223> OTHER INFORMATION: Xaa is O-methyl-L-tyrosine

<400> SEQUENCE: 71

Phe Gly Gly Phe Trp Cys Cys Gly Xaa Lys Leu Cys Arg Ala Cys
1               5                   10                  15

<210> SEQ ID NO 72
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (13)..(13)
<223> OTHER INFORMATION: xaa is 4Hyp

<400> SEQUENCE: 72

Tyr Asn Gly Val Cys Cys Gly Tyr Lys Leu Cys Trp Xaa Cys
1               5                   10

<210> SEQ ID NO 73
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (13)..(13)
<223> OTHER INFORMATION: Xaa is 4Hyp

<400> SEQUENCE: 73

Trp Asn Gly Leu Cys Cys Gly Tyr Lys Leu Cys His Xaa Cys
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is L-beta-homolysine
<220> FEATURE:
<221> NAME/KEY: MISC_FEATURE
<222> LOCATION: (3)..(3)
<223> OTHER INFORMATION: Xaa is Nle

<400> SEQUENCE: 74

Xaa Gly Xaa Cys Cys Gly Tyr Lys Leu Cys His Pro Cys
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (3)..(3)
```

```
<223> OTHER INFORMATION: Xaa is Nle
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: MISC_FEATURE
<222> LOCATION: (12)..(12)
<223> OTHER INFORMATION: Xaa is 4Hyp

<400> SEQUENCE: 75

Asn Gly Xaa Cys Cys Gly Xaa Lys Leu Cys His Xaa Cys
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is L-beta-homolysine
<220> FEATURE:
<221> NAME/KEY: MISC_FEATURE
<222> LOCATION: (7)..(7)
<223> OTHER INFORMATION: Xaa is O-methyl-L-tyrosine

<400> SEQUENCE: 76

Xaa Gly Val Cys Cys Gly Xaa Lys Leu Cys His Pro Cys
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is L-beta-homolysine
<220> FEATURE:
<221> NAME/KEY: MISC_FEATURE
<222> LOCATION: (9)..(9)
<223> OTHER INFORMATION: Xaa is L-homoleucine

<400> SEQUENCE: 77

Xaa Gly Val Cys Cys Gly Tyr Lys Xaa Cys His Pro Cys
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is D-arginine
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: MISC_FEATURE
<222> LOCATION: (12)..(12)
<223> OTHER INFORMATION: Xaa is 4Hyp

<400> SEQUENCE: 78

Xaa Gly Val Cys Cys Gly Xaa Lys Leu Cys His Xaa Cys
```

```
<210> SEQ ID NO 79
<211> LENGTH: 14
<212> TYPE: PRT
<213> ORGANISM: Artificial Sequence
<220> FEATURE:
<223> OTHER INFORMATION: Synthetic or recombinant peptide

<400> SEQUENCE: 79

Trp Arg Gly Leu Cys Cys Gly Tyr Lys Leu Cys Arg Ala Cys
1               5                   10

<210> SEQ ID NO 80
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is L-beta-homolysine
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: MISC_FEATURE
<222> LOCATION: (12)..(12)
<223> OTHER INFORMATION: Xaa is 4Hyp

<400> SEQUENCE: 80

Xaa Gly Val Cys Cys Gly Xaa Lys Leu Cys His Xaa Cys
1               5                   10

<210> SEQ ID NO 81
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (3)..(3)
<223> OTHER INFORMATION: Xaa is Nle
<220> FEATURE:
<221> NAME/KEY: MISC_FEATURE
<222> LOCATION: (9)..(9)
<223> OTHER INFORMATION: Xaa is L-homoleucine
<220> FEATURE:
<221> NAME/KEY: MISC_FEATURE
<222> LOCATION: (12)..(12)
<223> OTHER INFORMATION: Xaa is 4Hyp

<400> SEQUENCE: 81

Asn Gly Xaa Cys Cys Gly Tyr Lys Xaa Cys His Xaa Cys
1               5                   10

<210> SEQ ID NO 82
<211> LENGTH: 14
<212> TYPE: PRT
<213> ORGANISM: Artificial Sequence
<220> FEATURE:
<223> OTHER INFORMATION: Synthetic or recombinant peptide

<400> SEQUENCE: 82

Tyr Asn Gly Val Cys Cys Gly Tyr Lys Leu Cys Arg Ala Cys
1               5                   10

<210> SEQ ID NO 83
```

```
<211> LENGTH: 14
<212> TYPE: PRT
<213> ORGANISM: Artificial Sequence
<220> FEATURE:
<223> OTHER INFORMATION: Synthetic or recombinant peptide

<400> SEQUENCE: 83

Trp Asn Gly Val Cys Cys Gly Tyr Lys Leu Cys His Pro Cys
1               5                   10

<210> SEQ ID NO 84
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (8)..(8)
<223> OTHER INFORMATION: Xaa is O-methyl-L-tyrosine

<400> SEQUENCE: 84

Phe Gly Gly Phe Cys Cys Gly Xaa Lys Leu Cys Arg Ala Cys
1               5                   10

<210> SEQ ID NO 85
<211> LENGTH: 14
<212> TYPE: PRT
<213> ORGANISM: Artificial Sequence
<220> FEATURE:
<223> OTHER INFORMATION: Synthetic or recombinant peptide

<400> SEQUENCE: 85

Tyr Asn Gly Val Cys Cys Gly Tyr Lys Leu Cys Arg Pro Cys
1               5                   10

<210> SEQ ID NO 86
<211> LENGTH: 14
<212> TYPE: PRT
<213> ORGANISM: Artificial Sequence
<220> FEATURE:
<223> OTHER INFORMATION: Synthetic or recombinant peptide

<400> SEQUENCE: 86

Trp Lys Asp Leu Cys Cys Gly Tyr Lys Leu Cys His Pro Cys
1               5                   10

<210> SEQ ID NO 87
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (8)..(8)
<223> OTHER INFORMATION: Xaa is O-methyl-L-tyrosine

<400> SEQUENCE: 87

Tyr Asn Gly Val Cys Cys Gly Xaa Lys Leu Cys His Pro Cys
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
```

```
<222> LOCATION: (1)..(1)
<223> OTHER INFORMATION: Xaa is L-beta-homolysine
<220> FEATURE:
<221> NAME/KEY: MISC_FEATURE
<222> LOCATION: (12)..(12)
<223> OTHER INFORMATION: Xaa is 4Hyp

<400> SEQUENCE: 88

Xaa Gly Val Cys Cys Gly Tyr Lys Leu Cys Arg Xaa Cys
1               5                   10

<210> SEQ ID NO 89
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (13)..(13)
<223> OTHER INFORMATION: Xaa is 4Hyp

<400> SEQUENCE: 89

Tyr Asn Gly Val Cys Cys Gly Tyr Lys Leu Cys His Xaa Cys
1               5                   10

<210> SEQ ID NO 90
<211> LENGTH: 14
<212> TYPE: PRT
<213> ORGANISM: Artificial Sequence
<220> FEATURE:
<223> OTHER INFORMATION: Synthetic or recombinant peptide

<400> SEQUENCE: 90

Tyr Asn Gly Val Cys Cys Gly Tyr Lys Leu Cys Arg Pro Cys
1               5                   10

<210> SEQ ID NO 91
<211> LENGTH: 14
<212> TYPE: PRT
<213> ORGANISM: Artificial Sequence
<220> FEATURE:
<223> OTHER INFORMATION: Synthetic or recombinant peptide

<400> SEQUENCE: 91

Trp Lys Asp Leu Cys Cys Gly Tyr Lys Leu Cys Trp Pro Cys
1               5                   10

<210> SEQ ID NO 92
<211> LENGTH: 14
<212> TYPE: PRT
<213> ORGANISM: Artificial Sequence
<220> FEATURE:
<223> OTHER INFORMATION: Synthetic or recombinant peptide

<400> SEQUENCE: 92

Tyr Asn Gly Val Cys Cys Gly Tyr Lys Leu Cys Trp Pro Cys
1               5                   10

<210> SEQ ID NO 93
<211> LENGTH: 14
<212> TYPE: PRT
<213> ORGANISM: Artificial Sequence
<220> FEATURE:
<223> OTHER INFORMATION: Synthetic or recombinant peptide

<400> SEQUENCE: 93

Trp Lys Asp Val Cys Cys Gly Tyr Lys Leu Cys Trp Pro Cys
1               5                   10
```

<210> SEQ ID NO 94
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is L-beta-homolysine

<400> SEQUENCE: 94

Xaa Gly Val Cys Cys Gly Tyr Lys Leu Cys His Pro Cys
1               5                   10

<210> SEQ ID NO 95
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (8)..(8)
<223> OTHER INFORMATION: Xaa is O-methyl-L-tyrosine

<400> SEQUENCE: 95

Tyr Asn Gly Val Cys Cys Gly Xaa Lys Leu Cys Pro Cys
1               5                   10

<210> SEQ ID NO 96
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (2)..(2)
<223> OTHER INFORMATION: Xaa is L-beta-homolysine
<220> FEATURE:
<221> NAME/KEY: MISC_FEATURE
<222> LOCATION: (13)..(13)
<223> OTHER INFORMATION: Xaa is 4Hyp

<400> SEQUENCE: 96

Trp Xaa Gly Val Cys Cys Gly Tyr Lys Leu Cys His Xaa Cys
1               5                   10

<210> SEQ ID NO 97
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is Orn
<220> FEATURE:
<221> NAME/KEY: MISC_FEATURE
<222> LOCATION: (3)..(3)
<223> OTHER INFORMATION: Xaa is Nle
<220> FEATURE:
<221> NAME/KEY: MISC_FEATURE
<222> LOCATION: (12)..(12)
<223> OTHER INFORMATION: Xaa is 4Hyp

<400> SEQUENCE: 97

Xaa Gly Xaa Cys Cys Gly Tyr Lys Leu Cys His Xaa Cys
1               5                   10

<210> SEQ ID NO 98
<211> LENGTH: 13
<212> TYPE: PRT
<213> ORGANISM: Artificial Sequence
<220> FEATURE:
<223> OTHER INFORMATION: Synthetic or recombinant peptide

<400> SEQUENCE: 98

Asn Gly Leu Cys Cys Gly Tyr Lys Leu Cys His Pro Cys
1               5                   10

<210> SEQ ID NO 99
<211> LENGTH: 13
<212> TYPE: PRT
<213> ORGANISM: Artificial Sequence
<220> FEATURE:
<223> OTHER INFORMATION: Synthetic or recombinant peptide

<400> SEQUENCE: 99

Arg Gly Val Cys Cys Gly Tyr Lys Leu Cys His Pro Cys
1               5                   10

<210> SEQ ID NO 100
<211> LENGTH: 13
<212> TYPE: PRT
<213> ORGANISM: Artificial Sequence
<220> FEATURE:
<223> OTHER INFORMATION: Synthetic or recombinant peptide

<400> SEQUENCE: 100

Gly Tyr Lys Leu Gly Cys Cys Gly Tyr Lys Leu Cys Cys
1               5                   10

<210> SEQ ID NO 101
<211> LENGTH: 16
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (15)..(15)
<223> OTHER INFORMATION: Xaa is 4Hyp

<400> SEQUENCE: 101

Trp Ala Ala Asn Gly Val Cys Cys Gly Tyr Lys Leu Cys His Xaa Cys
1               5                   10                  15

<210> SEQ ID NO 102
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is L-beta-homolysine
<220> FEATURE:
<221> NAME/KEY: MISC_FEATURE
<222> LOCATION: (12)..(12)
<223> OTHER INFORMATION: Xaa is 4Hyp

<400> SEQUENCE: 102

Xaa Gly Val Cys Cys Gly Tyr Lys Leu Cys His Xaa Cys
1               5                   10

<210> SEQ ID NO 103

```
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (12)..(12)
<223> OTHER INFORMATION: Xaa is L-1,2,3,4-tetrahydroisoquinoline-3-
      carboxylic acid

<400> SEQUENCE: 103

Asn Gly Val Cys Cys Gly Tyr Lys Leu Cys His Xaa Cys
1               5                   10

<210> SEQ ID NO 104
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is D-arginine
<220> FEATURE:
<221> NAME/KEY: MISC_FEATURE
<222> LOCATION: (12)..(12)
<223> OTHER INFORMATION: Xaa is 4Hyp

<400> SEQUENCE: 104

Xaa Gly Val Cys Cys Gly Tyr Lys Leu Cys His Xaa Cys
1               5                   10

<210> SEQ ID NO 105
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is O-methyl-L-tyrosine

<400> SEQUENCE: 105

Xaa Asn Gly Val Cys Cys Gly Tyr Lys Leu Cys His Pro Cys
1               5                   10

<210> SEQ ID NO 106
<211> LENGTH: 17
<212> TYPE: PRT
<213> ORGANISM: Artificial Sequence
<220> FEATURE:
<223> OTHER INFORMATION: Synthetic or recombinant peptide

<400> SEQUENCE: 106

Gly Ile Leu Arg Asn Gly Val Cys Cys Gly Tyr Lys Leu Cys His Pro
1               5                   10                  15

Cys

<210> SEQ ID NO 107
<211> LENGTH: 15
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (14)..(14)
<223> OTHER INFORMATION: Xaa is 4Hyp
```

<400> SEQUENCE: 107

Trp Ala Asn Gly Val Cys Cys Gly Tyr Lys Leu Cys His Xaa Cys
1               5                   10                  15

<210> SEQ ID NO 108
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is Nle
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: MISC_FEATURE
<222> LOCATION: (12)..(12)
<223> OTHER INFORMATION: Xaa is 4Hyp

<400> SEQUENCE: 108

Xaa Gly Val Cys Cys Gly Xaa Lys Leu Cys His Xaa Cys
1               5                   10

<210> SEQ ID NO 109
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is Orn

<400> SEQUENCE: 109

Xaa Gly Val Cys Cys Gly Tyr Lys Leu Cys His Pro Cys
1               5                   10

<210> SEQ ID NO 110
<211> LENGTH: 15
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is acetyl
<220> FEATURE:
<221> NAME/KEY: MISC_FEATURE
<222> LOCATION: (3)..(3)
<223> OTHER INFORMATION: Xaa is L-beta-homolysine
<220> FEATURE:
<221> NAME/KEY: MISC_FEATURE
<222> LOCATION: (14)..(14)
<223> OTHER INFORMATION: Xaa is 4Hyp

<400> SEQUENCE: 110

Xaa Trp Xaa Gly Val Cys Cys Gly Tyr Lys Leu Cys His Xaa Cys
1               5                   10                  15

<210> SEQ ID NO 111
<211> LENGTH: 14
<212> TYPE: PRT
<213> ORGANISM: Artificial Sequence
<220> FEATURE:
<223> OTHER INFORMATION: Synthetic or recombinant peptide

```
<400> SEQUENCE: 111

Tyr Asn Lys Val Cys Cys Gly Tyr Lys Leu Cys His Pro Cys
1               5                   10

<210> SEQ ID NO 112
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is L-beta-homolysine
<220> FEATURE:
<221> NAME/KEY: MISC_FEATURE
<222> LOCATION: (12)..(12)
<223> OTHER INFORMATION: Xaa is L-1,2,3,4-tetrahydroisoquinoline-3-
      carboxylic acid

<400> SEQUENCE: 112

Xaa Gly Val Cys Cys Gly Tyr Lys Leu Cys His Xaa Cys
1               5                   10

<210> SEQ ID NO 113
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (3)..(3)
<223> OTHER INFORMATION: Xaa is Nle
<220> FEATURE:
<221> NAME/KEY: MISC_FEATURE
<222> LOCATION: (12)..(12)
<223> OTHER INFORMATION: Xaa is 4Hyp

<400> SEQUENCE: 113

Asn Gly Xaa Cys Cys Gly Tyr Lys Leu Cys His Xaa Cys
1               5                   10

<210> SEQ ID NO 114
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (7)..(7)
<223> OTHER INFORMATION: Xaa is O-methyl-L-tyrosine

<400> SEQUENCE: 114

Asn Gly Val Cys Cys Gly Xaa Lys Leu Cys His Pro Cys
1               5                   10

<210> SEQ ID NO 115
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is acetyl
<220> FEATURE:
<221> NAME/KEY: MISC_FEATURE
<222> LOCATION: (2)..(2)
```

```
<223> OTHER INFORMATION: Xaa is L-beta-homolysine
<220> FEATURE:
<221> NAME/KEY: MISC_FEATURE
<222> LOCATION: (13)..(13)
<223> OTHER INFORMATION: Xaa is 4Hyp

<400> SEQUENCE: 115

Xaa Xaa Gly Val Cys Cys Gly Tyr Lys Leu Cys His Xaa Cys
1               5                   10

<210> SEQ ID NO 116
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (12)..(12)
<223> OTHER INFORMATION: Xaa is 4Hyp

<400> SEQUENCE: 116

Asn Gly Leu Cys Cys Gly Tyr Lys Leu Cys His Xaa Cys
1               5                   10

<210> SEQ ID NO 117
<211> LENGTH: 14
<212> TYPE: PRT
<213> ORGANISM: Artificial Sequence
<220> FEATURE:
<223> OTHER INFORMATION: Synthetic or recombinant peptide

<400> SEQUENCE: 117

Tyr Asn Gly Val Cys Cys Gly Tyr Lys Leu Cys His Pro Cys
1               5                   10

<210> SEQ ID NO 118
<211> LENGTH: 13
<212> TYPE: PRT
<213> ORGANISM: Artificial Sequence
<220> FEATURE:
<223> OTHER INFORMATION: Synthetic or recombinant peptide

<400> SEQUENCE: 118

Asn Gly Val Cys Cys Gly Tyr Lys Leu Cys His Lys Cys
1               5                   10

<210> SEQ ID NO 119
<211> LENGTH: 14
<212> TYPE: PRT
<213> ORGANISM: Artificial Sequence
<220> FEATURE:
<223> OTHER INFORMATION: Synthetic or recombinant peptide

<400> SEQUENCE: 119

Tyr Asn Arg Val Cys Cys Gly Tyr Lys Leu Cys His Pro Cys
1               5                   10

<210> SEQ ID NO 120
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is Nle
<220> FEATURE:
<221> NAME/KEY: MISC_FEATURE
```

```
<222> LOCATION: (12)..(12)
<223> OTHER INFORMATION: Xaa is 4Hyp

<400> SEQUENCE: 120

Xaa Gly Val Cys Cys Gly Tyr Lys Leu Cys His Xaa Cys
1               5                   10

<210> SEQ ID NO 121
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is benzoyl

<400> SEQUENCE: 121

Xaa Asn Gly Val Cys Cys Gly Tyr Lys Leu Cys His Pro Cys
1               5                   10

<210> SEQ ID NO 122
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is D-lysine
<220> FEATURE:
<221> NAME/KEY: MISC_FEATURE
<222> LOCATION: (12)..(12)
<223> OTHER INFORMATION: Xaa is 4Hyp

<400> SEQUENCE: 122

Xaa Gly Val Cys Cys Gly Tyr Lys Leu Cys His Xaa Cys
1               5                   10

<210> SEQ ID NO 123
<211> LENGTH: 13
<212> TYPE: PRT
<213> ORGANISM: Artificial Sequence
<220> FEATURE:
<223> OTHER INFORMATION: Synthetic or recombinant peptide

<400> SEQUENCE: 123

Asn Lys Val Cys Cys Gly Tyr Lys Leu Cys His Pro Cys
1               5                   10

<210> SEQ ID NO 124
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (7)..(7)
<223> OTHER INFORMATION: Xaa is O-methyl-L-tyrosine
<220> FEATURE:
<221> NAME/KEY: MISC_FEATURE
<222> LOCATION: (12)..(12)
<223> OTHER INFORMATION: Xaa is 4Hyp

<400> SEQUENCE: 124

Asn Gly Val Cys Cys Gly Xaa Lys Leu Cys His Xaa Cys
1               5                   10
```

-continued

```
<210> SEQ ID NO 125
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (12)..(12)
<223> OTHER INFORMATION: Xaa is 4Hyp

<400> SEQUENCE: 125

Asn Ala Val Cys Cys Gly Tyr Lys Leu Cys His Xaa Cys
1               5                   10

<210> SEQ ID NO 126
<211> LENGTH: 13
<212> TYPE: PRT
<213> ORGANISM: Artificial Sequence
<220> FEATURE:
<223> OTHER INFORMATION: Synthetic or recombinant peptide

<400> SEQUENCE: 126

Asn Gly Ile Cys Cys Gly Tyr Lys Leu Cys His Pro Cys
1               5                   10

<210> SEQ ID NO 127
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (9)..(9)
<223> OTHER INFORMATION: Xaa is Nle
<220> FEATURE:
<221> NAME/KEY: MISC_FEATURE
<222> LOCATION: (12)..(12)
<223> OTHER INFORMATION: Xaa is 4Hyp

<400> SEQUENCE: 127

Asn Gly Val Cys Cys Gly Tyr Lys Xaa Cys His Xaa Cys
1               5                   10

<210> SEQ ID NO 128
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is L-lysine (dimethyl)
<220> FEATURE:
<221> NAME/KEY: MISC_FEATURE
<222> LOCATION: (12)..(12)
<223> OTHER INFORMATION: Xaa is 4Hyp

<400> SEQUENCE: 128

Xaa Gly Val Cys Cys Gly Tyr Lys Leu Cys His Xaa Cys
1               5                   10

<210> SEQ ID NO 129
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
```

```
<221> NAME/KEY: MISC_FEATURE
<222> LOCATION: (1)..(1)
<223> OTHER INFORMATION: Xaa is D-asparagine
<220> FEATURE:
<221> NAME/KEY: MISC_FEATURE
<222> LOCATION: (12)..(12)
<223> OTHER INFORMATION: Xaa is 4Hyp

<400> SEQUENCE: 129

Xaa Gly Val Cys Cys Gly Tyr Lys Leu Cys His Xaa Cys
1               5                   10

<210> SEQ ID NO 130
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (12)..(12)
<223> OTHER INFORMATION: Xaa is L-pipecolic acid (homoproline)

<400> SEQUENCE: 130

Asn Gly Val Cys Cys Gly Tyr Lys Leu Cys His Xaa Cys
1               5                   10

<210> SEQ ID NO 131
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (12)..(12)
<223> OTHER INFORMATION: Xaa is 4Hyp

<400> SEQUENCE: 131

Ala Gly Val Cys Cys Gly Tyr Lys Leu Cys His Xaa Cys
1               5                   10

<210> SEQ ID NO 132
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is naphthyl

<400> SEQUENCE: 132

Xaa Asn Gly Val Cys Cys Gly Tyr Lys Leu Cys His Pro Cys
1               5                   10

<210> SEQ ID NO 133
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (3)..(3)
<223> OTHER INFORMATION: Xaa is Nle

<400> SEQUENCE: 133

Tyr Asn Xaa Val Cys Cys Gly Tyr Lys Leu Cys His Pro Cys
1               5                   10
```

```
<210> SEQ ID NO 134
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (12)..(12)
<223> OTHER INFORMATION: Xaa is 4Hyp

<400> SEQUENCE: 134

Phe Gly Val Cys Cys Gly Tyr Lys Leu Cys His Xaa Cys
1               5                   10

<210> SEQ ID NO 135
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (11)..(11)
<223> OTHER INFORMATION: Xaa is L-naphthylalanine

<400> SEQUENCE: 135

Asn Gly Val Cys Cys Gly Tyr Lys Leu Cys Xaa Pro Cys
1               5                   10

<210> SEQ ID NO 136
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (12)..(12)
<223> OTHER INFORMATION: Xaa is 4Hyp

<400> SEQUENCE: 136

Thr Gly Val Cys Cys Gly Tyr Lys Leu Cys His Xaa Cys
1               5                   10

<210> SEQ ID NO 137
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is 2-aminobenzoyl (anthraniloyl)
<220> FEATURE:
<221> NAME/KEY: MISC_FEATURE
<222> LOCATION: (12)..(12)
<223> OTHER INFORMATION: Xaa is 4Hyp

<400> SEQUENCE: 137

Xaa Gly Val Cys Cys Gly Tyr Lys Leu Cys His Xaa Cys
1               5                   10

<210> SEQ ID NO 138
<211> LENGTH: 13
<212> TYPE: PRT
<213> ORGANISM: Artificial Sequence
<220> FEATURE:
<223> OTHER INFORMATION: Synthetic or recombinant peptide
```

```
<220> FEATURE:
<221> NAME/KEY: MISC_FEATURE
<222> LOCATION: (1)..(1)
<223> OTHER INFORMATION: Xaa is naphthyl

<400> SEQUENCE: 138

Xaa Gly Val Cys Cys Gly Tyr Lys Leu Cys His Pro Cys
1               5                   10

<210> SEQ ID NO 139
<211> LENGTH: 13
<212> TYPE: PRT
<213> ORGANISM: Artificial Sequence
<220> FEATURE:
<223> OTHER INFORMATION: Synthetic or recombinant peptide

<400> SEQUENCE: 139

Asn Gly Thr Cys Cys Gly Tyr Lys Leu Cys His Pro Cys
1               5                   10

<210> SEQ ID NO 140
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is L-citrulline
<220> FEATURE:
<221> NAME/KEY: MISC_FEATURE
<222> LOCATION: (12)..(12)
<223> OTHER INFORMATION: Xaa is 4Hyp

<400> SEQUENCE: 140

Xaa Gly Val Cys Cys Gly Tyr Lys Leu Cys His Xaa Cys
1               5                   10

<210> SEQ ID NO 141
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is L-pyroglutamic acid
<220> FEATURE:
<221> NAME/KEY: MISC_FEATURE
<222> LOCATION: (8)..(8)
<223> OTHER INFORMATION: Xaa is O-methyl-L-tyrosine
<220> FEATURE:
<221> NAME/KEY: MISC_FEATURE
<222> LOCATION: (13)..(13)
<223> OTHER INFORMATION: Xaa is 4Hyp

<400> SEQUENCE: 141

Xaa Asn Gly Val Cys Cys Gly Xaa Lys Leu Cys His Xaa Cys
1               5                   10

<210> SEQ ID NO 142
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (12)..(12)
<223> OTHER INFORMATION: Xaa is O-methyl-L-tyrosine
```

<400> SEQUENCE: 142

Asn Gly Val Cys Cys Gly Tyr Lys Leu Cys His Xaa Cys
1               5                   10

<210> SEQ ID NO 143
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (12)..(12)
<223> OTHER INFORMATION: Xaa is 4Hyp

<400> SEQUENCE: 143

Pro Gly Val Cys Cys Gly Tyr Lys Leu Cys His Xaa Cys
1               5                   10

<210> SEQ ID NO 144
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is acetyl
<220> FEATURE:
<221> NAME/KEY: MISC_FEATURE
<222> LOCATION: (13)..(13)
<223> OTHER INFORMATION: Xaa is 4Hyp

<400> SEQUENCE: 144

Xaa Asn Gly Val Cys Cys Gly Tyr Lys Leu Cys His Xaa Cys
1               5                   10

<210> SEQ ID NO 145
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is D-pyroglutamic acid
<220> FEATURE:
<221> NAME/KEY: MISC_FEATURE
<222> LOCATION: (12)..(12)
<223> OTHER INFORMATION: Xaa is 4Hyp

<400> SEQUENCE: 145

Xaa Gly Val Cys Cys Gly Tyr Lys Leu Cys His Xaa Cys
1               5                   10

<210> SEQ ID NO 146
<211> LENGTH: 13
<212> TYPE: PRT
<213> ORGANISM: Artificial Sequence
<220> FEATURE:
<223> OTHER INFORMATION: Synthetic or recombinant peptide

<400> SEQUENCE: 146

Asn Gly Val Cys Cys Gly Tyr Lys Leu Cys His Ala Cys
1               5                   10

<210> SEQ ID NO 147

```
<211> LENGTH: 13
<212> TYPE: PRT
<213> ORGANISM: Artificial Sequence
<220> FEATURE:
<223> OTHER INFORMATION: Synthetic or recombinant peptide

<400> SEQUENCE: 147

Asn Gly Val Cys Cys Gly Tyr Lys Leu Cys His Pro Cys
1               5                   10

<210> SEQ ID NO 148
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (12)..(12)
<223> OTHER INFORMATION: Xaa is 4Hyp

<400> SEQUENCE: 148

Asp Gly Val Cys Cys Gly Tyr Lys Leu Cys His Xaa Cys
1               5                   10

<210> SEQ ID NO 149
<211> LENGTH: 9
<212> TYPE: PRT
<213> ORGANISM: Artificial Sequence
<220> FEATURE:
<223> OTHER INFORMATION: Synthetic or recombinant peptide

<400> SEQUENCE: 149

Val Cys Cys Gly Tyr Lys Leu Cys Cys
1               5

<210> SEQ ID NO 150
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (12)..(12)
<223> OTHER INFORMATION: Xaa is L-dimethyldopa or L-dimethoxy-
      phenylalanine

<400> SEQUENCE: 150

Asn Gly Val Cys Cys Gly Tyr Lys Leu Cys His Xaa Cys
1               5                   10

<210> SEQ ID NO 151
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (12)..(12)
<223> OTHER INFORMATION: Xaa is 4Hyp

<400> SEQUENCE: 151

Asn Gly Ala Cys Cys Gly Tyr Lys Leu Cys His Xaa Cys
1               5                   10

<210> SEQ ID NO 152
<211> LENGTH: 13
<212> TYPE: PRT
```

-continued

```
<213> ORGANISM: Artificial Sequence
<220> FEATURE:
<223> OTHER INFORMATION: Synthetic or recombinant peptide

<400> SEQUENCE: 152

Asp Gly Val Cys Cys Gly Tyr Lys Leu Cys His Pro Cys
1               5                   10

<210> SEQ ID NO 153
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is acetyl

<400> SEQUENCE: 153

Xaa Asn Gly Val Cys Cys Gly Tyr Lys Leu Cys His Pro Cys
1               5                   10

<210> SEQ ID NO 154
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (12)..(12)
<223> OTHER INFORMATION: Xaa is 4Hyp

<400> SEQUENCE: 154

Asn Gly Ala Cys Cys Gly Tyr Lys Leu Cys His Xaa Cys
1               5                   10

<210> SEQ ID NO 155
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is L-pyroglutamic acid
<220> FEATURE:
<221> NAME/KEY: MISC_FEATURE
<222> LOCATION: (12)..(12)
<223> OTHER INFORMATION: Xaa is 4Hyp

<400> SEQUENCE: 155

Xaa Asp Val Cys Cys Gly Tyr Lys Leu Cys His Xaa Cys
1               5                   10

<210> SEQ ID NO 156
<211> LENGTH: 13
<212> TYPE: PRT
<213> ORGANISM: Artificial Sequence
<220> FEATURE:
<223> OTHER INFORMATION: Synthetic or recombinant peptide

<400> SEQUENCE: 156

Asn Gly Val Cys Cys Gly Tyr Lys Leu Cys His Phe Cys
1               5                   10

<210> SEQ ID NO 157
<211> LENGTH: 13
```

```
<212> TYPE: PRT
<213> ORGANISM: Artificial Sequence
<220> FEATURE:
<223> OTHER INFORMATION: Synthetic or recombinant peptide

<400> SEQUENCE: 157

Asn Ser Val Cys Cys Gly Tyr Lys Leu Cys His Pro Cys
1               5                   10

<210> SEQ ID NO 158
<211> LENGTH: 14
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is L-pyroglutamic acid
<220> FEATURE:
<221> NAME/KEY: MISC_FEATURE
<222> LOCATION: (13)..(13)
<223> OTHER INFORMATION: Xaa is 4Hyp

<400> SEQUENCE: 158

Xaa Asn Gly Val Cys Cys Gly Tyr Lys Leu Cys His Xaa Cys
1               5                   10

<210> SEQ ID NO 159
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (12)..(12)
<223> OTHER INFORMATION: Xaa is L-thiazolidine-4-carboxylic acid

<400> SEQUENCE: 159

Asn Gly Val Cys Cys Gly Tyr Lys Leu Cys His Xaa Cys
1               5                   10

<210> SEQ ID NO 160
<211> LENGTH: 13
<212> TYPE: PRT
<213> ORGANISM: Artificial Sequence
<220> FEATURE:
<223> OTHER INFORMATION: Synthetic or recombinant peptide

<400> SEQUENCE: 160

Asn Gly Val Cys Cys Gly Tyr Lys Leu Cys His Glu Cys
1               5                   10

<210> SEQ ID NO 161
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (3)..(3)
<223> OTHER INFORMATION: Xaa is Abu
<220> FEATURE:
<221> NAME/KEY: MISC_FEATURE
<222> LOCATION: (12)..(12)
<223> OTHER INFORMATION: Xaa is 4Hyp

<400> SEQUENCE: 161

Asn Gly Xaa Cys Cys Gly Tyr Lys Leu Cys His Xaa Cys
```

-continued

<210> SEQ ID NO 162
<211> LENGTH: 15
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is acetyl

<400> SEQUENCE: 162

Xaa Tyr Asn Gly Val Cys Cys Gly Tyr Lys Leu Cys His Pro Cys
1               5                   10                  15

<210> SEQ ID NO 163
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (12)..(12)
<223> OTHER INFORMATION: Xaa is Nle

<400> SEQUENCE: 163

Asn Gly Val Cys Cys Gly Tyr Lys Leu Cys His Xaa Cys
1               5                   10

<210> SEQ ID NO 164
<211> LENGTH: 14
<212> TYPE: PRT
<213> ORGANISM: Artificial Sequence
<220> FEATURE:
<223> OTHER INFORMATION: Synthetic or recombinant peptide

<400> SEQUENCE: 164

Tyr Asn Gly Val Cys Cys Gly Tyr Lys Leu Cys Gln Pro Cys
1               5                   10

<210> SEQ ID NO 165
<211> LENGTH: 13
<212> TYPE: PRT
<213> ORGANISM: Artificial Sequence
<220> FEATURE:
<223> OTHER INFORMATION: Synthetic or recombinant peptide
<220> FEATURE:
<221> NAME/KEY: MISC_FEATURE
<222> LOCATION: (1)..(1)
<223> OTHER INFORMATION: Xaa is D-pyroglutamic acid
<220> FEATURE:
<221> NAME/KEY: MISC_FEATURE
<222> LOCATION: (12)..(12)
<223> OTHER INFORMATION: Xaa is 4Hyp

<400> SEQUENCE: 165

Xaa Gly Val Cys Cys Gly Tyr Lys Leu Cys His Xaa Cys
1               5                   10

<210> SEQ ID NO 166
<211> LENGTH: 13
<212> TYPE: PRT
<213> ORGANISM: Artificial Sequence
<220> FEATURE:
<223> OTHER INFORMATION: Synthetic or recombinant peptide

<400> SEQUENCE: 166

```
Asn Gly Val Cys Cys Gly Tyr Lys Leu Cys His Tyr Cys
1               5                   10

<210> SEQ ID NO 167
<211> LENGTH: 27
<212> TYPE: PRT
<213> ORGANISM: Artificial Sequence
<220> FEATURE:
<223> OTHER INFORMATION: Synthetic or recombinant peptide

<400> SEQUENCE: 167

Cys Lys Ser Lys Gly Ala Lys Cys Ser Lys Leu Met Tyr Asp Cys Cys
1               5                   10                  15

Ser Gly Ser Cys Ser Gly Thr Val Gly Arg Cys
            20                  25

<210> SEQ ID NO 168
<211> LENGTH: 25
<212> TYPE: PRT
<213> ORGANISM: Artificial Sequence
<220> FEATURE:
<223> OTHER INFORMATION: Synthetic or recombinant peptide

<400> SEQUENCE: 168

Cys Lys Ser Lys Gly Ala Lys Cys Ser Arg Leu Met Tyr Asp Cys Cys
1               5                   10                  15

Ser Gly Ser Cys Arg Ser Gly Lys Cys
            20                  25
```

COMBINATION THERAPY

CROSS REFERENCE TO RELATED APPLICATION

This application claims priority from U.S. Provisional Application No. 60/816,124, filed on Jun. 23, 2006.

The present invention relates generally to methods for inducing, promoting or otherwise facilitating pain relief. More particularly, the present invention relates to a synergistic combination of a selective inhibitor of the neuronal norepinephrine transporter and an analgesic agent in the therapeutic management of vertebrate animals, including humans, for the prevention or alleviation of pain, particularly moderate to severe pain.

Pain management is complex and often unsatisfactory. Many analgesic agents have side effects that cause other medical problems, particularly with long term use. Among the analgesic agents available, opioid analgesics are considered the most effective class of drugs available for the management of pain. Morphine is the 'gold standard' strong opioid analgesic with which all new opioid analgesic compounds are compared. Morphine is also recommended by the World Health Organisation as the drug of choice for the relief of moderate to severe cancer pain, the alleviation of moderate to severe pain in the post-surgical setting and for the relief of pain following trauma and cardiac infarction.

However, the opioid analgesics, including morphine, are well documented to produce a range of unwanted side effects. Severe side effects include allergic reactions, such as difficulty breathing, swelling of lips, tongue, face and/or throat and hives; respiratory depression; seizures; cold, clammy skin; severe weakness, severe dizziness; and unconsciousness. Other side effects include sedation, nausea, vomiting, dry mouth, loss of appetite, constipation, dizziness, tiredness, lightheadedness, muscle twitching, sweating, pruritis, urinary retention and loss of libido. Furthermore, long term use of opioid analgesics can result in tolerance where increasing amounts of opioid analgesics are required to provide a constant level of pain relief. Some opioid analgesics, such as morphine, may upon moderate or long term use, also result in patient dependency. In some patients, such as the chronically ill, the opioid side-effects render it impossible to continuously administer sufficiently high doses to adequately control pain. Some pain conditions do not sufficiently respond to opioid pain treatment alone.

A further problem with opiates is the identification of a causal relationship between intrathecal morphine sulfate infusion and the formation of catheter-tip inflammatory masses sufficient to cause pronounced motor deficits (Hassenbusch et al., 2004 J. Pain & Symptom Management 27(6), 540-563). The Polyanalgesic Consensus Conference for Intraspinal Therapy (Hassenbusch et al., 2004) has developed 6 Lines of therapy, many which involve combinations amongst different classes of analgesics to provide best treatment regimes. Opiates represent the first line therapy, with progressions to opiate combinations with local anaesthetics or opiates and adrenergic agonists in Line 2 regimen and other combinations in later Line regimens when intolerable side-effects occur or when analgesia becomes inadequate. As a consequence, there is a need for improved analgesic combinations with increased analgesic activity which comprise opioid and non-opioid analgesically active agents which offer the possibility of reducing the opioid side effects that might result from the otherwise required higher dosages.

Other classes of analgesics include non-steroidal anti-inflammatory drugs (NSAIDs), Selective cyclooxygenase-2 (COX-2) inhibitors, COX-3 inhibitors, anti-convulsants, GABA-B receptor agonists, alpha-2 adrenoreceptor agonists, tricyclic antidepressants, NMDA receptor antagonists, N-type Calcium Channel blockers, Sodium Channel Blockers, corticosteroids, Cannabinoids, Vanilloid receptor agonists, sedative drugs, psychostimulants, neurotensin agonists and selective serotonin reuptake inhibitors. Examples of each of these classes can be found, for example, in Enna and Bylund, xPharm: The Comprehensive Pharmacology Reference (Elsevier Inc, 2008) Adverse effects for members of each of these classes are also common and include, as examples the following: dyspepsia, abdominal pain, diarrhea, flatulence, gastrointestinal bleeding, renal toxicity, hepatotoxicity, and cutaneous hypersensitivity reactions (Cox-2 inhibitors), sedation, nystagmus, dizziness (gabapentin), psychedelic effects, emergence reactions, rise in arterial systolic pressure (NMDA receptor antagonists); drowsiness, fatigue, muscular hypotonia (rare), hypotension, apnea, blood dyscrasias, and thrombocytopenia (GABA receptor agonists); and inhibition of platelet aggregation, gastrointestinal reactions, dizziness, tinnitus, deafness, sweating, nausea and vomiting, headache, and mental confusion (NSAIDs). Therefore, there is a continuing need to identify new treatment regimens for pain that produce less side-effects and improved pain relief.

Inhibitors of neuronal amine neurotransmitter re-uptake are also known to have some analgesic effects. Chi (X)-conotoxin peptides isolated from marine snails of the genus *Conus* (cone snails) first described in WO 00/20444 have been found to be selective inhibitors of norepinephrine transporters, and have potent analgesic effects. Other members of this class were later identified in WO 00/44769 and US2005/0143560. In particular MrIA (WO 00/20444) and derivatives of MrIA have exhibited potent analgesic effects in animal models of pain. Importantly, these molecules have shown animal efficacy in some forms of hard to treat pain including post-surgical pain, neuropathic pain such as allodynia and inflammatory pain. Exemplary members of this class display greater analgesic potency than morphine, and a longer duration of action in mammals (WO 00/44769).

The present invention is predicated in part on the determination that selective inhibitors of the neuronal norepinephrine transporter synergise with the analgesic activity of other agents such as opioids. It has been shown that $\chi$-conotoxins and their derivatives can increase the pain relieving potency of analgesic agents, such as the opioid analgesics, and/or the duration of analgesia achieved by the analgesic agent. The increased pain relieving potency and/or duration of analgesia achieved by the combination allows a reduction in the amount of analgesic agent required to provide pain relief or allows a given amount of analgesic agent to provide longer lasting pain relief. In some cases, the amount of analgesic agent required may be reduced to a level considered sub-analgesic in the absence of the selective inhibitor of the neuronal norepinephrine transporter. In other cases, because of the longer duration of analgesia or pain relief, there is a reduction in the total amount of analgesic agent administered over the course of pain relief therapy.

In one aspect of the invention there is provided a method of producing analgesia in a subject comprising administering a synergistic combination of an effective amount of a selective inhibitor of the neuronal norepinephrine transporter and an effective amount of an analgesic agent.

In another aspect of the invention there is provided a method for the treatment or control of pain comprising administering a synergistic combination of an effective amount of a selective inhibitor of the neuronal norepinephrine transporter and an effective amount of an analgesic agent.

As used herein the term "combination" refers to the administration of the selective inhibitor of the neuronal norepinephrine transporter and an analgesic agent so that both compounds are, at least in part, simultaneously bioactive. Preferably, the inhibitor and the analgesic agent are administered so that the onset of their bioactivity occurs at about the same time. The selective inhibitor of the neuronal norepinephrine transporter and the analgesic agent may be administered in a single composition or may be administered in separate compositions simultaneously or sequentially.

As used herein the term "synergistic" when used in relation to the combination refers to a combination that allows a lower amount of analgesic agent and preferably also a lower amount of selective inhibitor of the neuronal norepinephrine transporter, than would be required to achieve a given level of analgesia or pain relief if the selective inhibitor of the neuronal norepinephrine transporter or the analgesic agent were administered alone. The synergistic combination may allow a lower amount of analgesic agent and/or selective inhibitor of neuronal norepinephrine transporter to be administered in a single dose to provide a given level of analgesia or pain relief than if the selective inhibitor of neuronal norepinephrine transporter or the analgesic compound were administered alone thereby providing a greater than additive analgesic effect in combination. In some instances, the lower amount of the analgesic compound and/or the lower amount of the selective inhibitor of neuronal norepinephrine transporter is a sub-analgesic amount in which one or both of the components of the combination are administered at a dosage normally considered not to provide an analgesic or pain relief effect.

Alternatively, the term "synergistic" when used in relation to the combination refers to a combination that extends the duration of the analgesic or pain relief effect beyond the duration observed when either the analgesic agent, particularly morphine, or the selective inhibitor of neuronal norepinephrine transporter is administered alone. In this instance, the amount of analgesic agent and/or selective inhibitor may be the same as the amount normally provided in a single dose to achieve analgesia, thereby allowing a lower amount of analgesic agent and/or selective inhibitor of neuronal norepinephrine transporter to be administered over the course of multiple doses of analgesic or pain relief therapy as dosing is less frequent.

In some embodiments of the invention, the selection of analgesic agent and selective inhibitor of neuronal norepinephrine transporter may allow lower amounts of analgesic agent and/or selective inhibitor to provide a better than additive analgesic or pain relief effect than if either component of the combination were administered in the same amount alone, and also extension of the duration of analgesic or pain relief effect.

The term "sub-analgesic amount" refers to an amount of active compound that is normally not considered to provide an analgesic effect in a patient or provides less than maximal analgesic effect. A sub-analgesic amount will differ for each patient and may depend on whether a patient has developed tolerance to a particular analgesic agent or selective inhibitor of the neuronal norepinephrine transporter. A sub-analgesic amount for a patient with tolerance may provide a maximal analgesic effect in a naïve or intolerant patient.

The neuronal norepinephrine transporter (NET) is a transporter of neuronal amine neurotransmitters such as norepinephrine (also known as noradrenaline). NET functions to rapidly clear released norepinephrine (NE) from the synapse back into neurons, thus inhibiting the re-uptake of NE by neurons. Well known inhibitors of NET such as tricyclic antidepressants (TCAs) act competitively at the NE binding site (orthosteric), both in NET membrane binding assays and in assays that measure the inhibition of NE uptake. However, TCAs do not inhibit NET selectively, having significant activity at other monoamine transporters such as SERT and DAT, as well as to some CNS receptors. Reboxetine, a small molecule inhibitor of NET also has some activity towards other monoamine transporters such as DAT and SERT so cannot be considered a selective inhibitor of NET. In addition, reboxetine produces only relatively mild analgesia in animals (Obata et al., (2005) *Pain* 113, 271-276) and is not considered a genuine candidate for i.t. pain therapy. Similarly, TCAs provide only mild analgesic actions. Although TCAs are known to potentiate the effects of opioids in rodents and humans (Bohn et al., (2000) *J. Neuroscience* 20(24), 9040-9045), it is unclear whether this is directly an effect of TCAs binding to NET or due to their significant activity at other monoamine transporters. This effect may also be related to the mode TCAs bind to NET, for example, as competitive inhibitors and therefore this observation cannot be extrapolated as a generality to other classes of NET inhibitors given the differences in mode of action, selectivity and chemical composition. In particular, it does not relate to the ability of NET inhibitors that do not act at the NE orthosteric site (e.g. those that act at allosteric sites) to provide analgesic effects or whether they can act synergistically with opioids. Specification of the importance of endogenous bulbospinal noradrenergic projections in the anti-hyperpathic actions remains controversial because of the relatively poor specificity of common NET inhibitors (Nielsen et al., (2005) Pain 118, 112-124).

In preferred embodiments, the inhibitor of the neuronal norepinephrine transporter is an isolated, synthetic or recombinant χ-conotoxin peptide having the ability to inhibit the neuronal norepinephrine transporter. The χ-conotoxin peptide may be a naturally occurring peptide isolated from a cone snail, or a derivative of a naturally occurring χ-conotoxin peptide. Alternatively, the χ-conotoxin peptide or its derivative may be prepared by synthetic or recombinant means or a combination of synthetic and recombinant or isolating and synthetic methods.

Naturally occurring χ-conotoxin peptides, MrIA and MrIB, have been isolated from the venom of the mollusc hunting cone snail, *Conus marmoneus*. They are both peptides of 13 amino acid residues in length, and contain 2 disulfide bonds.

The amino acid sequences of MrIA and MrIB are as follows:

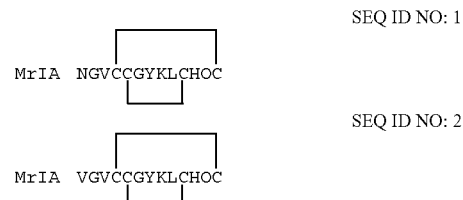

In these peptides, the cysteine in the 4-position and the cysteine in the 13-position form a disulfide bond and the cysteine in the 5-position and the cysteine in the 10-position form a disulfide bond. The C-terminus may be a free acid or may be amidated.

In the sequences above the "O" refers to 4-hydroxy proline (Hyp). This amino acid residue results from post translational modification of the encoded peptide and is not directly encoded by the nucleotide sequence.

Preferably, the χ-conotoxin peptide is a selective inhibitor of the neuronal norepinephrine transporter. The terms "selective" and "selectively" as used herein mean that the activity of the peptide as an inhibitor of the neuronal norepinephrine transporter is considerably greater than any activity at other monoamine transporter targets such as the dopamine transporter (DAT) and the serotonin transporter (SERT).

The term "derivative" as used herein in connection with naturally occurring χ-conotoxin peptides, such as MrIA and MrIB, refers to a peptide which differs from the naturally occurring peptides by one or more amino acid deletions, additions, substitutions, or side-chain modifications. Such derivatives which do not have the ability to selectively inhibit the neuronal norepinephrine transporter do not fall within the scope of the present invention.

Substitutions encompass amino acid alterations in which an amino acid is replaced with a different naturally-occurring or a non-conventional amino acid residue. Such substitutions may be classified as "conservative", in which case an amino acid residue contained in a polypeptide is replaced with another naturally-occurring amino acid of similar character either in relation to polarity, side chain functionality or size, for example Ser↔Thr↔Pro↔Hyp↔Gly↔Ala, Val↔Ile↔Leu, His↔Lys↔Arg, Asn↔Gln↔Asp↔Glu↔Glu or Phe↔Trp↔Tyr. It is to be understood that some non-conventional amino acids may also be suitable replacements for the naturally occurring amino acids. For example ornithine, homoarginine and dimethyllysine are related to His, Arg and Lys.

Substitutions encompassed by the present invention may also be "non-conservative", in which an amino acid residue which is present in a peptide is substituted with an amino acid having different properties, such as naturally-occurring amino acid from a different group (eg. substituting a charged or hydrophobic amino acid with alanine), or alternatively, in which a naturally-occurring amino acid is substituted with a non-conventional amino acid.

Amino acid substitutions are typically of single residues, but may be of multiple residues, either clustered or dispersed.

Preferably, amino acid substitutions are conservative.

Additions encompass the addition of one or more naturally occurring or non-conventional amino acid residues. Deletion encompasses the deletion of one or more amino acid residues.

The χ-conotoxin peptides may also be peptides in which one or more of the amino acids has undergone side-chain modifications. Examples of side-chain modifications contemplated include modifications of amino groups such as by reductive alkylation, by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$. The guanidine group of arginine residues may be modified by the formation of heterocyclic condensation products with reagents such as 2,3-butanedione, phenylglyoxal and glyoxal. The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide compounds; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH. Any modification of cysteine residues must not affect the ability of the peptide to form the necessary disulphide bonds. It is also possible to replace the sulphydryl groups of cysteine with selenium equivalents such that the peptide forms a diselenium bond in place of one or more of the disulphide bonds.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Proline residues may be modified by, for example, hydroxylation in the 4-position.

Suitable naturally occurring proteogenic amino acids are shown in Table 1 together with their one letter and three letter codes.

TABLE 1

| Amino Acid | one letter code | three letter code |
|---|---|---|
| L-alanine | A | Ala |
| L-arginine | R | Arg |
| L-asparagine | N | Asn |
| L-aspartic acid | D | Asp |
| L-cysteine | C | Cys |
| L-glutamine | Q | Gln |
| L-glutamic acid | E | Glu |
| glycine | G | Gly |
| L-histidine | H | His |
| L-isoleucine. | I | Ile |
| L-leucine | L | Leu |
| L-lysine | K | Lys |
| L-methionine | M | Met |
| L-phenylalanine | F | Phe |
| L-proline | P | Pro |
| L-serine | S | Ser |
| L-threonine | T | Thr |
| L-tryptophan | W | Trp |
| L-tyrosine | Y | Tyr |
| L-valine | V | Val |

A list of some amino acids having modified side chains and other unnatural amino acids is shown in Table 2.

TABLE 2

| Non-conventional amino acid | Code | Non-conventional amino acid | Code |
|---|---|---|---|
| α-aminobutyric acid | Abu | L-N-methylalanine | NmAla |
| α-amino-α-methylbutyrate | Mgabu | L-N-methylarginine | NmArg |
| aminocyclopropane-carboxylate | Cpro | L-N-methylasparagine | NmAsn |
| | | L-N-methylaspartic acid | NmAsp |

TABLE 2-continued

| Non-conventional amino acid | Code | Non-conventional amino acid | Code |
|---|---|---|---|
| aminoisobutyric acid | Aib | L-N-methylcysteine | NmCys |
| aminonorbornyl- | Norb | L-N-methylglutamine | NmGln |
| carboxylate | | L-N-methylglutamic acid | NmGlu |
| cyclohexylalanine | Chexa | L-N-methylhistidine | NmHis |
| cyclopentylalanine | Cpen | L-N-methylisoleucine | NmIle |
| D-alanine | DAla | L-N-methylleucine | NmLeu |
| D-arginine | DArg | L-N-methyllysine | NmLys |
| D-asparagine | DAsn | L-N-methylmethionine | NmMet |
| D-aspartic acid | DAsp | L-N-methylnorleucine | NmNle |
| D-cysteine | DCys | L-N-methylnorvaline | NmNva |
| D-glutamine | DGln | L-N-methylornithine | NmOrn |
| D-glutamic acid | DGlu | L-N-methylphenylalanine | NmPhe |
| D-histidine | DHis | L-N-methylproline | NmPro |
| D-isoleucine | DIle | L-N-methylserine | NmSer |
| D-leucine | DLeu | L-N-methylthreonine | NmThr |
| D-lysine | DLys | L-N-methyltryptophan | NmTrp |
| D-methionine | DMet | L-N-methyltyrosine | NmTyr |
| D-ornithine | DOrn | L-N-methylvaline | NmVal |
| D-phenylalanine | DPhe | L-N-methylethylglycine | Nmetg |
| D-proline | DPro | L-N-methyl-t-butylglycine | Nmtbug |
| D-serine | DSer | L-norleucine | Nle |
| D-threonine | DThr | L-norvaline | Nva |
| D-tryptophan | DTrp | α-methyl-aminoisobutyrate | Maib |
| D-tyrosine | DTyr | α-methyl-γ-aminobutyrate | Mgabu |
| D-valine | DVal | α-methylcyclohexylalanine | Mchexa |
| D-α-methylalanine | DmAla | α-methylcylcopentylalanine | Mcpen |
| D-α-methylarginine | DmArg | α-methyl-α-napthylalanine | Manap |
| D-α-methylasparagine | DmAsn | α-methylpenicillamine | Mpen |
| D-α-methylaspartate | DmAsp | N-(4-aminobutyl)glycine | Nglu |
| D-α-methylcysteine | DmCys | N-(2-aminoethyl)glycine | Naeg |
| D-α-methylglutamine | DmGln | N-(3-aminopropyl)glycine | Norn |
| D-α-methylhistidine | DmHis | N-amino-α-methylbutyrate | Nmaabu |
| D-α-methylisoleucine | DmIle | α-napthylalanine | Anap |
| D-α-methylleucine | DmLeu | N-benzylglycine | Nphe |
| D-α-methyllysine | DmLys | N-(2-carbamylethyl)glycine | Ngln |
| D-α-methylmethionine | DmMet | N-(carbamylmethyl)glycine | Nasn |
| D-α-methylornithine | DmOrn | N-(2-carboxyethyl)glycine | Nglu |
| D-α-methylphenylalanine | DmPhe | N-(carboxymethyl)glycine | Nasp |
| D-α-methylproline | DmPro | N-cyclobutylglycine | Ncbut |
| D-α-methylserine | DmSer | N-cyclodecylglycine | Ncdec |
| D-N-methylserine | DnmSer | N-cycloheptylglycine | Nchep |
| D-α-methylthreonine | DmThr | N-cyclohexylglycine | Nchex |
| D-α-methyltryptophan | DmTrp | N-cyclodecylglycine | Ncdec |
| D-α-methyltyrosine | DmTyr | N-cylcododecylglycine | Ncdod |
| D-α-methylvaline | DmVal | N-cyclooctylglycine | Ncoct |
| D-N-methylalanine | DnmAla | N-cyclopropylglycine | Ncpro |
| D-N-methylarginine | DnmArg | N-cycloundecylglycine | Ncund |
| D-N-methylasparagine | DnmAsn | N-(2,2-diphenylethyl)glycine | Nbhm |
| D-N-methylaspartate | DnmAsp | N-(3,3-diphenylpropyl)glycine | Nbhe |
| D-N-methylcysteine | DnmCys | N-(3-guanidinopropyl)glycine | Narg |
| D-N-methylglutamine | DnmGln | N-(1-hydroxyethyl)glycine | Nthr |
| D-N-methylglutamate | DnmGlu | N-(hydroxyethyl))glycine | Nser |
| D-N-methylhistidine | DnmHis | N-(imidazolylethyl))glycine | Nhis |
| D-N-methylisoleucine | DnmIle | N-(3-indolylyethyl)glycine | Nhtrp |
| D-N-methylleucine | DnmLeu | N-methyl-γ-aminobutyrate | Nmgabu |
| D-N-methyllysine | DnmLys | D-N-methylmethionine | DnmMet |
| N-methylcyclohexylalanine | Nmchexa | N-methylcyclopentylalanine | Nmcpen |
| D-N-methylornithine | DnmOrn | D-N-methylphenylalanine | DnmPhe |
| N-methylglycine | Nala | D-N-methylproline | DnmPro |
| N-methylaminoisobutyrate | Nmaib | D-N-methylserine | DnmSer |
| N-(1-methylpropyl)glycine | Nile | D-N-methylthreonine | DnmThr |
| N-(2-methylpropyl)glycine | Nleu | N-(1-methylethyl)glycine | Nval |
| D-N-methyltryptophan | DnmTrp | N-methyla-napthylalanine | Nmanap |
| D-N-methyltyrosine | DnmTyr | N-methylpenicillamine | Nmpen |
| D-N-methylvaline | DnmVal | N-(p-hydroxyphenyl)glycine | Nhtyr |
| γ-aminobutyric acid | Gabu | N-(thiomethyl)glycine | Ncys |
| L-t-butylglycine | Tbug | penicillamine | Pen |
| L-ethylglycine | Etg | L-α-methylalanine | MAla |
| L-homophenylalanine | HPhe | L-α-methylasparagine | MAsn |
| L-α-methylarginine | MArg | L-α-methyl-t-butylglycine | Mtbug |
| L-α-methylaspartate | MAsp | L-methylethylglycine | Metg |
| L-α-methylcysteine | MCys | L-α-methylglutamate | MGlu |
| L-α-methylglutamine | MGln | L-α-methylhomophenylalanine | MhPhe |
| L-α-methylhistidine | MHis | N-(2-methylthioethyl)glycine | Nmet |
| L-α-methylisoleucine | MIle | L-α-methyllysine | MLys |
| L-α-methylleucine | MLeu | L-α-methylnorleucine | MNle |
| L-α-methylmethionine | MMet | L-α-methylornithine | MOrn |

TABLE 2-continued

| Non-conventional amino acid | Code | Non-conventional amino acid | Code |
|---|---|---|---|
| L-α-methylnorvaline | MNva | L-α-methylproline | MPro |
| L-α-methylphenylalanine | MPhe | L-α-methylthreonine | MThr |
| L-α-methylserine | MSer | L-α-methyltyrosine | MTyr |
| L-α-methyltryptophan | MTrp | L-N-methyl-homophenylalanine | NmhPhe |
| L-α-methylvaline | MVal | N-(N-(3,3-diphenylpropyl) | Nnbhe |
| N-(N-(2,2-diphenylethyl) carbamylmethylglycine | Nnbhm | L-pyroglutamic acid | pGlu & Pyr |
| | | O-methyl-L-serine | Omser |
| 1-carboxy-1-(2,2-diphenyl-ethylamino)cyclopropane | Nmbc | O-methyl-L-homoserine | Omhser |
| | | 5-hydroxylysine | HLys |
| 4-hydroxyproline | Hyp | α-carboxyglutamate | Gla |
| ornithine | Orn | phenylglycine | Phg |
| 2-aminobenzoyl(anthraniloyl) | ABZ | L-pipecolic acid (homoproline) | Pip |
| cyclohexylalanine | Cha | L-homoleucine | Hle |
| 4-phenyl-phenylalanine | Bib | L-lysine (dimethyl) | DMK |
| L-citrulline | Cit | L-naphthylalanine | Nal |
| N-cyclohexylglycine | Nchex | L-dimethyldopa or L-dimethoxy-phenylalanine | DMD |
| L-1,2,3,4-tetrahydroisoquinoline-3-carboxylic acid | Tic | L-3-pyridylalanine | PYA |
| L-thiazolidine-4-carboxylic acid | THZ | L-histidine (benzoyloxymethyl) | HBO |
| L-homotyrosine | hTyr | N-cycloheptylglycine | Nchep |
| L-2-furylalanine | FLA | L-diphenylalanine | DPA |
| L-histidine (3-methyl) | HME | O-methyl-L-homotyrosine | OmhTyr |
| N-(3-guanidinopropyl)glycine | Narg | L-β-homolysine | BHK |
| O-methyl-L-tyrosine | MeY | O-glycan-threoine | g-Thr |
| O-glycan-serine | g-Ser | Ortho-tyrosine | o-Tyr |
| Meta-tyrosine | m-Tyr | L-N,N'-dimethyllysine | DMK |
| Nor-tyrosine | nor-Tyr | L-homoarginine | homoArg |
| L-N,N',N''-trimethyllysine | TMK | neotryptophan | neo-tryp |
| D-pyroglutamic acid | Dpglu | N-glycan Asparagine | g-Asn |
| homolysine | homolys | norlysine | nor-Lys |

These types of modifications may be important to stabilise the peptide if administered to an individual.

Other derivatives of the χ-conotoxin peptides include a range of glycosylation variants from a completely unglycosylated molecule to a modified glycosylated molecule. Altered glycosylation patterns may result from expression of recombinant molecules in different host cells. Optionally, in the peptides of SEQ ID NO: 3 or 4, the Asn residues may be modified to contain an N-glycan and the Ser, Thr and Hyp residues may be modified to contain an O-glycan. In accordance with the present invention, a glycan shall mean any N—, S- or O-linked mono-, di-, tri-, poly- or oligosaccharide that can be attached to any hydroxy, amino or thiol group of natural or modified amino acids by synthetic or enzymatic methodologies known in the art.

The monosaccharides making up the glycan may include D-allose, D-altrose, D-glucose, D-mannose, D-gulose, D-idose, D-galactose, D-talose, D-galactosamine, D-glucosamine, D-N-acetyl-glucosamine (GlcNAc), D-N-acetyl-galactosamine (GalNAc), D-fucose or D-arabinose. These saccharides may be structurally modified e.g., with one or more O-sulfate, O-phosphate, O-acetyl or acidic groups, such as sialic acid, including combinations thereof. The glycan may also include similar polyhydroxy groups, such as D-penicillamine 2,5 and halogenated derivatives thereof or polypropylene glycol derivatives. The glycosidic linkage may be beta and 1-4 or 1-3, preferably 1-3. The linkage between the glycan and the amino acid may be alpha or beta, preferably alpha.

Core O-glycans have been described by Van de Steen et al. (1998) Critical Rev. in Biochem. and Mol. Biol., 33:151-208, incorporated herein by reference. Mucin type O-linked oligosaccharides are attached to Ser or Thr (or other hydroxylated residues of the present peptides) by a GalNAc residue. The monosaccharide building blocks and the linkage attached to this first GalNAc residue define the "core glycans", of which eight have been identified. The type of glycosidic linkage (orientation and connectivities) are defined for each core glycan. Suitable glycans and glycan analogs are described further in U.S. Pat. No. 6,369,193 and in WO 00/23092, both incorporated herein by reference. A preferred glycan is Gal(β1→3)GalNAc(α1→).

The χ-conotoxins of the present invention are typically amidated at the C-terminal, however compounds with a free carboxyl terminus or other modifications at the C-terminal are considered to be within the scope of the present invention. In some embodiments, the peptides are amidated or have a free carboxyl at the C-terminal.

Preferably the derivatives of naturally occurring χ-conotoxin peptides will retain the Cys residues and characteristic disulphide bonding pattern. Derivatives may include additional Cys residues provided they are protected during formation of the disulphide bonds.

Exposed residues are most likely to be involved in receptor binding and can be systematically replaced. Particular emphasis is placed on changing residues involved in binding and residues just on the periphery of the pharmacophore, using longer side chain forms or non-conserved changes to pick up additional binding interactions for improved potency and/or selectivity. Reducing or enlarging loop sizes and the tail of MrIA or MrIB further modifies activity.

It is noted that MrIA and MrIB are composed of a tail (residues 1-3), and two loops (residues 6-9 and 11-12), however the χ-conotoxin peptides and derivatives useful in the present invention are not restricted to those having this particular arrangement of amino acids and disulphide bonds. Other arrangements are also possible, and provided the resultant peptide has the requisite activity, a peptide will be useful in the methods of the present invention. Preferably the peptides will have at least two cysteine residues and at least one disulphide bond, or more preferably four cysteine residues and two disulphide bonds.

The connectivity of the disulfide bonds in these peptides may be A-B/C-D, A-C/B-D or A-D/B-C, the latter being preferred for MrIA and MrIB. A, B, C and D refer to the first, second, third and fourth Cys residues involved in disulphide bond formation, respectively.

In a preferred embodiment of the present invention, the χ-conotoxin peptide is an isolated, synthetic or recombinant χ-conotoxin peptide having the ability to inhibit the neuronal norepinephrine transporter comprising the following sequence of amino acids:

SEQ ID NO: 3
Cys$_1$ Cys$_2$ Gly Tyr Lys Leu Cys$_3$ Xaa8 Xaa9 Cys$_4$ where Xaa8 and Xaa9 are independently absent or represent any natural or non-natural amino acid residue except Cys, or such a sequence in which Gly, Tyr, Lys or Leu are subject to conservative amino acid substitution or side chain modification, or a salt, ester, amide, prodrug or cyclised derivative thereof. In some embodiments, Cys$_1$ is connected to Cys$_4$ and Cys$_2$ is connected to Cys$_3$ by disulfide bonds.

It has also been found that the introduction of at least one additional amino acid residue at the N-terminus can increase the binding affinity of the peptide for the human norepinephrine transporter. Furthermore, it has been found that the modification of at least one additional amino acid residue at the N-terminus can increase binding affinity of the peptide for the human norepinephrine transporter.

Preferred χ-conotoxin peptides include isolated, synthetic or recombinant χ-conotoxin peptides having the ability to inhibit neuronal amine transporter comprising the following sequence of amino acids:

SEQ ID NO: 4
Xaa0 Xaa1 Xaa2 Xaa3 Xaa4 Cys$_1$ Cys$_2$ Gly Xaa5 Xaa6 Xaa7 Cys$_3$ Xaa8 Xaa9 Cys$_4$ Xaa10 where
Xaa0 is selected from Ala, Lys, Phe, Tyr, pGlu, Gln, Asp, Asn, Leu, Orn, Trp, hPhe and a deletion;
Xaa1 is selected from Trp, DTrp, Tyr, Phe, hPhe, Ala, MeY, Arg, Ben, Nap, Orn, pGlu, DpGlu, Gln, Asp, Asn, Pro, Hyp and a deletion;
Xaa2 is selected from Arg, Ala, Asn, Lys, Phe, BHK, Orn, DArg, Nle, DLys, DMK, DAsn, Thr, ABZ, Nap, Cit, Val, Tyr, Trp, pGlu, DpGlu, Gln, Thr, Glu, Asp and a deletion;
Xaa3 is selected from Gly, Asp, Lys, Arg, Ala, Nle, Ser, Phe, Leu, Glu, Gla, Asn, Thr, g-Asn, g-Ser, g-Thr and a deletion;
Xaa4 is selected from Val, Leu, Nle, Ile, Thr, Ala, Asn, Trp, Phe, Gly, Ser, Abu, g-Asn, g-Ser and g-Thr;
Xaa5 is selected from Tyr, MeY, Phe, m-Tyr, o-Tyr, norTyr, mono-halo-Tyr, di-halo-Tyr, O-sulpho-Tyr, O-phospho-Tyr, nitro-Tyr, Trp, DTrp, neo-Trp, halo-Trp (D and L), any non-natural aromatic amino acid, an aliphatic amino acid bearing linear or branched saturated hydrocarbon chains and a non-natural derivative of the aliphatic amino acid;
Xaa6 is selected from Lys, Arg, homoLys, homoArg, Orn, nor-Lys, His, N-methyl lysine, DMK, TMK, any non-natural basic amino acid, Ser, Thr, g-Ser, g-Thr and any non-natural hydroxylated amino acid;
Xaa7 is selected from Leu, DLeu, Nle, Ile, Hle, Val, Ala, Met, Phe, Tyr, m-Tyr, o-Tyr, norTyr, mono-halo-Tyr, di-halo-Tyr, O-sulpho-Tyr, O-phospho-Tyr, nitro-Tyr, Trp, DTrp, neo-Trp, halo-Trp (D and L) and any non-natural aromatic amino acid;
Xaa8 and Xaa9 are as defined above;
Xaa10 is selected from Gly, Ala, Lys, Arg, homoLys, homoArg, Orn, nor-Lys, His, N-methyl Lysine, DMK, TMK and any non-natural basic amino acid or Xaa10 is a deletion;

or a salt, ester, amide, prodrug or cyclised derivative thereof.

In another embodiment, the χ-conotoxin peptide is an isolated, synthetic or recombinant χ-conotoxin peptide having the ability to inhibit neuronal norepinephrine transporter comprising the following sequence of amino acids:

SEQ ID NO: 5
Xaa0 Xaa1 Xaa2 Xaa3 Xaa4 Cys$_1$ Cys$_2$ Gly Tyr Lys Leu Cys$_3$ Xaa8 Xaa9 Cys$_4$ where
Xaa0 is selected from Ala, Lys, Phe, Tyr, pGlu, Gln, Asp, Asn, Leu, Orn, Trp, hPhe and a deletion;
Xaa1 is selected from Trp, DTrp, Tyr, Phe, hPhe, Ala, MeY, Arg, Ben, Nap, Orn, pGlu, DpGlu, Gln, Asp, Asn, Pro, Hyp and a deletion;
Xaa2 is selected from Arg, Ala, Asn, Lys, Phe, BHK, Orn, DArg, Nle, DLys, DMK, DAsn, Thr, ABZ, Nap, Cit, Val, Tyr, Trp, pGlu, DpGlu, Gln, Thr, Glu, Asp and a deletion;
Xaa3 is selected from Gly, Asp, Lys, Arg, Ala, Nle, Ser, Phe, Leu, Glu, Gla, Asn, Thr, g-Asn, g-Ser, g-Thr and a deletion;
Xaa4 is selected from Val, Leu, Nle, Ile, Thr, Ala, Asn, Trp, Phe, Gly, Ser, Abu, g-Asn, g-Ser and g-Thr; and
Xaa8 and Xaa9 are as defined above, or such a sequence where one or more of the loop 1 residues Gly, Tyr, Lys and Leu are subject to conservative amino acid substitution or side chain modification, or a salt, ester, amide, prodrug or cyclised derivative thereof.

Preferred embodiments of SEQ ID NO: 4 include those where Xaa0 is a deletion and Xaa1 is an N-terminal residue and is selected from pGlu, Pro, Hyp or an N-acetylated amino acid residue.

In some embodiments of the above formulae Cys$_1$ is connected to Cys$_4$ and Cys$_2$ is connected to Cys$_3$ by disulfide bonds.

In the above formulae, the following definitions apply:

Tyrosine (Tyr) is an amino acid in which the side chain is a 4-hydroxyphenylmethyl group (a para or p-hydroxy group). Meta- (m-Tyr) and ortho-tyrosine (o-Tyr) have the hydroxy groups in the 3- and 2-positions respectively. The hydroxy group of tyrosine, whether it is in the 2, 3, or 4 position may be substituted with groups such as sulfate and phosphate to provide O-sulfotyrosine or O-phosphotyrosine. The tyrosine in any of these non-naturally occurring residues and derivatives may be in the D- or L-configuration.

Tyrosine, in either the D or L configuration, may also be substituted on the aromatic ring with one or more halo groups to form, for example, monohalo-tyrosine or dihalo-tyrosine. Tryptophan, in either the D or L configuration, may also be substituted on the indole group with one or more halo groups to form, for example, monohalo-tryptophan or dihalo-tryptophan. The term "halo" refers to halogen and is selected from fluoro, chloro, bromo and iodo, especially iodo for substitution at tyrosine and bromo for substitution at tryptophan.

Neotryptophan is a non-natural amino acid having the structural formulae:

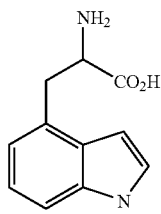

This non-natural amino acid may be in the D- or L-configuration. Its synthesis and incorporation into polypeptides is described in U.S. Pat. No. 6,214,790.

The term "aliphatic amino acid bearing linear or branched saturated hydrocarbon chains" refers to amino acids such as alanine, leucine, isoleucine, and valine. These amino acids may be in the D- or L-configuration.

The term "non-natural derivative of an aliphatic amino acid" as used herein refers to amino acids in the D- or L-configuration bearing non-naturally occurring saturated linear or branched side chains, preferably having the formula —$C_2H_{2n+1}$, where n is 1 to 8.

The term "non-natural aromatic amino acid" as used herein refers to amino acids that are non-naturally occurring and include an aromatic ring in their side chain. Examples of non-natural aromatic amino acids include, but are not limited to, neotryptophan, phenylglycine, naphthylalanine, 3-pyridylalanine, diphenylalanine and substituted derivatives of naturally occurring amino acids. Substituted derivatives of naturally occurring amino acids include, but are not limited to, phenylalanine, tyrosine, histidine or tryptophan substituted at one or more aromatic carbon atoms. Suitable substituents include, but are not limited to, methyl, ethyl, propyl, isopropyl, halo, phenyl, carboxyl, nitro, cyano, $SO_3H$, sulphomethyl, $NH_2$ and NHAc, where halo is selected from fluoro, chloro, bromo and iodo. Non-natural aromatic amino acids also include tyrosine residues, including those where the hydroxy group is in the 2, 3 or 4 position on the aromatic ring, in which the hydroxy group is further substituted. The hydroxy group may be substituted, for example, sulfo group to form O-sulphotyrosine or a phospho group to form O-phosphotyrosine. Examples of non-natural aromatic amino acids include, but are not limited to, neotryptophan, phenylglycine, naphthylalanine, 3-pyridylalanine, diphenylalanine, o-tyrosine, m-tyrosine, O-sulfotyrosine, O-phosphotyrosine, monohalo-tyrosine, dihalo-tyrosine, monohalotryptophan, dihalo-tryptophan, nitrophenylalanine, 4-phenylphenylalanine, 2,6-dimethyltyrosine, 5-aminotyrosine, 4-hydroxyphenylglycine and 4-hydroxy-methyltyrosine. Each of these non-natural aromatic amino acids may be in the D- or L-configuration. These and other non-natural aromatic amino acids are described in Building Block Index, Version 3.0 (1999 Catalogue), pages 4-47.

The term "non-natural hydroxylated amino acid" refers to non-naturally occurring amino acids having a hydroxy substituent in their side chain. Examples of non-natural hydroxylated amino acids include, but are not limited to, 4-hydroxymethylphenylalanine, 4-hydroxyphenylglycine, 2,6-dimethyltyrosine, 5-aminotyrosine, D-serine, D-threonine, D-tyrosine, homoserine, nor-tyrosine, homotyrosine, m-tyrosine and o-tyrosine. Each of these hydroxy containing amino acids, unless otherwise stated, may occur in the D- or L-configuration. These and other non-natural hydroxy containing amino acids are described in Building Block Index, Version 3.0 (1999 Catalogue), pages 4-47.

The term "non-natural basic amino acid" refers to non-naturally occurring amino acids having a basic group in their side chain. Examples of non-natural basic amino acids include, but are not limited to, D-lysine, D-hisitidine, D-arginine, 3-pyridylalanine, N-1-(2-pyrazolinyl)-arginine, 2-(4-piperinyl)-glycine, 2-(4-piperinyl)-arginine, 2-[3-(2S)-pyrrolininyl]-glycine and 2-[3-(2S)-pyrrolininyl]-arginine. These and other non-natural basic amino acids are described in Building Block Index, Version 3.0 (1999 Catalogue), pages 66-87.

In preferred embodiments, the χ-conotoxin peptides include one or more of the following features:

In SEQ ID NOS: 4 and 5 Xaa0 is preferably Trp, Tyr or hPhe or a deletion. More preferably Xaa0 is a deletion.

In SEQ ID NOS: 4 and 5 Xaa1 is preferably a deletion.

In SEQ ID NOS: 4 and 5 Xaa2 is preferably pGlu, Glu, Gln, Asn or Asp, more preferably Xaa2 is pGlu.

In SEQ ID NOS: 4 and 5 Xaa3 is preferably Gly, Ala or Asp. More preferably Xaa3 is Gly.

In SEQ ID NOS: 4 and 5 Xaa4 is preferably Leu, Nle, Ala, Ile or Val.

In SEQ ID NOS: 3, 4 and 5 the following preferred definitions apply for Xaa8 and Xaa9:

Preferably Xaa8 is selected from His, Arg, Trp, NaI, Glu, Gln and a deletion. More preferably Xaa8 is Arg or His.

Xaa9 is selected from Hyp, Pro, Ala, Tic, Pip, MeY, DMD, Phe, THZ, Glu, Nle, Tyr and a deletion. More preferably Xaa9 is Hyp or Pro.

In a preferred embodiment, the χ-conotoxin peptide is

SEQ ID NO: 6 pGlu Gly Val $Cys_1$ $Cys_2$ Gly Tyr Lys Leu $Cys_3$ His Hyp $Cys_4$ wherein $Cys_1$ is connected to $Cys_4$ and $Cys_2$ is connected to $Cys_3$ by disulfide bonds.

Examples of suitable χ-conotoxin peptides include those listed in Table 3 where in each peptide $Cys_1$ is connected to $Cys_4$ and $Cys_2$ is connected to $Cys_3$ by disulfide bonds:

TABLE 3

| SEQ ID. NO. * | Xaa0 | Xaa1 | Xaa2 | Xaa3 | Xaa4 | Cys | Cys | Gly | Xaa5 | Xaa6 | Xaa7 | Cys | Xaa8 | Xaa9 | Cys |
|---|---|---|---|---|---|---|---|---|---|---|---|---|---|---|---|
| 6 | | | pGlu | Gly | Val | Cys | Cys | Gly | Tyr | Lys | Leu | Cys | His | Hyp | Cys |
| 7§ | | | | Gly | Val | Cys | Cys | Gly | Tyr | Lys | Leu | Cys | His | Hyp | Cys |
| 8§ | | | | Gly | Ile | Cys | Cys | Gly | Val | Ser | Phe | Cys | Tyr | Hyp | Cys |
| 9§ | | | | | Ala | Cys | Cys | Gly | Tyr | Lys | Leu | Cys | Ser | Hyp | Cys |

TABLE 3-continued

| SEQ ID. NO. * | Xaa0 | Xaa1 | Xaa2 | Xaa3 | Xaa4 | Cys | Cys | Gly | Xaa5 | Xaa6 | Xaa7 | Cys | Xaa8 | Xaa9 | Cys | |
|---|---|---|---|---|---|---|---|---|---|---|---|---|---|---|---|---|
| 10§ | | | | Gln | Thr | Cys | Cys | Gly | Tyr | Arg | Met | Cys | Val | Hyp | Cys | Gly |
| 11§ | | | | Ser | Thr | Cys | Cys | Gly | Phe | Lys | Met | Cys | Ile | Hyp | Cys | |
| 12§ | | | | | Val | Cys | Cys | Gly | Tyr | Lys | Leu | Cys | His | Hyp | Cys | |
| 13 | | | | Gly | Ile | Cys | Cys | Gly | Tyr | Lys | Leu | Cys | Tyr | Hyp | Cys | |
| 14 | | | Tyr | Arg | Gly | Leu | Cys | Cys | Gly | MeY | Lys | Leu | Cys | Arg | Hyp | Cys |
| 15 | | | Tyr | Arg | Gly | Nle | Cys | Cys | Gly | MeY | Lys | Leu | Cys | Arg | Hyp | Cys |
| 16 | Orn | Tyr | Arg | Gly | Nle | Cys | Cys | Gly | MeY | Lys | Leu | Cys | Arg | Hyp | Cys | |
| 17 | | | Trp | Arg | Gly | Leu | Cys | Cys | Gly | MeY | Lys | Leu | Cys | His | Hyp | Cys |
| 18 | | | Orn | Arg | Gly | Nle | Cys | Cys | Gly | MeY | Lys | Leu | Cys | Arg | Hyp | Cys |
| 19 | | Lys | Tyr | Arg | Gly | Nle | Cys | Cys | Gly | MeY | Lys | Leu | Cys | Arg | Hyp | Cys |
| 20 | | | | BHK | Gly | Nle | Cys | Cys | Gly | MeY | Lys | Hle | Cys | His | Hyp | Cys |
| 21 | | | Trp | Arg | Gly | Val | Cys | Cys | Gly | MeY | Lys | Leu | Cys | His | Hyp | Cys |
| 22 | | | Trp | Lys | Gly | Val | Cys | Cys | Gly | MeY | Lys | Leu | Cys | His | Hyp | Cys |
| 23 | | Phe | Arg | Tyr | Gly | Nle | Cys | Cys | Gly | MeY | Lys | Leu | Cys | Arg | Hyp | Cys |
| 24 | Tyr | Orn | Arg | Gly | Nle | Cys | Cys | Gly | MeY | Lys | Leu | Cys | Arg | Hyp | Cys | |
| 25 | | | DTrp | Arg | Gly | Leu | Cys | Cys | Gly | MeY | Lys | Leu | Cys | Arg | Ala | Cys |
| 26 | | | Trp | Arg | Gly | Val | Cys | Cys | Gly | MeY | Lys | Leu | Cys | His | Hyp | Cys |
| 27 | | | Trp | Arg | Gly | Leu | Cys | Cys | Gly | Tyr | Lys | Leu | Cys | His | Hyp | Cys |
| 28 | | | | BHK | Gly | Nle | Cys | Cys | Gly | Tyr | Lys | Hle | Cys | His | Hyp | Cys |
| 29 | | Tyr | Phe | Arg | Gly | Nle | Cys | Cys | Gly | MeY | Lys | Leu | Cys | Arg | Hyp | Cys |
| 30 | | | Trp | Arg | Gly | Val | Cys | Cys | Gly | MeY | Lys | Leu | Cys | Arg | Ala | Cys |
| 31 | | | Trp | Arg | Gly | Val | Cys | Cys | Gly | Tyr | Lys | Leu | Cys | His | Hyp | Cys |
| 32 | | | | Trp | Gly | Leu | Cys | Cys | Gly | MeY | Lys | Leu | Cys | Arg | Tyr | Cys |
| 33 | | | | BHK | Gly | Nle | Cys | Cys | Gly | MeY | Lys | Leu | Cys | His | Hyp | Cys |
| 34 | | | Trp | Asn | Gly | Val | Cys | Cys | Gly | Tyr | Lys | Leu | Cys | His | Hyp | Cys |
| 35 | | Ac | Tyr | Arg | Gly | Leu | Cys | Cys | Gly | MeY | Lys | Leu | Cys | Arg | Hyp | Cys |
| 36 | | | | Trp | Gly | Leu | Cys | Cys | Gly | MeY | Lys | Leu | Cys | Arg | Hyp | Cys |
| 37 | | | Trp | Arg | Gly | Leu | Cys | Cys | Gly | MeY | Lys | Leu | Cys | Arg | Lys | Cys |
| 38 | | | Trp | Arg | Gly | Leu | Cys | Cys | Gly | MeY | Lys | Leu | Cys | Arg | Ala | Cys |
| 39 | | | Trp | Arg | Gly | Val | Cys | Cys | Gly | Tyr | Lys | Leu | Cys | Arg | Ala | Cys |
| 40 | | | Trp | Asn | Gly | Val | Cys | Cys | Gly | Tyr | Lys | Leu | Cys | Arg | Hyp | Cys |
| 41 | | | Trp | Arg | Gly | Val | Cys | Cys | Gly | MeY | Lys | Leu | Cys | His | Ala | Cys |
| 42 | pGlu | Tyr | Arg | Gly | Nle | Cys | Cys | Gly | MeY | Lys | Leu | Cys | Arg | Hyp | Cys | |
| 43 | | | | Orn | Gly | Nle | Cys | Cys | Gly | MeY | Lys | Hle | Cys | His | Hyp | Cys |
| 44 | | | Trp | Arg | Gly | Val | Cys | Cys | Gly | Tyr | Lys | Leu | Cys | His | Hyp | Cys | Tyr |
| 45 | | | | Trp | Gly | Leu | Cys | Cys | Gly | MeY | Lys | Leu | Cys | Arg | Hyp | Cys | Tyr |
| 46 | | | | Orn | Gly | Nle | Cys | Cys | Gly | MeY | Lys | Leu | Cys | His | Hyp | Cys |
| 47 | | | Trp | Asn | Gly | Val | Cys | Cys | Gly | MeY | Lys | Leu | Cys | His | Hyp | Cys |
| 48 | | | | Asn | Gly | Nle | Cys | Cys | Gly | MeY | Lys | Hle | Cys | His | Hyp | Cys |

TABLE 3-continued

| SEQ ID. NO. * | Xaa0 | Xaa1 | Xaa2 | Xaa3 | Xaa4 | Cys | Cys | Gly | Xaa5 | Xaa6 | Xaa7 | Cys | Xaa8 | Xaa9 | Cys | |
|---|---|---|---|---|---|---|---|---|---|---|---|---|---|---|---|---|
| 49 | | | Orn | Gly | Nle | Cys | Cys | Gly | MeY | Lys | Nle | Cys | His | Hyp | Cys | |
| 50 | | | BHK | Gly | Val | Cys | Cys | Gly | Tyr | Lys | Hle | Cys | His | Hyp | Cys | |
| 51 | | Tyr | Asn | Gly | Nle | Cys | Cys | Gly | Tyr | Lys | Leu | Cys | His | Pro | Cys | |
| 52 | | | Orn | Gly | Leu | Cys | Cys | Gly | MeY | Lys | Leu | Cys | His | Hyp | Cys | |
| 53 | | | Orn | Gly | Nle | Cys | Cys | Gly | Tyr | Lys | Hle | Cys | His | Hyp | Cys | |
| 54 | | Trp | Asn | Gly | Val | Cys | Cys | Gly | MeY | Lys | Leu | Cys | His | Pro | Cys | |
| 55 | | Trp | Arg | Gly | Val | Cys | Cys | Gly | Tyr | Lys | Leu | Cys | His | Ala | Cys | |
| 56 | Asp | Tyr | Arg | Gly | Nle | Cys | Cys | Gly | MeY | Lys | Leu | Cys | Arg | Hyp | Cys | |
| 57 | | Tyr | Asn | Gly | Val | Cys | Cys | Gly | Tyr | Lys | Hle | Cys | His | Pro | Cys | |
| 58 | | | Asn | Gly | Nle | Cys | Cys | Gly | Tyr | Lys | Nle | Cys | His | Hyp | Cys | |
| 59 | | | BHK | Gly | Nle | Cys | Cys | Gly | Tyr | Lys | Leu | Cys | His | Hyp | Cys | |
| 60 | | | Asn | Gly | Val | Cys | Cys | Gly | Tyr | Lys | Leu | Cys | Trp | Pro | Cys | |
| 61 | | Trp | Asn | Gly | Val | Cys | Cys | Gly | Tyr | Lys | Leu | Cys | Arg | Pro | Cys | |
| 62 | | | Asn | Gly | Nle | Cys | Cys | Gly | MeY | Lys | Nle | Cys | His | Hyp | Cys | |
| 63 | | Tyr | Asn | Gly | Val | Cys | Cys | Gly | MeY | Lys | Leu | Cys | Arg | Ala | Cys | |
| 64 | | | Asn | Asp | Val | Cys | Cys | Gly | Tyr | Lys | Leu | Cys | His | Pro | Cys | |
| 65 | | Trp | Arg | Gly | Leu | Cys | Cys | Gly | Tyr | Lys | Leu | Cys | Arg | Gly | Cys | |
| 66 | | | pGlu | Gly | Leu | Cys | Cys | Gly | MeY | Lys | Leu | Cys | Arg | Hyp | Cys | Tyr |
| 67 | | | Orn | Gly | Nle | Cys | Cys | Gly | Tyr | Lys | Nle | Cys | His | Hyp | Cys | |
| 68 | | hPhe | Asn | Gly | Val | Cys | Cys | Gly | Tyr | Lys | Leu | Cys | His | Hyp | Cys | |
| 69 | | Tyr | Asn | Gly | Val | Cys | Cys | Gly | Tyr | Lys | Leu | Cys | Arg | Hyp | Cys | |
| 70 | | Trp | Asn | Gly | Val | Cys | Cys | Gly | Tyr | Lys | Leu | Cys | Arg | Ala | Cys | |
| 71 | Phe | Gly | Gly | Phe | Trp | Cys | Cys | Gly | MeY | Lys | Leu | Cys | Arg | Ala | Cys | |
| 72 | | Tyr | Asn | Gly | Val | Cys | Cys | Gly | Tyr | Lys | Leu | Cys | Trp | Hyp | Cys | |
| 73 | | Trp | Asn | Gly | Leu | Cys | Cys | Gly | MeY | Lys | Leu | Cys | His | Hyp | Cys | |
| 74 | | | BHK | Gly | Nle | Cys | Cys | Gly | Tyr | Lys | Leu | Cys | His | Pro | Cys | |
| 75 | | | Asn | Gly | Nle | Cys | Cys | Gly | MeY | Lys | Leu | Cys | His | Hyp | Cys | |
| 76 | | | BHK | Gly | Val | Cys | Cys | Gly | MeY | Lys | Leu | Cys | His | Pro | Cys | |
| 77 | | | BHK | Gly | Val | Cys | Cys | Gly | Tyr | Lys | Hle | Cys | His | Pro | Cys | |
| 78 | | | DArg | Gly | Val | Cys | Cys | Gly | MeY | Lys | Leu | Cys | His | Hyp | Cys | |
| 78 | | Trp | Arg | Gly | Leu | Cys | Cys | Gly | Tyr | Lys | Leu | Cys | Arg | Ala | Cys | |
| 80 | | | BHK | Gly | Val | Cys | Cys | Gly | MeY | Lys | Leu | Cys | His | Hyp | Cys | |
| 81 | | | Asn | Gly | Nle | Cys | Cys | Gly | Tyr | Lys | Hle | Cys | His | Hyp | Cys | |
| 82 | | Tyr | Asn | Gly | Val | Cys | Cys | Gly | Tyr | Lys | Leu | Cys | Arg | Ala | Cys | |
| 83 | | Trp | Asn | Gly | Val | Cys | Cys | Gly | Tyr | Lys | Leu | Cys | His | Pro | Cys | |
| 84 | | Phe | Gly | Gly | Phe | Cys | Cys | Gly | MeY | Lys | Leu | Cys | Arg | Ala | Cys | |
| 85 | | Tyr | Asn | Gly | Val | Cys | Cys | Gly | Tyr | Lys | Leu | Cys | Arg | Pro | Cys | |
| 86 | | Trp | Lys | Asp | Leu | Cys | Cys | Gly | Tyr | Lys | Leu | Cys | His | Pro | Cys | |

TABLE 3-continued

| SEQ ID. NO. * | Xaa0 | Xaa1 | Xaa2 | Xaa3 | Xaa4 | Cys | Cys | Gly | Xaa5 | Xaa6 | Xaa7 | Cys | Xaa8 | Xaa9 | Cys |
|---|---|---|---|---|---|---|---|---|---|---|---|---|---|---|---|
| 87 | | | Tyr | Asn | Gly | Val | Cys | Cys | Gly | MeY | Lys | Leu | Cys | His | Pro | Cys |
| 88 | | | | BHK | Gly | Val | Cys | Cys | Gly | Tyr | Lys | Leu | Cys | Arg | Hyp | Cys |
| 89 | | | Tyr | Asn | Gly | Val | Cys | Cys | Gly | Tyr | Lys | Leu | Cys | His | Hyp | Cys |
| 90 | | | Tyr | Asn | Gly | Val | Cys | Cys | Gly | Tyr | Lys | Leu | Cys | Arg | Pro | Cys |
| 91 | | | Trp | Lys | Asp | Leu | Cys | Cys | Gly | Tyr | Lys | Leu | Cys | Trp | Pro | Cys |
| 92 | | | Tyr | Asn | Gly | Val | Cys | Cys | Gly | Tyr | Lys | Leu | Cys | Trp | Pro | Cys |
| 93 | | | Trp | Lys | Asp | Val | Cys | Cys | Gly | Tyr | Lys | Leu | Cys | Trp | Pro | Cys |
| 94 | | | | BHK | Gly | Val | Cys | Cys | Gly | Tyr | Lys | Leu | Cys | His | Pro | Cys |
| 95 | | | Tyr | Asn | Gly | Val | Cys | Cys | Gly | MeY | Lys | Leu | Cys | — | Pro | Cys |
| 96 | | | Trp | BHK | Gly | Val | Cys | Cys | Gly | Tyr | Lys | Leu | Cys | His | Hyp | Cys |
| 97 | | | | Orn | Gly | Nle | Cys | Cys | Gly | Tyr | Lys | Leu | Cys | His | Hyp | Cys |
| 98 | | | | Asn | Gly | Leu | Cys | Cys | Gly | Tyr | Lys | Leu | Cys | His | Pro | Cys |
| 99 | | | | Arg | Gly | Val | Cys | Cys | Gly | Tyr | Lys | Leu | Cys | His | Pro | Cys |
| 100 | cyclic ( | Gly | Tyr | Lys | Leu | Gly | Cys | Cys | Gly | Tyr | Lys | Leu | Cys | — | — | Cys ) |
| 101 | Trp | Ala | Ala | Asn | Gly | Val | Cys | Cys | Gly | Tyr | Lys | Leu | Cys | His | Hyp | Cys |
| 102 | | | | BHK | Gly | Val | Cys | Cys | Gly | Tyr | Lys | Leu | Cys | His | Hyp | Cys |
| 103 | | | | Asn | Gly | Val | Cys | Cys | Gly | Tyr | Lys | Leu | Cys | His | Tic | Cys |
| 104 | | | | DArg | Gly | Val | Cys | Cys | Gly | Tyr | Lys | Leu | Cys | His | Hyp | Cys |
| 105 | | | MeY | Asn | Gly | Val | Cys | Cys | Gly | Tyr | Lys | Leu | Cys | His | Pro | Cys |
| 106 | Gly | Ile | Leu | Arg | Asn | Gly | Val | Cys | Cys | Gly | Tyr | Lys | Leu | Cys | His | Pro | Cys |
| 107 | | | Trp | Ala | Asn | Gly | Val | Cys | Cys | Gly | Tyr | Lys | Leu | Cys | His | Hyp | Cys |
| 108 | | | | Nle | Gly | Val | Cys | Cys | Gly | MeY | Lys | Leu | Cys | His | Hyp | Cys |
| 109 | | | | Orn | Gly | Val | Cys | Cys | Gly | Tyr | Lys | Leu | Cys | His | Pro | Cys |
| 110 | | Ac | Trp | BHK | Gly | Val | Cys | Cys | Gly | Tyr | Lys | Leu | Cys | His | Hyp | Cys |
| 111 | | | Tyr | Asn | Lys | Val | Cys | Cys | Gly | Tyr | Lys | Leu | Cys | His | Pro | Cys |
| 112 | | | | BHK | Gly | Val | Cys | Cys | Gly | Tyr | Lys | Leu | Cys | His | Tic | Cys |
| 113 | | | | Asn | Gly | Nle | Cys | Cys | Gly | Tyr | Lys | Leu | Cys | His | Hyp | Cys |
| 114 | | | | Asn | Gly | Val | Cys | Cys | Gly | MeY | Lys | Leu | Cys | His | Pro | Cys |
| 115 | | | Ac | BHK | Gly | Val | Cys | Cys | Gly | Tyr | Lys | Leu | Cys | His | Hyp | Cys |
| 116 | | | | Asn | Gly | Leu | Cys | Cys | Gly | Tyr | Lys | Leu | Cys | His | Hyp | Cys |
| 117 | | | Tyr | Asn | Gly | Val | Cys | Cys | Gly | Tyr | Lys | Leu | Cys | His | Pro | Cys |
| 118 | | | | Asn | Gly | Val | Cys | Cys | Gly | Tyr | Lys | Leu | Cys | His | Lys | Cys |
| 119 | | | Tyr | Asn | Arg | Val | Cys | Cys | Gly | Tyr | Lys | Leu | Cys | His | Pro | Cys |
| 120 | | | | Nle | Gly | Val | Cys | Cys | Gly | Tyr | Lys | Leu | Cys | His | Hyp | Cys |
| 121 | | | Ben | Asn | Gly | Val | Cys | Cys | Gly | Tyr | Lys | Leu | Cys | His | Pro | Cys |
| 122 | | | | DLys | Gly | Val | Cys | Cys | Gly | Tyr | Lys | Leu | Cys | His | Hyp | Cys |
| 123 | | | | Asn | Lys | Val | Cys | Cys | Gly | Tyr | Lys | Leu | Cys | His | Pro | Cys |
| 124 | | | | Asn | Gly | Val | Cys | Cys | Gly | MeY | Lys | Leu | Cys | His | Hyp | Cys |
| 125 | | | | Asn | Ala | Val | Cys | Cys | Gly | Tyr | Lys | Leu | Cys | His | Hyp | Cys |

TABLE 3-continued

| SEQ ID. NO. * | Xaa0 | Xaa1 | Xaa2 | Xaa3 | Xaa4 | Cys | Cys | Gly | Xaa5 | Xaa6 | Xaa7 | Cys | Xaa8 | Xaa9 | Cys |
|---|---|---|---|---|---|---|---|---|---|---|---|---|---|---|---|
| 126 | | | Asn | Gly | Ile | Cys | Cys | Gly | Tyr | Lys | Leu | Cys | His | Pro | Cys |
| 127 | | | Asn | Gly | Val | Cys | Cys | Gly | Tyr | Lys | Nle | Cys | His | Hyp | Cys |
| 128 | | | DMK | Gly | Val | Cys | Cys | Gly | Tyr | Lys | Leu | Cys | His | Hyp | Cys |
| 129 | | | DAsn | Gly | Val | Cys | Cys | Gly | Tyr | Lys | Leu | Cys | His | Hyp | Cys |
| 130 | | | Asn | Gly | Val | Cys | Cys | Gly | Tyr | Lys | Leu | Cys | His | Pip | Cys |
| 131 | | | Ala | Gly | Val | Cys | Cys | Gly | Tyr | Lys | Leu | Cys | His | Hyp | Cys |
| 132 | | Nap | Asn | Gly | Val | Cys | Cys | Gly | Tyr | Lys | Leu | Cys | His | Pro | Cys |
| 133 | | Tyr | Asn | Nle | Val | Cys | Cys | Gly | Tyr | Lys | Leu | Cys | His | Pro | Cys |
| 134 | | | Phe | Gly | Val | Cys | Cys | Gly | Tyr | Lys | Leu | Cys | His | Hyp | Cys |
| 135 | | | Asn | Gly | Val | Cys | Cys | Gly | Tyr | Lys | Leu | Cys | Nal | Pro | Cys |
| 136 | | | Thr | Gly | Val | Cys | Cys | Gly | Tyr | Lys | Leu | Cys | His | Hyp | Cys |
| 137 | | | ABZ | Gly | Val | Cys | Cys | Gly | Tyr | Lys | Leu | Cys | His | Hyp | Cys |
| 138 | | | Nap | Gly | Val | Cys | Cys | Gly | Tyr | Lys | Leu | Cys | His | Pro | Cys |
| 139 | | | Asn | Gly | Thr | Cys | Cys | Gly | Tyr | Lys | Leu | Cys | His | Pro | Cys |
| 140 | | | Cit | Gly | Val | Cys | Cys | Gly | Tyr | Lys | Leu | Cys | His | Hyp | Cys |
| 141 | | pGlu | Asn | Gly | Val | Cys | Cys | Gly | MeY | Lys | Leu | Cys | His | Hyp | Cys |
| 142 | | | Asn | Gly | Val | Cys | Cys | Gly | Tyr | Lys | Leu | Cys | His | MeY | Cys |
| 143 | | | Pro | Gly | Val | Cys | Cys | Gly | Tyr | Lys | Leu | Cys | His | Hyp | Cys |
| 144 | | Ac | Asn | Gly | Val | Cys | Cys | Gly | Tyr | Lys | Leu | Cys | His | Hyp | Cys |
| 145 | | | DpGlu | Gly | Val | Cys | Cys | Gly | Tyr | Lys | Leu | Cys | His | Hyp | Cys |
| 146 | | | Asn | Gly | Val | Cys | Cys | Gly | Tyr | Lys | Leu | Cys | His | Ala | Cys |
| 147 | | | Asn | Gly | Val | Cys | Cys | Gly | Tyr | Lys | Leu | Cys | His | Pro | Cys |
| 148 | | | Asp | Gly | Val | Cys | Cys | Gly | Tyr | Lys | Leu | Cys | His | Hyp | Cys |
| 149 | | | | | Val | Cys | Cys | Gly | Tyr | Lys | Leu | Cys | — | — | Cys |
| 150 | | | Asn | Gly | Val | Cys | Cys | Gly | Tyr | Lys | Leu | Cys | His | DMD | Cys |
| 151 | | | Asn | Gly | Ala | Cys | Cys | Gly | Tyr | Lys | Leu | Cys | His | Hyp | Cys |
| 152 | | | Asp | Gly | Val | Cys | Cys | Gly | Tyr | Lys | Leu | Cys | His | Pro | Cys |
| 153 | | Ac | Asn | Gly | Val | Cys | Cys | Gly | Tyr | Lys | Leu | Cys | His | Pro | Cys |
| 154 | | | Asn | Gly | Ala | Cys | Cys | Gly | Tyr | Lys | Leu | Cys | His | Hyp | Cys |
| 155 | | pGlu | Asp | Val | Cys | Cys | Gly | Tyr | Lys | Leu | Cys | His | Hyp | Cys | |
| 156 | | | Asn | Gly | Val | Cys | Cys | Gly | Tyr | Lys | Leu | Cys | His | Phe | Cys |
| 157 | | | Asn | Ser | Val | Cys | Cys | Gly | Tyr | Lys | Leu | Cys | His | Pro | Cys |
| 158 | | pGlu | Asn | Gly | Val | Cys | Cys | Gly | Tyr | Lys | Leu | Cys | His | Hyp | Cys |
| 159 | | | Asn | Gly | Val | Cys | Cys | Gly | Tyr | Lys | Leu | Cys | His | THZ | Cys |
| 160 | | | Asn | Gly | Val | Cys | Cys | Gly | Tyr | Lys | Leu | Cys | His | Glu | Cys |
| 161 | | | Asn | Gly | Abu | Cys | Cys | Gly | Tyr | Lys | Leu | Cys | His | Hyp | Cys |
| 162 | Ac | Tyr | Asn | Gly | Val | Cys | Cys | Gly | Tyr | Lys | Leu | Cys | His | Pro | Cys |
| 163 | | | Asn | Gly | Val | Cys | Cys | Gly | Tyr | Lys | Leu | Cys | His | Nle | Cys |

TABLE 3-continued

| SEQ ID. NO. * | Xaa0 | Xaa1 | Xaa2 | Xaa3 | Xaa4 | Cys | Cys | Gly | Xaa5 | Xaa6 | Xaa7 | Cys | Xaa8 | Xaa9 | Cys | |
|---|---|---|---|---|---|---|---|---|---|---|---|---|---|---|---|---|
| 164 | | Tyr | Asn | Gly | Val | Cys | Cys | Gly | Tyr | Lys | Leu | Cys | Gln | Pro | Cys | |
| 165 | | | DpGlu | Gly | Val | Cys | Cys | Gly | Tyr | Lys | Leu | Cys | His | Hyp | Cys | OH |
| 166 | | | Asn | Gly | Val | Cys | Cys | Gly | Tyr | Lys | Leu | Cys | His | Tyr | Cys | |

* disclosed in WO 04/050688
$ disclosed in U.S. application No. 09/580,201

The peptides useful in the methods of the present invention may be in the form of a salt, ester, amide, prodrug or, where appropriate, a cyclised derivative. The χ-conotoxins useful in the present invention are typically amidated at the C-terminal, however compounds with a free carboxyl terminus or other modifications, such as esterification at the C-terminal may also be useful. Preferably the peptides are amidated or have a free carboxyl at the C-terminal. The peptides useful in the present invention generally have a free N-terminus, although the N-terminus may be capped using a suitable capping group. Examples of suitable capping groups include, but are not limited to, acetyl (Ac), benzoyl (Ben) and Naphthyl (Nap).

The peptides may be in the form of a pharmaceutically acceptable salt. Examples of suitable salts include, but are not limited to, chloride, acetate, lactate and glutamate salts. Conventional procedures for the preparation of suitable salts are well known in the art.

The peptides useful in the present invention may also be in the form of prodrugs. Prodrugs are understood to include all derivatives of peptides according to the invention which are readily convertible in vivo into the required active peptide. Conventional procedures for the preparation of suitable prodrugs according to the invention are described in text books, such as "Design of Prodrugs" ed. H. Bundgaard, Elsevier, 1985.

Certain peptides useful in the present invention may also be in cyclised form, such that the N- or C-termini are linked head-to-tail either directly, or through the insertion of a linker moiety, such moiety itself generally consisting of one or more amino acid residues as required to join the backbone in such a manner as to avoid altering the three-dimensional structure of the peptide with respect to the non-cyclised form. Such peptide derivatives may have improved stability and bioavailability relative to the non-cyclised peptides. Methods for cyclising conotoxin peptides are described in WO 00/15654 (University of Queensland), the entire contents of which is incorporated herein by reference.

The peptides may retain the Cys residues and characteristic disulphide bonding pattern of χ-conotoxin peptides. Derivatives may include additional Cys residues provided they are protected during formation of the disulphide bonds.

In SEQ ID NOS: 3, 4 and 5, the Gly residue in loop 1 may be conservatively substituted or subjected to conservative side chain modification. One non-limiting example of a modification is DLys.

The χ-conotoxin peptides useful in the present invention may be prepared using standard peptide synthetic methods followed by oxidative disulfide bond formation. For example, the linear peptides may be synthesised by solid phase methodology using BOC chemistry, as described by Schnoltzer et al (1992), *Int. J. Peptide Protein Res.,* 40, 180. Following deprotection and cleavage from the solid support the reduced peptides are purified using preparative chromatography. The purified reduced peptides may be oxidised in buffered systems, for example, 30% DMSO/0.1 M $NH_4HCO_3$ at pH 6, 30% isopropanol/0.1 M $NH_4HCO_3$ at pH 8 or isopropanol/DMSO/0.1 M $NH_4HCO_3$ at pH 8. The oxidised peptides may be purified using preparative chromatography such as reverse phase HPLC.

References describing the synthesis of conotoxins include Sato et al (1997), *FEBS Letters,* 414, 480-484, Lew et al (1997), *J. Biol. Chem.,* 272, 12014-12023 and WO 91/07980. Sharpe et al., (2003) ("Inhibition of the Norepinephrine Transporter by the Venom Peptide ω-MrIA"), J. Biol. Chem., 278(41), 40317-40323) describes methods for the synthesis and non-selective oxidation of chi conotoxin peptides.

Other procedures known in the art for selective oxidation of the cysteine residues may also be used such as those described in Tam J P, Lu Y A, Yang J L. "Marked increase in membranolytic selectivity of novel cyclic tachyplesins constrained with an antiparallel two-beta strand cystine knot framework", Biochem Biophys Res Commun. 2000; 267(3):783-790; Yu Q, Lehrer R I, Tam J P. "Engineered salt-insensitive α-defensins with end-to-end circularized structures" J Biol Chem. 2000; 275(6):3943-3949; and Tam J P, Lu Y A, Yang J L, Chiu K W. "An unusual structural motif of antimicrobial peptides containing end-to-end macrocycle and cystine-knot disulfides" Proc Natl Acad Sci USA. 1999; 96(16):8913-8918.

Some of the χ-conotoxins useful in the present invention may also be prepared using recombinant DNA technology. A nucleotide sequence encoding the desired peptide sequence, or its precursor, may be inserted into a suitable vector and protein expressed in an appropriate expression system. In some instances, further chemical modification of the expressed peptide may be appropriate, for example C-terminal amidation or post translational modification of particular residues. Under some circumstances it may be desirable to undertake oxidative bond formation of the expressed peptide as a chemical step following peptide expression. This may be preceded by a reductive step to provide the unfolded peptide. Those skilled in the art may readily determine appropriate conditions for the reduction and oxidation of the peptide.

It should thus be understood that the terms conotoxin peptide or conotoxins are not limited to naturally occurring toxic peptides obtained from the genus *Conus* but rather simply indicates an initial source from which the peptides have been derived. Conotoxin peptides may be synthetically created, non-naturally occurring non-toxic peptide derivatives. Conopeptides is an alternative term interchangeable with conotoxin peptides.

The analgesic agent may be selected from the group consisting of opioid analgesics, N-type calcium channel blockers, opioid receptor-like antagonists, GPCR antagonists of the MRG family, capsaicin receptor agonists, NMDA antagonists, substance P antagonists, COX 1 and COX 2 inhibitors, tricyclic antidepressants (TCA), selective serotonin re-uptake inhibitors (SSRI), α2-adrenoreceptor agonists, gabapentin, anaesthetic agents, benzodiazepines, skeletal muscle relaxants, migraine therapeutic agents, anti-convulsants, anti-hypertensives, anti-arrhythmics, antihistamines, steroids, caffeine, nicotinic receptor partial agonists and antagonists, vanilloid receptor antagonists and agonists, TNF-α antagonists and antibodies, inhibitors of tetrodotoxin-sensitive Na Channels, P-type channel inhibitors, endothelian antagonists, botulinum toxin and mixtures thereof. In preferred embodiments, the analgesic agent is an opioid analgesic or an N-type calcium channel blocker.

Where the analgesic agent is an opioid receptor-like analgesic agent it is preferably selected from naltrexone and nalmefene; their pharmaceutically active salts and their optical isomers.

Where the analgesic agent is an opioid analgesic agent it is preferably selected from propoxyphene, meperidine, hydromorphone, hydrocodone, morphine, codeine, methadone, fentanyl, sufentanil, alfentanil, oxymorphone, oxycodone, hydrocodeine, levorphanol, heroin, morphine-6-glucuronide, levallorphan, 6-monoacetylmorphine and tramodol; their pharmaceutically active salts and their optical isomers.

When the analgesic agent is an N-type calcium channel blocker, it is preferably an ω-conotoxin such as those described in WO 93/13128 and WO 99/54350, the entire contents of which are incorporated herein by reference. Particularly preferred ω-conotoxins are selected from

and derivatives and pharmaceutically acceptable salts thereof. The term "derivative" as used herein in relation to CVID or MVIIA, refers to a peptide which differs from CVID or MVIIA by one or more amino acid deletions, additions, substitutions, or side-chain modifications. Substitutions may be conservative or non-conservative as described for the χ-conotoxins above. Suitable additions, deletions and side-chain modifications have also been described in relation to χ-conotoxins above. Derivatives that do not have the ability to selectively inhibit N-type calcium channels are not useful in the methods of the invention.

Where the analgesic agent is an NMDA antagonist analgesic agent it is preferably selected from 2-piperidino-1-alkanol derivatives, dextromethorphan, memantine, ketamine, liprodil, and ifenprodil; their pharmaceutically active salts and their optical isomers.

Where the analgesic agent is a COX 2 inhibition analgesic agent it is preferably selected from rofecoxib and celecoxib; their pharmaceutically active salts and their optical isomers.

Where the analgesic agent is an anaesthetic analgesic agent it is preferably selected from nitrous oxide, halothane, lidocaine, etidocaine, ropivacaine, chloroprocaine, sarapin, bupivacaine, levobupivacaine, mepivacaine, prilocalne, procaine and articaine; their pharmaceutically active salts and their optical isomers.

Where the analgesic agent is a benzodiazepine analgesic agent it is preferably selected from diazepam, chlordiazepoxide, clonazepam, alprazolam, lorazepam, midazolam, L-365260; their pharmaceutically active salts and their optical isomers.

Where the analgesic agent is a skeletal muscle relaxant analgesic agent it is preferably selected from flexeril, carisoprodol, robaxisal, norgesic and dantrium their pharmaceutically active salts and their optical isomers.

Where the analgesic agent is a migraine therapeutic agent it is preferably selected from elitriptan, sumatriptan, rizatriptan, zolmitriptan, and naratriptan their pharmaceutically active salts and their optical isomers.

Where the analgesic agent is an anticonvulsant analgesic agent it is preferably selected from gabapentin, pregabalin, carbamazepine, and topiramate and valproic acid their pharmaceutically active salts and their optical isomers.

Where the analgesic agent is a COX 1 inhibitor analgesic agent it is preferably selected from salicylic acid, acetominophen, diclofenac, piroxican indomethacin, ibuprofen, and naproxen their pharmaceutically active salts and their optical isomers.

Where the analgesic agent is a tricyclic antidepressant analgesic agent it is preferably selected from amitriptyline, desipramine, perphenazine, protriptyline, and tranylcypromine their pharmaceutically active salts and their optical isomers.

Where the analgesic agent is a SSRI analgesic agent it is preferably selected from tramadol and milnacipran; their pharmaceutically active salts and their optical isomers.

Where the analgesic agent is a mixture of SSRI and Norepinephrine re-uptake inhibitors, the latter is preferably selected from reboxetine and atomoxetine; their pharmaceutically active salts and their optical isomers.

The analgesic agent may also be selected from adenosine, baclofen, clonidine, mexilitene, diphenyl-hydramine, hydroxysine, caffeine, prednisone, methylprednisone, decadron, paroxetine, sertraline, fluoxetine, Ziconotide®. and levodopa their pharmaceutically active salts and their optical isomers.

Where the analgesic agent is a TNF-α antagonist or antibody, the agent is preferably selected from etanercept, infliximab and thalidomide; their pharmaceutically active salts and their optical isomers.

Where the analgesic agent is an endothelian antagonist, the agent is preferably selected from bosentan and tesosentan; their pharmaceutically active salts and their optical isomers.

Where the analgesic agent is a vanilloid antagonist, the analgesic agent is preferably selected from ananamide, capsazepine, thiocarbamic acid derivatives (as described in WO02/16317 A1) and thiourea derivatives (as described in WO02/16318 A1); their pharmaceutically active salts and their optical isomers.

The methods of the invention may be used to produce analgesia or provide pain relief or control pain. The pain may be acute or chronic pain and may be nociceptive pain, neuropathic pain or mixed category pain. Nociceptive pain is caused by nerves (nociceptors) which sense and respond to parts of the body that suffer damage or are about to suffer damage. Nociceptive pain may be localised, constant and include aching or throbbing or may be visceral pain associated with internal organs which may be poorly localised and episodic. Nociceptive pain usually decreases as and if the damage heals. Examples of nociceptive pain include acute trauma, osteoarthritis, rheumatoid arthritis, musculo-skeletal pain, particularly after trauma, spinal pain, dental pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhea, and labor pain, post operative pain, shingles and gout.

Neuropathic pain is caused by injury or malfunction in the peripheral or central nervous system. The pain is often triggered by an injury but the injury may not involve actual damage to the nervous system. Neuropathic pain frequently includes burning, lancinating or electric shock type pain and may also include allodynia, pain resulting from a non-painful stimulus such as a light touch. Neuropathic pain may persist for months or years and is often chronic. Examples of neuropathic pain include pain associated with nerve and root damage, such as pain associated with peripheral nerve disorders, for example, nerve entrapment and brachial plexus avulsions, amputation, peripheral neuropathies, neuralgia, tic douloureux, atypical facial pain, nerve root damage, pain and/or chronic nerve compression, and arachnoiditis; pain associated with carcinoma, often referred to as cancer pain; pain associated with AIDS, central nervous system pain, such as pain due to spinal cord or brain stem damage; low back pain; sciatica; headache, including migraine, acute or chronic tension headache, cluster headache, temporomandibular pain and maxillary sinus pain; ankylosing spondylitis; post-herpetic pain; phantom pains; diabetic neuropathy; and scar pain.

Mixed category pain includes a complex mixture of nociceptive and neuropathic pain. Examples of mixed category pain include migraine headaches and myofascial pain.

An effective amount of a selective inhibitor of the neuronal norepinephrine transporter is one that is effective in enhancing or increasing the pain relieving potency or duration of effect of the analgesic agent. In one embodiment, the amount of inhibitor that is administered as a bolus is in a sub-analgesic amount in the range of 0.001 mg to 50 mg, preferably 0.005 mg to 40 mg, 0.01 mg to 30 mg, 0.03 mg to 20 mg and especially 0.05 mg to 15 mg. In another embodiment, the amount of inhibitor that is administered is as a repeat bolus is in a sub-analgesic amount in the range of 0.001 mg/day to 50 mg/day, preferably 0.005 mg/day to 40 mg/day, 0.01 mg/day to 30 mg/day, 0.03 mg/day to 20 mg/day and especially 0.05 mg/day to 15 mg/day. In another embodiment, the amount of inhibitor that is administered is as an infusion in a sub-analgesic amount in the range of 0.040 µg/hr to 2084 µg/hr, preferably 0.2 µg/hr to 1670 µg/hr, 0.40 µg/hr to 1250 µg/hr, 1.25 µg/hr to 830 µg/hr and especially 2 µg/hr to 625 µg/hr. In another embodiment the dosage of inhibitor is a sub-analgesic dosage where the dosage is less than required to achieve a maximum analgesic effect. For example the sub-analgesic amount may be an $ED_5$ to $ED_{90}$ amount which is effective to produce an analgesic effect in 5% to 90% of patients. Preferably the sub-analgesic amount corresponds to an $ED_5$ to $ED_{80}$ amount, an $ED_5$ to $ED_{70}$ amount, an $ED_5$ to $ED_{60}$ amount, an $ED_5$ to $ED_{50}$ amount, an $ED_5$ to $ED_{40}$ amount and especially and $ED_5$ to $ED_{30}$ amount. In an especially preferred embodiment, the sub-analgesic amount of inhibitor is an $ED_{10}$ amount.

The effective amount of analgesic agent administered is one that is sufficient, when combined with a selective inhibitor of the neuronal norepinephrine transporter, to achieve a beneficial response in the patient over time, such as a reduction in, or relief from, pain.

The quantity of the pharmaceutically active compound(s) to be administered may depend on the subject to be treated inclusive of the age, sex, weight and general health condition thereof. In this regard, precise amounts of the active compound(s) for administration will depend on the judgement of the practitioner. In determining the effective amount of the active compound(s) to be administered in the production of analgesia, particularly when the analgesic agent is an opioid analgesic, the physician may evaluate severity of the pain symptoms associated with nociceptive or neuropathic pain conditions and the amount of opioid analgesic, and may consider whether the patient is opioid analgesic naïve or whether previous long term exposure to an opioid analgesic has occurred. Long term administration of opioid analgesics may cause tolerance in a patient and such patients may require higher doses of opioid analgesics than opioid naïve patients to achieve the same level of analgesia or pain relief. In any event, those of skill in the art may readily determine suitable dosages of the selective inhibitors of neuronal norepinephrine transporters and/or analgesic agents useful in the invention without undue experimentation.

When the analgesic agent is an opioid analgesic agent, an effective amount may be an amount which is the recommended dosage for opioid naïve patients or for patients tolerant to analgesic effects of opioids. For example, in a morphine naïve adult patient, a standard dosage is 5-20 mg if delivered by intramuscular or subcutaneous injection, or 2.5-15 mg if delivered by intravenous injection. Morphine may also be administered in an oral immediate release tablet or capsule in a dosage of 10-30 mg or in an oral sustained release dosage form of 40 mg or 20 mg. Morphine may also be administered to a morphine naïve adult patient by epidural administration (5 mg), intrathecal administration (0.2-1 mg) or by intracerebroventricular administration (0.1-1 mg). Dosages of morphine suitable for administration to children include 0.1-0.2 mg/kg to a maximum of 15 mg by intramuscular or subcutaneous injection or with caution 0.05-0.1 mg/kg incrementally over 5 -15 minutes if titrated intravenously. Although the above dosages for intramuscular or subcutaneous injection or oral immediate release tablets or capsules are normally provided at a frequency of every 4-6 hours, in combination with a selective inhibitor of the neuronal norepinephrine transporter according to the invention, the frequency of dosing may be extended to every 5-7 hours, 6-8 hours, 7-9 hours, 8-10 hours, 9-11 hours, 10-12 hours, 11-13 hours up to as long as 48 hours. Although the above dosage forms for oral sustained release formulations are normally provided at a frequency of 40 mg/24 hours or 20 mg/12 hours, these formulations may, in combination with a selective inhibitor of the neuronal norepinephrine transporter according to the invention, be provided at longer intervals, such as 25, 26, 27, 28, 29, 30, 31, 32, 33, 34, 35, 36 hours, up to 48 hours or 13, 14, 15, 16, 17, 18 hours up to 48 hours. Standard doses given above for epidural, intrathecal or intracerebroventricular administration are normally provided at a frequency of every 24 hours. However, in combination with the selective inhibitor of the neuronal norepinephrine transporter according to the present invention, the frequency of dosing may be extended to, for example, 25, 26, 27, 28, 29, 30, 31, 32, 33, 34, 35, 36, 48 hour or longer intervals.

Standard oxycodone dosages for opioid naïve adult patients include 1-10 mg by intravenous injection or 1-10 mg by intramuscular or subcutaneous injection. Oral administration may be by immediate release tablets in a dosage of 5-10 mg or in a sustained release oral dosage form of 10 mg. Oxycodone dosages may also be administered in 30 mg by rectal suppository. Although the above oxycodone dosages for intravenous, intramuscular or subcutaneous injection or oral immediate release tablets are normally provided every 4-6 hours, in combination with the selective inhibitor of the neuronal norepinephrine transporter according to the present invention, the frequency of dosing may be extended, for example, to every 5-7 hours, 6-8 hours, 7-9 hours, 8-10 hours, 9-11 hours, 11-12 hours or longer. Sustained release oral dosages of oxycodone are normally provided every 12 hours, however, in combination with a selective inhibitor of the neuronal norepinephrine transporter according to the present invention, this frequency may be extended for example, to every 13 hours, 14 hours, 15 hours, 16 hours, 17 hours, 18 hours or longer. The rectal suppository form of oxycodone is normally provided at a frequency of every 6-8 hours, however, in combination with a selective inhibitor of the neuronal norepinephrine transporter according to the present invention, this frequency of dosing may be extended to, for example, every 7-9 hours, 8-10 hours, 9-11 hours, 10-12 hours, 11-13 hours, 12-14 hours, 13-15 hours, 14-16 hours or longer.

Standard hydromorphone dosages for the production of analgesia in opioid-naïve patients include an oral dosage of 2-4 mg, 1-2 mg by intramuscular or subcutaneous injection, or 0.5-1.0 mg by intravenous injection delivered over 2-3 minutes. The frequency of administration of the oral dosage form is usually every 4 hours, however, in combination with the selective inhibitor of the neuronal norepinephrine transporter according to the present invention, the frequency of dosing may be extended to, for example, every 5 hours, 6 hours, 7 hours, 8 hours, 9 hours, 10 hours or longer. The frequency of dosing of the intramuscular or subcutaneous injection dosage forms is usually every 2 hours. However, in combination with a selective inhibitor of the neuronal norepinephrine transporter according to the present invention, this dosing frequency may be extended to, for example, every 3 hours, 4 hours, 5 hours, 6 hours, 7 hours, 8 hours or longer. Suitable dosages for children include oral dosages of 60 µg/kg or 15 µg/kg if delivered by intramuscular, subcutaneous or intravenous injection. The frequency of dosing for both oral and injectable forms of hydromorphone in children is usually every 3-4 hours. However, in combination with a selective inhibitor of the neuronal norepinephrine transporter according to the present invention, the frequency of dosing may be extended to, for example, every 4-5 hours, 5-6 hours, 6-7 hours, 7-8 hours, 8-9 hours, 9-10 hours or longer.

Suitable doses of fentanyl for the production of analgesia in opioid-naïve adult patients include 50-100 µg administered intramuscularly 30-60 minutes prior to surgery and 50-100 µg administered intramuscularly post-operatively as needed. Post-operative fentanyl is often delivered every 1-2 hours, however, in combination with the selective inhibitor of the neuronal norepinephrine transporter according to the present invention, the frequency of delivery may be extended to, for example, every 2-3 hours, 3-4 hours, 4-5 hours, 5-6 hours, 6-7 hours, 7-8 hours or longer. Fentanyl may also be delivered by transdermal patch at a dosage of 25 µg/hour.

Suitable doses of ω-conotoxin N-type calcium channel blockers such as MVIIA (SEQ ID NO: 168) and CVID (SEQ ID NO: 167) are in the range of 0.01 µg/day to about 30 µg/day, preferably 0.1 µg/day to 10 µg/day.

Alternatively, the analgesic agent may be administered in a sub-analgesic amount, which when administered alone, does not cause analgesia in a subject, however, when administered in combination with an effective amount of a selective inhibitor of the neuronal norepinephrine transporter, results in analgesia. For example, the sub-analgesic amount may be an $ED_5$ to $ED_{90}$ amount, which corresponds to a dose which is effective to produce an analgesic response in 5 to 90% of patients or subjects. Preferably, the sub-analgesic amount corresponds to one of an $ED_5$ to $ED_{80}$ amount, an $ED_5$ to an $ED_{70}$ amount, an $ED_5$ to an $ED_{60}$ amount, an $ED_5$ to an $ED_{50}$ amount, an $ED_5$ to an $ED_{40}$ amount and especially an $ED_5$ to an $ED_{30}$ amount. An especially preferred effective sub-analgesic amount is an $ED_{10}$ amount.

When the amount of analgesic agent administered is a standard or analgesic amount ($ED_{100}$), and is administered in combination with an effective amount of a selective inhibitor of the neuronal norepinephrine transporter, the duration of analgesic effect may be longer than that experienced when the same amount of analgesic agent is administered alone. This results in less frequent dosing of a subject with the analgesic agent and therefore fewer side effects are experienced and/or the side effects are of lesser severity.

When the amount of analgesic agent administered is a sub-analgesic amount, and is administered in combination with an effective amount of a selective inhibitor of the neuronal norepinephrine transporter, the analgesic effect experienced is of similar potency and duration as that experienced when a dosage 1.5 to 5 times greater, for example 3 times greater, is administered. This results in administration of much less analgesic agent being administered in any one dose and therefore fewer side effects are experienced and/or the side effects are of lesser severity. For example, any one or more of less allergic reactions, such as no or reduced difficulty breathing, swelling of lips, tongue, face and/or throat, or hives, no or reduced respiratory depression, less seizures or seizures of reduced severity; less cold, clammy skin, reduced weakness, no or reduced dizziness, reduced likelihood of unconsciousness, reduced or no sedation, reduced or no nausea, reduced or no vomiting or dry mouth, a reduction in loss of appetite, reduced or no constipation, reduced or no tiredness, reduced or no lightheadedness, reduced or no muscle twitching, reduced or no sweating, reduced or no pruritis, reduced or no urinary retention, and a reduction in loss of libido. In the case of opioid analgesics, there may also be a reduced likelihood of development of opioid analgesic tolerance or dependence.

The effect of the combination of a selective inhibitor of the neuronal norepinephrine transporter and analgesic agent may be examined using one or more of the published models of pain/nociception known in the art. The analgesic activity may be evaluated using methods known in the art, such as the Tail-flick Test (D'Amour et. al., 1941, *J. Pharmacol. Exp. Ther.* 72:74-79), the hotplate test (Eddy and Leimbach, 1953, *J. Pharmacol. Exp. Ther.*, 107:385-93), the paw pressure test (Randall and Selitto, 1957, *Arch. Int. Pharmacodyn.*, 111: 409-414), the paw thermal test (Hargreaves et. al., 1998, *Pain*, 32:77-88), the Brennan model of post-surgical pain (Brennan et. al., 1996, *Pain*, 64:493-501) and rodent neuropathic pain models (Kim, S. H. and Chung, J. M., 1992, *Pain*, 50, 355-363; Bennett, G. and Xie, Y. K., 1988, *Pain*, 33, 87-107).

In another aspect of the present invention there is provided a use of a selective inhibitor of the neuronal norepinephrine transporter in the manufacture of a medicament for use in a synergistic combination with an analgesic agent for producing analgesia or for the treatment or control of pain.

In another aspect of the present invention there is provided a use of an analgesic agent in the manufacture of a medicament for use in a synergistic combination with a selective inhibitor of the neuronal norepinephrine transporter for producing analgesia or for treatment or control of pain.

In yet another aspect of the invention there is provided a use of a synergistic combination of a selective inhibitor of the neuronal norepinephrine transporter and an analgesic agent in the preparation of a medicament for producing analgesia or for treatment or control of pain.

As will be readily appreciated by those skilled in the art, the formulation of, route of administration of and the nature of the pharmaceutically acceptable carrier will depend on the specific pain to be treated. Techniques for formulation and administration may be found in "Remington's Pharmaceutical Sciences", Mack Publishing Co., Easton, Pa., latest edition. It is believed that the choice of a particular carrier or delivery system, and route of administration could be readily determined by a person skilled in the art.

In the preparation of any formulation containing the peptide actives, care should be taken to ensure that the activity of the peptide is not destroyed in the process and that the peptide is able to reach its site of action without being destroyed. In some circumstances it may be necessary to protect the peptide by means known in the art such as microencapsulation. Similarly, the route of administration should be chosen such that the peptide reaches its site of pain.

The inhibitor of the norepinephrine transporter and/or the analgesic compound may be administered systemically, topically or locally. Suitable routes of administration may, for example, include oral, topical, rectal, transmucosal, intestinal administration or parenteral administration including intramuscular, subcutaneous, intramedullary, as well as intrathecal, epidural, direct intraventricular, intravenous, intraperitoneal, intranasal or intraocular injection. A preferred mode of administration of conotoxin peptides is intrathecal administration. Methods and formulations for using conotoxin peptides in intrathecal administration are described in WO 97/01351, the contents of which are incorporated by reference.

The analgesic agent and the selective inhibitor of the neuronal norepinephrine transporter may be formulated in a single composition, or may be formulated separately for simultaneous or sequential delivery by the same or different modes of administration. For example, the analgesic agent may be formulated for oral delivery and the inhibitor may be formulated for intrathecal administration, or the analgesic agent may be formulated for parenteral administration and the inhibitor formulated for oral delivery, or both the analgesic agent and the inhibitor may be formulated for administration by single or separate injection, such as intrathecal injection. Other combinations of modes of delivery could be readily determined by those skilled in the art.

The compositions of this invention may be formulated for administration in the form of liquids, containing acceptable diluents (such as saline and sterile water), or may be in the form of lotions, creams or gels containing acceptable diluents or carriers to impart the desired texture, consistency, viscosity and appearance. Acceptable diluents and carriers are familiar to those skilled in the art and include, but are not restricted to, ethoxylated and nonethoxylated surfactants, fatty alcohols, fatty acids, hydrocarbon oils (such as palm oil, coconut oil, and mineral oil), cocoa butter waxes, silicon oils, pH balancers, cellulose derivatives, emulsifying agents such as nonionic organic and inorganic bases, preserving agents, wax esters, steroid alcohols, triglyceride esters, phospholipids such as lecithin and cephalin, polyhydric alcohol esters, fatty alcohol esters, hydrophilic lanolin derivatives, and hydrophilic beeswax derivatives.

Alternatively, the active compounds of the present invention can be formulated readily using pharmaceutically acceptable carriers well known in the art into dosages suitable for oral administration. Such carriers enable the compounds of the invention to be formulated in dosage forms such as tablets, pills, capsules, liquids, gels, syrups, slurries, suspensions and the like, for oral ingestion by a patient to be treated. These carriers may be selected from sugars, starches, cellulose and its derivatives, malt, gelatine, talc, calcium sulphate, vegetable oils, synthetic oils, polyols, alginic acid, phosphate buffered solutions, emulsifiers, isotonic saline, and pyrogen-free water.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilisers or agents that increase the solubility of the compounds to allow for the preparation of highly concentrated solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatine, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Such compositions may be prepared by any of the methods of pharmacy but all methods include the step of bringing into association one or more therapeutic agents as described above with the carrier which constitutes one or more necessary ingredients. In general, the pharmaceutical compositions of the present invention may be manufactured in a manner that is itself known, e.g., by means of conventional mixing, dissolving, granulating, dragee-making, levigating, emulsifying, encapsulating, entrapping or lyophilising processes.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterise different combinations of active compound doses.

Pharmaceuticals which can be used orally include push-fit capsules made of gelatine, as well as soft, sealed capsules made of gelatine and a plasticiser, such as glycerol or sorbitol. The push-fit capsules can contain the active ingredients in admixture with filler such as lactose, binders such as starches, and/or lubricants such as talc or magnesium stearate and, optionally, stabilisers. In soft capsules, the active compounds may be dissolved or suspended in suitable liquids, such as fatty oils, liquid paraffin, or liquid polyethylene glycols. In addition, stabilisers may be added.

Dosage forms of the active compounds of the invention may also include injecting or implanting controlled releasing devices designed specifically for this purpose or other forms of implants modified to act additionally in this fashion. Controlled release of an active compound of the invention may be achieved by coating the same, for example, with hydrophobic polymers including acrylic resins, waxes, higher aliphatic alcohols, polylactic and polyglycolic acids and certain cellulose derivatives such as hydroxypropylmethyl cellulose. In addition, controlled release may be achieved by using other polymer matrices, liposomes and/or microspheres. Controlled release may also be achieved using a transdermal patch, particularly a transdermal patch in which the rate of release of one or both of the active agents is controlled by a co-polymer release membrane or in which the active agent(s) is embedded in a biodegradable matrix that dissolves at a known rate. Transdermal patches which allow slow and sustained delivery of a drug at a known rate are known in the art.

The active compounds of the present invention may also be administered to the respiratory tract as a nasal or pulmonary inhalation aerosol or solution for a nebuliser, or as a microfine powder for insufflation, alone or in combination with an inert carrier such as lactose, or with other pharmaceutically acceptable excipients. In such a case, the particles of the formulation may advantageously have diameters of less than 50 micrometers, suitably less than 10 micrometers.

In another aspect of the invention there is provided a pharmaceutical composition comprising a synergistic combination of an effective amount of a selective inhibitor of the neuronal norepinephrine transporter and an effective amount of an analgesic agent together with a pharmaceutically acceptable carrier, excipient or diluent.

In preferred embodiments, the pharmaceutical composition is formulated for intrathecal injection.

The active compounds of the invention may be administered over a period of hours, days, weeks, or months, depending on several factors, including the severity of the pain being treated, whether the pain is chronic or whether a recurrence of the pain is considered likely, etc. The administration may be constant, e.g., constant infusion over a period of hours, days, weeks, months, etc. Alternatively, the administration may be intermittent, e.g., active compounds may be administered once a day over a period of days, once an hour over a period of hours, or any other such schedule as deemed suitable.

The invention will now be described with reference to the accompanying drawings and examples, however, it is to be understood that the particularity of the following description is not to supersede the generality of the preceding description of the invention.

BRIEF DESCRIPTION OF THE DRAWINGS

FIG. 5 is a graphical representation of the mean (±SEM) anti-allodynic responses of a peptide of SEQ ID NO: 6 (0.2 nmol; 0.4 nmol (interpolated); 1 mmol), the N-type calcium channel blocker peptide of SEQ ID NO: 167 (0.18 µg/kg), administered alone or in combination, and the theoretical sum of the anti-allodynic response of these two compounds.

EXAMPLE 1

Figure 1:
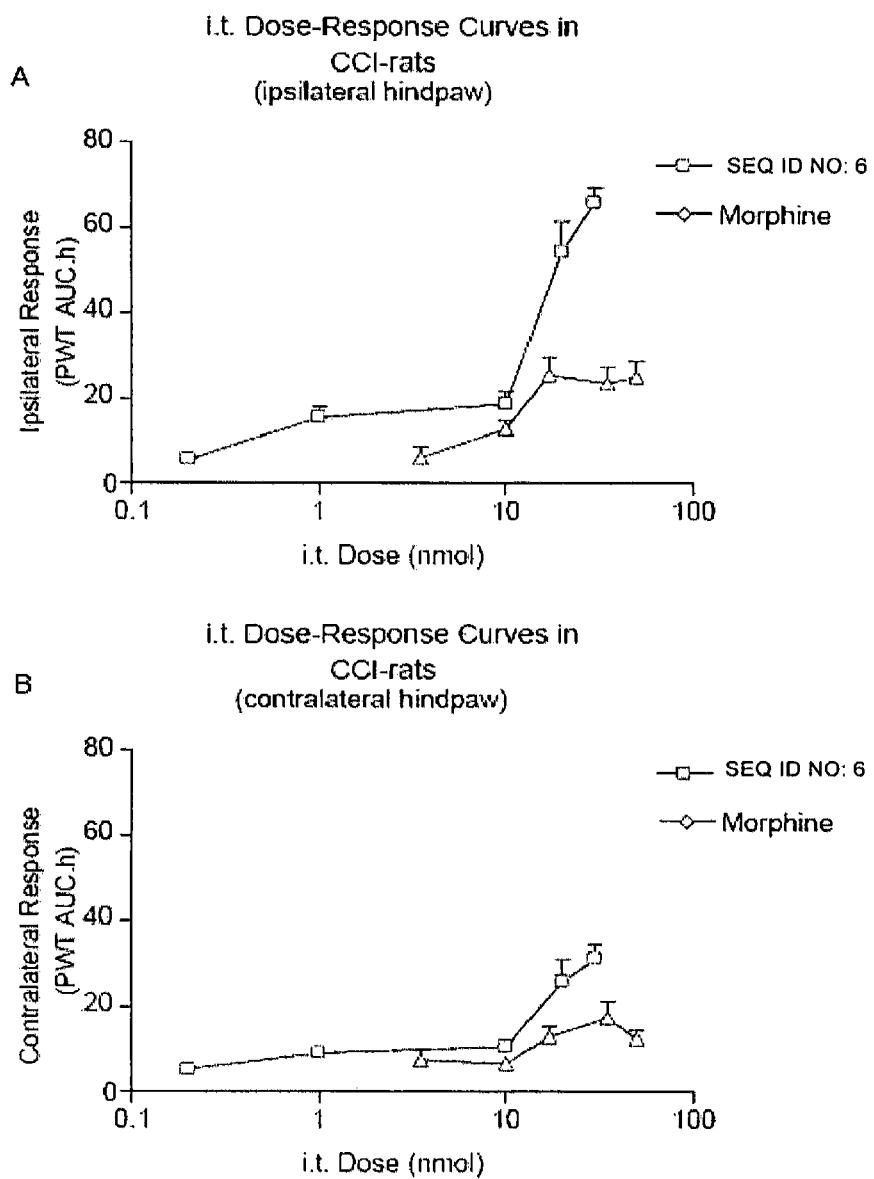
FIG. 1 is a graphical representation of the mean (±SEM) dose-response curves produced by i.t. bolus doses of a peptide of the SEQ ID NO: 6 (n=30) and morphine for the (A) ipsilateral and (B) contralateral hindpaws in CCI-rats.
Figure 2:
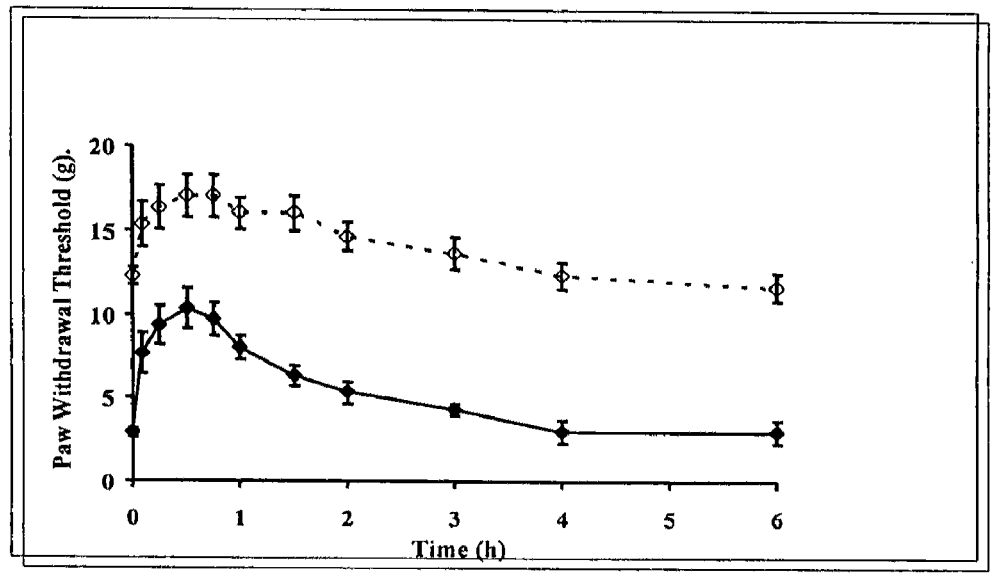
FIG. 2 is a graphical representation of (A) the mean (±SEM) paw withdrawal threshold versus time curves evoked by i.t. administration of a low dose (~$ED_{5-10}$) of a peptide of SEQ ID NO: 6 (0.2 nmol) with a low dose (~$ED_{10}$) of morphine (0.7 nmol) for the alleviation of a non-noxious stimulus of light pressure applied to the ipsilateral (-◆-) and contralateral (--◇--) hindpaws of chronic constriction injury (CCI) rats; and (B) the mean (±SEM) paw withdrawal threshold vs time curves evoked by i.t. administration of a low dose (~$ED_{10-20}$) of a peptide of SEQ ID NO: 6 (0.4 mmol) with a low dose (~$ED_{20}$) Of morphine (3.5 nmol) for the alleviation of a non-noxious stimulus of light pressure applied to the ipsilateral (-◆-) and contralateral (--◇--) hindpaws of CCI rats.
Figure 2:
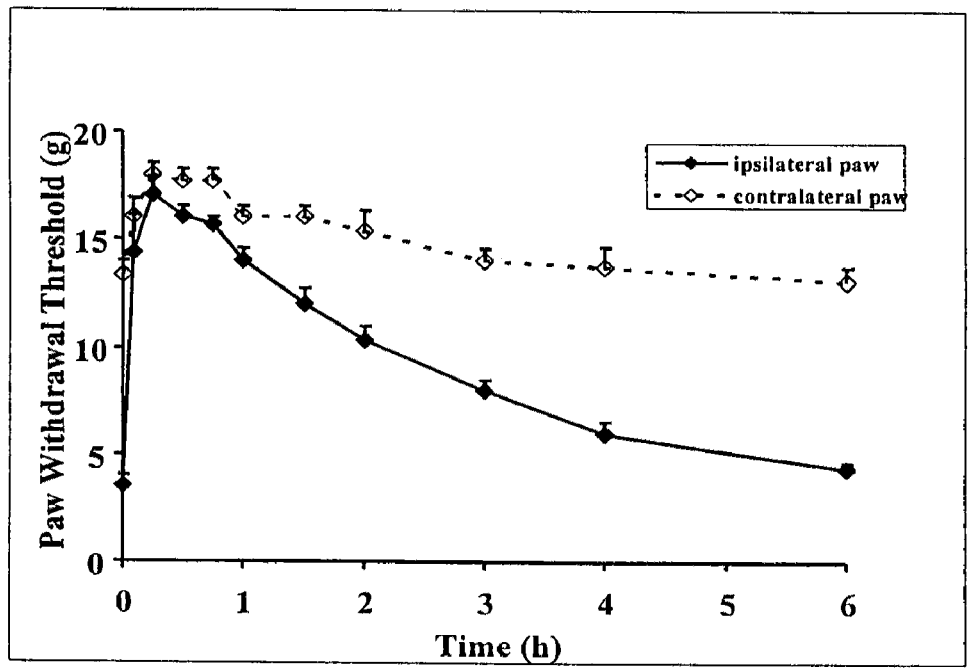
Figure 3:
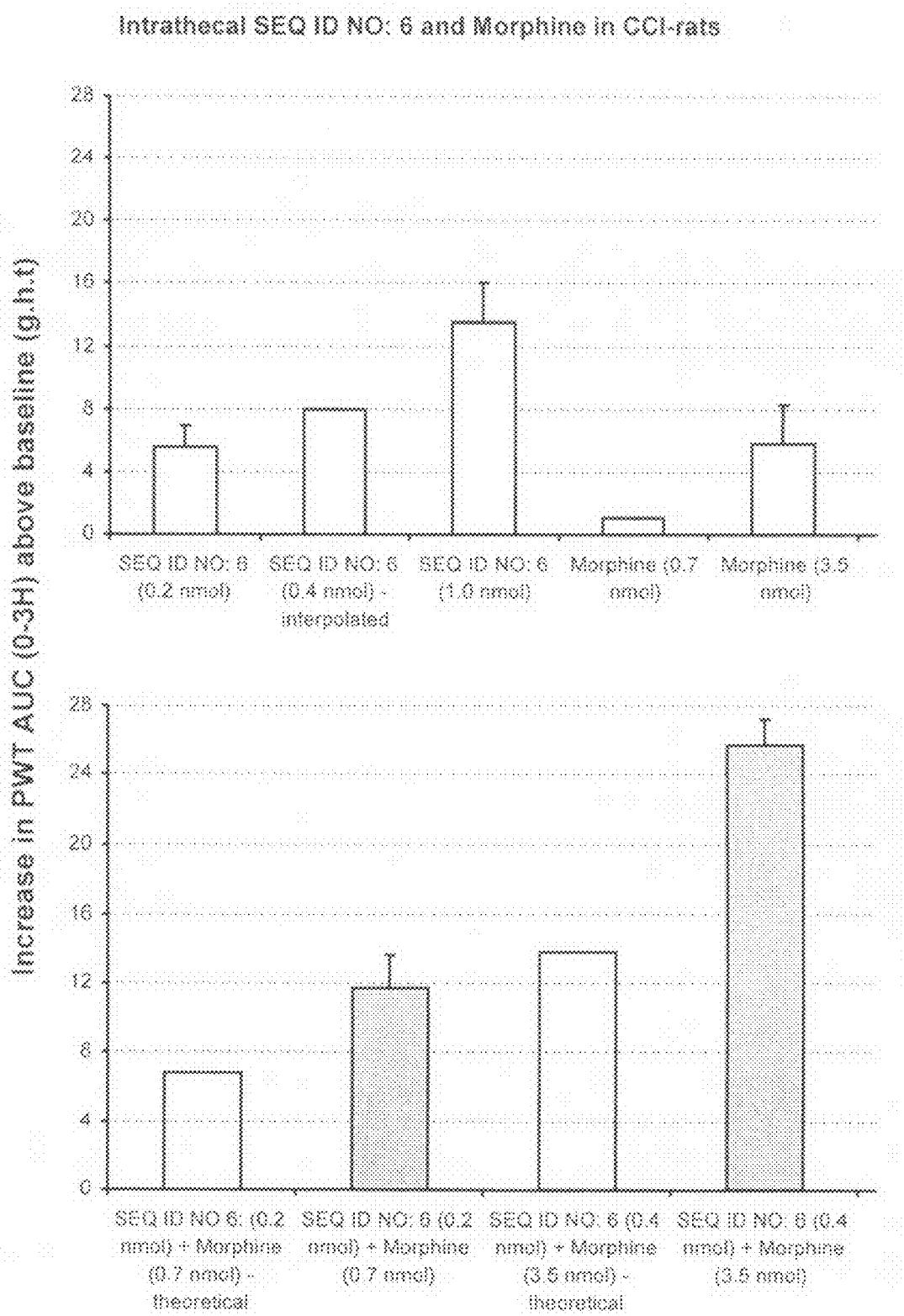
FIG. 3 is a graphical representation of the mean (±SEM) anti-allodynic responses of a peptide of SEQ ID NO: 6 (0.2 nmol, 0.4 nmol (interpolated), 1 nmol), morphine (0.7 mmol (interpolated), 3.5 nmol), each administered alone or in combination and the theoretical sum of the anti-allodynic responses of these two compounds.

Estimation of ED Values Using a Rat Model of Neuropathic Pain (a) Methods

Animals

Adult male Sprague-Dawley rats were purchased from the Herston Medical Research Centre, The University of Queensland. Rats were housed in a temperature controlled environment (21±2° C.) with a 12 h/12 h light/dark cycle. Food and water were available ad libitum. Ethical approval for this study was obtained from the Animal Experimentation Ethics Committee of The University of Queensland.

Reagents and Materials

A peptide of SEQ ID NO: 6 was synthesised using methods described previously for other chi conotoxins and chi conotoxin derivatives (WO 04/050690). The test stock solution of a peptide of SEQ ID NO: 6 (Batch #0241A; 10 mg/mL; 7.11 mM) was made up in 5 mM sodium acetate in saline, pH 5.5 and stored frozen at −20° C. Aliquots (10 µL) of the test stock solution were prepared and stored at −20° C. prior to use. Immediately prior to dosing, frozen aliquots of the test stock solution were thawed on ice and then diluted to the required concentration with vehicle (5 mM sodium acetate in saline, pH 5.5). Unused portions of thawed test stock solution were discarded upon completion of the dosing.

Morphine hydrochloride powder (B.P.) was purchased from the Royal Brisbane Hospital Pharmacy (Brisbane, Australia) and was dissolved in isotonic saline to produce desired concentration for i.t. administration (2.5 µM/mL). Sodium benzylpenicillin vials (600 mg) were purchased from CSL Ltd (Melbourne, Australia). Normal saline ampoules were obtained from Delta West Pty Ltd (Perth, Australia) and saline was purchased from Astra Pharmaceuticals Pty Ltd (Sydney, Australia). Ketamine, xylazine, enrofloxacin and bupivacaine injection vials were purchased from Provet (Brisbane, Australia). Single lumen polyethylene tubing (I.D. 0.2 mm, O.D. 0.6 mm) was purchased from Auburn Plastics and Engineering Pty Ltd (Sydney, Australia). Sterile siliconized silk sutures (Dysilk™) were obtained from Dynek Pty Ltd (Adelaide, South Australia).

Surgery

Chronic Constriction Injury (CCI) of the Sciatic Nerve

Rats were anaesthetised with ketamine (80 mg/kg) and xylazine (8 mg/kg) administered by intraperitoneal injection, and a chronic constriction injury (CCI) of the sciatic nerve was produced according to the method of Bennett and Xie (*Pain*, (1988), 33:87-107). Briefly, the left common sciatic nerve was exposed at mid-thigh level by blunt dissection through the biceps femoris. Proximal to the trifurcation, ~10 mm of nerve was freed of adhering tissue and four loose ligatures (3.0 silk) were tied around the sciatic nerve (~1 mm apart). The incision was closed in layers. After surgery, rats received benzylpenicillin (60 mg s.c.) to prevent infection and were kept warm during surgical recovery. Rats were housed singly for 14 days prior to drug or vehicle administration.

Rats were inspected daily from the time of CCI-surgery with regard to posture of the affected hindpaw, exploring behaviour, body weight and water intake, and any signs of autotomy. On rare occasions, early signs of autotomy were seen (gnawing of claw tips and some surrounding tissue on the ipsilateral hindpaw) which resulted in prompt euthanasia.

Intrathecal Catheter Insertion

Ten to eleven days post CCI-surgery, rats were deeply anaesthetised with a mixture of ketamine (80 mg kg$^{-1}$) and xylazine (8 mg kg$^{-1}$) administered as a single intraperitoneal (i.p.) injection. Prior to surgery, the back and neck regions of the rat were shaved and the skin cleansed with betadine surgical scrub. The rat was then placed in a prone position and the L6 lumbar vertebra was located by palpation of the tuber sacrales of the os ileum (Hebel & Stromberg 1976, *Anatomy of the Laboratory Rat*, Baltimore, Md.: Williams & Wilkins). A 6 cm incision was made in the midline of the back, 3 cm caudal and 3 cm cephalad to L6. A subcutaneous pocket (for the intrathecal catheter) was formed by blunt dissection with scissors on both sides of the incision. The fascia covering the superficial muscles of the back were cut in a 5 mm V-shaped incision that encompassed L5. Additional 5 mm caudal incisions were made parallel to L6. The fascia was then retracted and the lumbar muscles surrounding the base of L5 and L6 were removed, as was the m. interspinalis between the spinous processes of L5-L6.

Following removal of the L6 spinous processes with rongeurs, the soft tissue beneath the L6 iliac arch was removed, exposing the dura mater. The dural membrane was pierced with a 23G needle, releasing clear CSF. A polyethylene catheter (O.D. 0.6 mm, I.D. 0.2 mm; 20 or 50 cm length for acute and chronic experiments respectively) pre-filled with saline, was carefully advanced a distance of 1 cm into the intrathecal space and a small volume of saline (20 µL) was administered through the catheter. If leakage of saline around the catheter was observed, the rat was excluded from further experimentation. After successful completion of the "leak test", the intrathecal (i.t.) catheter was fixed with dental cement onto the surrounding muscle ~2 cm from L5, exteriorised through a subcutaneous (s.c.) tunnel to a small incision at the base of the neck and sutured in position. After suturing of the lumbar muscles and skin, rats received benzylpenicillin (50000 IU i.p.) and enrofloxacin (5 mg kg$^{-1}$ s.c.) to prevent infection and were kept warm during recovery from anaesthesia. Following completion of the surgery, rats were housed singly for a recovery period of 3-5 days prior to i.t. drug administration. On the day following surgery, the local anaesthetic, lignocaine (2%, 20 µL) was administered via the i.t. catheter. If complete paralysis of both hind legs was not observed, rats were excluded from further experimentation.

Intrathecal Drug Dosing

On day 14 post-CCI surgery, groups of rats (n=6) received a combined i.t. bolus injection of test solution and morphine in the combinations shown below, in a volume of 20 µL followed by a saline flush injection (20 µL) to ensure complete drug delivery. Anti-allodynia/antinociception was assessed using von Frey filaments (see below for details).

(i) peptide of SEQ ID NO: 6, (0.2, 1, 10, 20, 30 nmol)
(ii) morphine (3.5, 10, 17, 35, 50 nmol)

Assessment of Anti-Allodynia/Antinociception

Tactile allodynia, the distinguishing feature of neuropathic pain, was quantified using von Frey filaments. Rats were transferred to wire mesh testing cages (20 cm×20 cm×20 cm) and allowed to acclimatise for 10 minutes von Frey filaments were used to determine the lowest mechanical threshold required for a brisk paw withdrawal reflex. Briefly, starting with the von Frey filament that produced the lowest force, the filament was applied to the plantar surface of the hindpaw until the filament buckled slightly. Absence of a response after 5 seconds prompted use of the next filament of increasing weight. Filaments used produced a buckling weight of 2, 4, 6, 8, 10, 12, 14, 16, 18 and 20 g and these were calibrated regularly. A score of 20 g was given to animals that did not respond to any of the von Frey filaments. Von Frey testing was performed at the following times: predose, 5, 15, 30, 45 minutes, 1, 1.5, 2, 3, 4, and 6 hours post-dosing.

Verification of Correct i.t. Catheter Placement

At the completion of each experiment, malachite green dye (30 µL) was injected via the i.t. catheter whilst rats were lightly anaesthetised with $O_2:CO_2$ (50%:50%). Thirty seconds later, rats were decapitated and the spinal column was exposed surgically. Data from rats where there was evidence of subcutaneous dye leakage at the site where the catheter entered the back muscles above L6 or failure of the dye to distribute at least 3-4 cm along the spinal cord, were excluded from the analysis.

Data Analysis

Paw withdrawal thresholds (PWTs: g) were normalized by subtraction of the mean individual baseline PWT values quantified immediately prior to drug administration. The area under the normalized PWT versus time (PWT AUC) was calculated using the trapezoidal rule. Dose-response curves were constructed by plotting the extent and duration of the normalised ipsilateral (antiallodynic+antinociceptive) and contralateral (antinociceptive) responses (area under the normalised PWT versus time curve; PWT AUC) truncated to the first 6 h post-dosing interval, versus the i.t. dose for each of the peptide of the SEQ ID NO: 6 and morphine. $ED_{50}$ values were estimated using non-linear regression of: (i) peak PWTs versus log dose and (ii) normalised PWT AUC values versus log dose (GraphPad Prism 3.0™, San Diego, Calif.).

Statistical Analysis

The Mann-Whitney test was used to compare differences in the normalized PWT AUC values between treatment groups. Hill slopes were compared with a slope of 1.0 using the student's t-test and the significance of differences between values was determined using ANOVA followed by Dunnett's multiple comparison tests on absolute or log data, as appropriate. Statistical analysis was undertaken using the GraphPad Prism™ software package, and the statistical significance criterion was $P<0.05$.

(b) Results (i) $ED_{50}$ for SEQ ID NO: 6

A summary of the effects of the i.t. administration of a peptide of the SEQ ID NO: 6 to rats with a chronic constriction injury of the sciatic nerve (CCI-rats) is given in Table 4. A significant ($P<0.05$) dose-dependent increase in the PWT in both the ipsilateral and contralateral hindpaws was observed. Specifically, at a dose of 0.2 nmol to CCI-rats resulted in peak antiallodynic and antinociceptive effects at 15 min post-dosing and a duration of action of ~2-3 h in both the ipsilateral and contralateral hindpaws. When the i.t. dose was increased to 1 and 10 mmol, there was a rapid increase in the PWT in both the ipsilateral and contralateral hindpaws such that the peak anti-allodynic and antinociceptive effects, respectively, occurred at 1-1.5 h and the duration of action was >4 h. Increasing the magnitude of the i.t. dose further to 20 and 30 nmol again produced a rapid onset of antiallodynic and antinociceptive actions in the ipsilateral and contralateral hindpaws, respectively, such that the mean (±SEM) PWT more than doubled by 5 min post-dosing in the ipsilateral hindpaw, with the peak effect occurring at 1-1.5 h. Based on the peak responses evoked by individual doses, the mean (±SEM) $ED_{50}$ for the alleviation of tactile allodynia in the ipsilateral hindpaw was 15.7 (±3.9) nmol. The corresponding mean (±SEM) $ED_{50}$ for antinociception in the contralateral hindpaw was estimated to be 15.2 (±2.7 nmol). Interestingly, the durations of the anti-allodynic responses evoked by the 20 and 30 nmol doses were ~30 and ~54 h, >7- and 13-fold longer than that observed following administration of the 10 nmol dose. Plots of the PWT AUC versus dose for both ipsilateral and contralateral curves are provided in FIG. 1. When estimated using the PWT AUC values for the 6 h post-dosing interval, the mean (±SEM) $ED_{50}$ for the alleviation of tactile allodynia in the ipsilateral hindpaw was 14.8 (±1.1) nmol and that for the production of antinociception in the contralateral hindpaw was 14.9 (±1.1) nmol. $ED_{10}$ and $ED_{20}$ values were also estimated from this plot to be 0.2 and 0.4 nmol, respectively.

TABLE 4

Summary of results of i.t. administration of a peptide of the SEQ ID NO: 6 (0.2-30 nmol) to CCI-rats, showing a dose-related increase in a paw withdrawal threshold in both the ipsilateral (injured side) and the contralateral (non-injured side) hindpaws

| Dose - | Peak anti-allodynic effect (h) | | Δ peak PWT (g) | Duration of action (h) | | Δ PWT AUC (g · h) | |
|---|---|---|---|---|---|---|---|
| (nmol) | I* | C+ | I | I | C | I | C |
| 0.2 | 0.25 | 0.25 | 4.5 | 2-3 | 2-3 | 5.5 | 5.5 |
| 1 | 1.5 | 1.5 | 5.9 | 4 | 4 | 15.5 | 8.8 |
| 10 | 1 | 1 | 9.3 | 4 | 4 | 18.9 | 12.1 |
| 20 | 1 | 1 | 14.8 | 30 | 30 | 52.8 | 25.3 |
| 30 | 1.5 | 1 | 15.5 | 54 | 54 | 63.8 | 29.7 |

*I = ipsilateral paw,
+C = contralateral paw (ii) Morphine

Following i.t. administration of morphine to CCI-rats, there was a rapid onset of action with the peak antiallodynic and antinociceptive responses in the ipsilateral and contralateral hindpaws, respectively, occurring at 0.5-0.75 h post-dosing and a duration of action of up to 4 h (see Table 5 for summary of results). For i.t. morphine doses in the range 3.5-17 nmol, the magnitude of the anti-allodynic and the antinociceptive responses increased in a dose-dependent manner in the ipsilateral and contralateral hindpaws, respectively, similar to the responses evoked by i.t. SEQ ID NO: 6. However, further escalation of the i.t. morphine dose to 35 and 50 nmol revealed a pronounced ceiling effect such that the magnitude of the anti-allodynic and antinociceptive responses remained sub-maximal and did not increase beyond that produced by the 17 nmol dose. When estimated using the peak responses, the mean (±SEM) $ED_{50}$ doses for i.t. morphine for alleviating tactile allodynia in the ipsilateral hindpaw and for producing antinociception in the contralateral hindpaw were 7.0 (±1.7) and 10.7 (±5.1) nmol, respectively. Plots of the PWT AUC versus dose for both ipsilateral and contralateral curves are provided in FIG. 1. When estimated using the PWT AUC values, the corresponding $ED_{50}$ values were 10.2 (±1.0) and 14.3 (±1.2) nmol, respectively. $ED_{10}$ and $ED_{20}$ values were also estimated to be 0.7 and 3.5 nmol, respectively.

TABLE 5

Summary of results of i.t. administration of a peptide of the Morphine (3.5-17 nmol) to CCI-rats on (I) ipsilateral and (C) contralateral paws

| Dose - | Peak anti-allodynic effect (h) | | Δ peak PWT (g) | Duration of action (h) | | Δ PWT AUC (g · h) | |
|---|---|---|---|---|---|---|---|
| (nmol) | I* | C+ | I | I | C | I | C |
| 3.5 | 0.5 | 0.5 | 3.1 | 2-3 | 2-3 | 5.5 | 7.7 |
| 10 | .25 | .75 | 6.6 | 3-4 | 3-4 | 12.1 | 5.5 |
| 17 | .75 | .75 | 9.3 | 3-4 | 3-4 | 24.2 | 12.1 |
| 35 | As above | As above | 9.7 | As above | As above | 22 | 16.5 |
| 50 | As above | As above | 9.3 | As above | As above | 24.2 | 12.1 |

*I = ipsilateral paw,
+C = contralateral paw (iii) Vehicle and i.t. Saline

Single bolus i.t. injections of vehicle (5.5 mM sodium acetate buffer, pH 5.5) or saline did not significantly (P>0.05) alter PWTs in CCI-rats, this indicating no anti-allodynic effect in the ipsilateral hindpaw. Similarly, there was a complete absence of antinociception in the contralateral hindpaw. These results clearly indicate that neither the vehicle, saline nor the experimental procedures themselves contribute to anti-allodynic or the antinociceptive effects observed following i.t. administration of either morphine of a peptide of the SEQ ID NO: 6.

(c) Discussion

The potency of i.t. SEQ ID NO: 6 in the ipsilateral and contralateral hindpaws of CCI-rats was similar but the extent and duration (PWT AUCs) of the ipsilateral responses were ~2 fold larger than the respective contralateral responses. These findings are similar to the significantly larger thermal and/or mechanical antihyperalgesic effects of bolus doses of i.t. clonidine in L5/L6 spinal nerve-injured rats compared with the respective responses produced in non-injured animals (Paqueron et al., 2003; Poree et al., 1998). Although i.t. morphine was more potent than i.t. SEQ ID NO: 6 for the relief of tactile allodynia in CCI-rats, the duration of action of SEQ ID NO: 6 (30 nmol) was ~10-fold longer than that for a similarly large dose of i.t. morphine (35 nmol), in agreement with the observation that the duration of anti-allodynia produced by low-dose i.t. SEQ ID NO: 6 (1 nmol) was similar to that produced by a 10-fold larger dose of i.t. morphine (10 nmol). These preclinical findings suggest that i.t. SEQ ID NO: 6 may have a relatively long duration of action for the relief of moderate to severe neuropathic pain in the clinical setting.

In CCI-rats, spinal morphine produced dose-dependent anti-allodynia in a manner similar to several previous reports (see Nielsen et al., (2005) Pain 118, 112-124). However, i.t. morphine (but not i.t. SEQ ID NO: 6) also displayed a pronounced sub-maximal 'ceiling' effect for doses exceeding 17 nmol. Thus, although i.t. morphine appears to be more potent than i.t. SEQ ID NO: 6 in CCI-rats, it has a lower efficacy than i.t. SEQ ID NO: 6.

EXAMPLE 2

Figure 4:
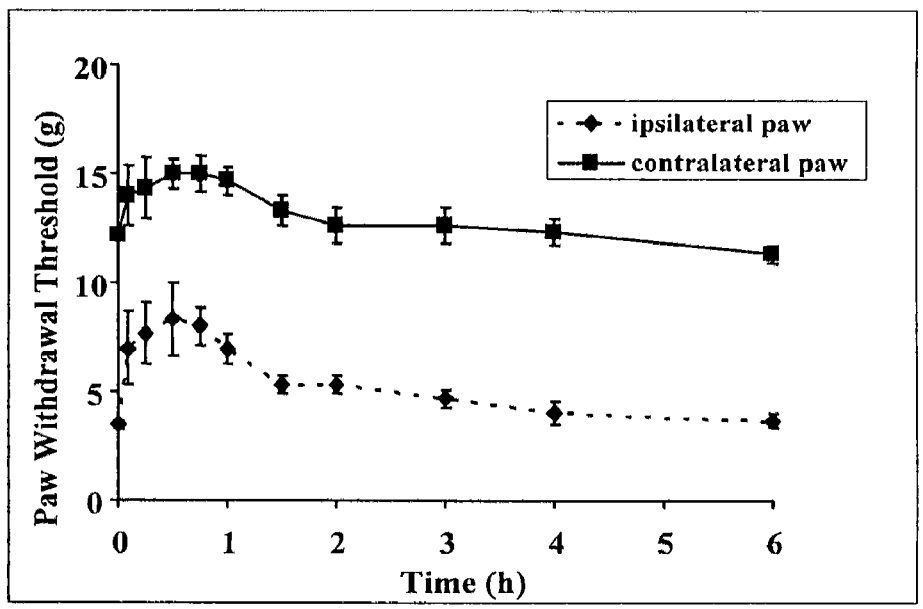
FIG. 4 is a graphical representation of (A) the mean (±SEM) paw withdrawal threshold versus time curves evoked by combined i.t. administration of a low dose (~$ED_{20}$) of a peptide of SEQ ID NO: 6 (0.4 nmol) with a low dose of (~$ED_{20}$) of the N-type calcium channel blocker peptide of SEQ ID NO: 167 (0.18 µg/kg) for the alleviation of a non-noxious stimulus of light pressure applied to the ipsilateral (-◆-) and contralateral (--◇--) hindpaws of CCI rats; and (B) the mean (±SEM) paw withdrawal threshold versus time curves evoked by i.t. administration of a low dose (~$ED_{20}$) of an N-type calcium channel blocker peptide of SEQ ID NO: 167 (0.18 µg/kg) for the alleviation of a non-noxious stimulus of light pressure applied to the ipsilateral (-◆-) and contralateral (--◇--) hindpaws of CCI rats.
Figure 4:
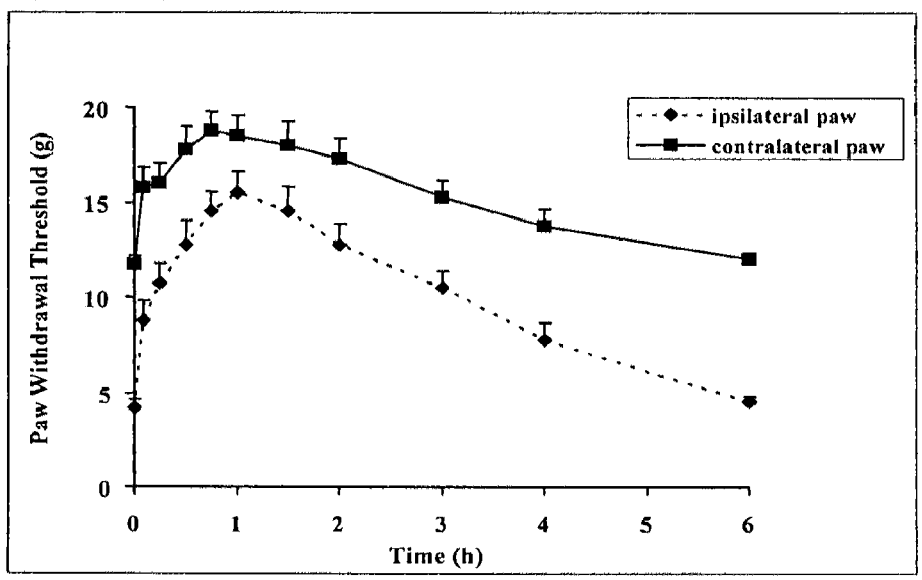

Combinations of a Chi Conotoxin Peptide with an Opioid Analgesic (a) Methods
Animals
  As in example 1.
Reagents and Materials A peptide of SEQ ID NO: 6 was synthesised using methods described previously for other chi conotoxins and chi conotoxin derivatives (WO 04/050690). The test stock solution of a peptide of SEQ ID NO: 6 (Batch #0241A; 10 mg/mL; 7.11 mM) was made up in 5 mM sodium acetate in saline, pH 5.5 and stored frozen at −20° C. Aliquots (10 μL) of the test stock solution were prepared and stored at −20° C. prior to use. Immediately prior to dosing, frozen aliquots of the test stock solution were thawed on ice and then diluted to the required concentration with vehicle (5 mM sodium acetate in saline, pH 5.5). Unused portions of thawed test stock solution were discarded upon completion of the dosing. Other reagents and material are as described in Example 1.

Surgery

Chronic Constriction Injury (CCI) of the Sciatic Nerve—As described in Example 1.

Intrathecal Catheter Insertion—As described in Example 1.

Drugs Administered

- stock solution of a peptide of SEQ ID NO: 6 (Batch #0241A; 10 mg/mL; 7.11 mM)
- morphine hydrochloride was dissolved in isotonic saline to produce the desired concentration for i.t. administration (3.5 μM/mL)
- vehicle solution (5.5 mM sodium acetate buffer in 0.9% saline, pH 5.5)

Intrathecal Drug Dosing

On day 14 post-CCI surgery, groups of rats (n=6) received a combined i.t. bolus injection of test solution and morphine in the combinations shown below, in a volume of 20 μL followed by a saline flush injection (20 μL) to ensure complete drug delivery. Anti-allodynia/antinociception was assessed using von Frey filaments (see below for details).

(i) peptide of SEQ ID NO: 6, $ED_{10}$ (0.2 mmol) and morphine, $ED_{100}$ (0.7 nmol)

(ii) peptide of SEQ ID NO: 6, $ED_{20}$ (0.4 nmol) and morphine, $ED_{20}$ (3.5 nmol)

Assessment of Anti-allodynia/Antinociception—As described in Example 1.

Verification of correct i.t. catheter placement—As described in Example 1.

Data and Statistical analysis Analysis—As described in Example 1.

(b) Results

Intrathecal Test Solution and Morphine Combination Dosing

Pre-dosing paw withdrawal in the ipsilateral hindpaw were observed to be approximately half of those in the contralateral hindpaw, consistent with the hypersensitivity that develops secondary to nerve injury in the ipsilateral side, as previously observed (FIG. 2).

Combined i.t. administration of low-dose peptide of SEQ ID NO: 6 (0.2 nmol) with low-dose morphine (0.7 nmol) produced high levels of relief of tactile allodynia (defining symptom of neuropathic pain) in the ipsilateral hindpaw of CCI-rats (n=6). The anti-allodynic effects peaked at 0.5 hours post-dosing and decreased in a mono-exponential manner; the duration of action was ~4 hours. Additionally, relatively high levels of antinociception were observed in the contralateral (non-injured) hindpaw that peaked at 0.5 hours and also returned to baseline at ~4 hours post-dosing (FIG. 2A).

Combined i.t. administration of low-dose peptide of SEQ ID NO: 6 (0.4 nmol) with low-dose morphine (3.5 nmol) produced high levels of relief of tactile allodynia (defining symptom of neuropathic pain) in the ipsilateral hindpaw of CCI-rats (n=6). The anti-allodynic effects peaked at 0.25 hours post-dosing and decreased in a mono-exponential manner; the duration of action was ~6 hours. Additionally, relatively high levels of antinociception were observed in the contralateral (non-injured) hindpaw that peaked at 0.25 hours and also returned to baseline at 6 hours post-dosing (FIG. 2B).

Statistical comparison of the anti-allodynic responses of a peptide of SEQ ID NO: 6 (0.2 nmol), morphine (3.5 nmol) and the theoretical sum of the anti-allodynic responses of these two compounds by extrapolation indicates that combined administration of a peptide of SEQ ID NO: 6 (0.2 nmol) with morphine (0.7 nmol), and a peptide of SEQ ID NO: 6 (0.4 nmol) with morphine (3.5 nmol) produce synergistic relief of tactile allodynia compared with the magnitude of the summed individual responses ($P<0.05$) (FIG. 3).

The side-effects observed following combined i.t. administration of a peptide of SEQ ID NO: 6 and morphine were similar to those observed following i.t. administration of vehicle (Na acetate buffer).

EXAMPLE 3

Co-Administration of a Chi Conotoxin Peptide with an N-Type Calcium Channel Blocker Analgesic CCI rats were treated in the same manner as for Examples 1 and 2.

Drugs Administered

- stock solution of a peptide of SEQ ID NO: 6 (Batch #0241A; 10 mg/mL; 7.11 mM)
- peptide of SEQ ID NO: 167 was dissolved in isotonic saline to produce the desired concentration for i.t. administration (13.6 μg/mL)
- vehicle solution (5.5 mM sodium acetate buffer in 0.9% saline, pH 5.5)

Intrathecal Drug Dosing

On day 14 post-CCI surgery, groups of rats (n=6) received a combined i.t. bolus injection of a peptide of SEQ ID NO: 6 and a peptide of SEQ ID NO: 167 shown below, in a volume of 20 μL followed by a saline flush injection (20 μL) to ensure complete drug delivery. Anti-allodynia/antinociception was assessed using von Frey filaments as described in Example 1.

(i) peptide of SEQ ID NO: 6, $ED_{20}$ (0.4 mmol) and peptide of SEQ ID NO: 167, $ED_{20}$ (0.18 μg/kg or 0.02 nmol)

(ii) peptide of SEQ ID NO: 167, $ED_{20}$ (0.18 μg/kg)

Results

Following i.t. administration of a peptide of SEQ ID NO: 167 (0.18 μg/kg) alone to CCI-rats, the mean (±SEM) peak levels of antinociception were relatively low occurring at 0.5 hours in each of the ipsilateral and contralateral hindpaws with a corresponding duration of action of 2-4 hours (FIG. 4A).

Combined i.t. administration of low-dose a peptide of SEQ ID NO: 6 (0.4 nmol) with a low-dose of a peptide of SEQ ID NO: 167 (0.18 μg/kg or 0.02 nmol) produced high levels of relief of tactile allodynia (defining symptom of neuropathic pain) in the ipsilateral hindpaw of CCI-rats (n=8). Similarly, high levels of antinociception were produced in the contralateral hindpaw. The mean (±SEM) levels of antinociception peaked at 1.0 hours and 0.75 hours post-dosing in each of the ipsilateral and contralateral hindpaws respectively. Antinociception decreased in a mono-exponential manner; the duration of action was ~6 hours (FIG. 4B).

Statistical comparison of the individual anti-allodynic responses of a peptide of SEQ ID NO: 6 (0.2 mmol; 0.4 mmol (interpolated); 1 mmol) and a peptide of SEQ ID NO: 167 (0.18 µg/kg) with the theoretical sum of the anti-allodynic responses of these two compounds by extrapolation indicates that combined administration of a peptide of SEQ ID NO: 6 (0.2 nmol) with a peptide of SEQ ID NO: 167 (0.18 µg/kg), appears to produce synergistic pain relief compared with the magnitude of the summed individual responses (P<0.05) (FIG. 5).

The claims defining the invention are as follows:

1. A method of producing analgesia in a subject comprising administering a synergistic combination of an effective amount of a selective inhibitor of the neuronal norepinephrine transporter and an effective amount of an analgesic agent, wherein administration of said synergistic combination produces analgesia in said subject; wherein the selective inhibitor of the neuronal norepinephrine transporter comprises the following sequence of amino acids:

(SEQ ID NO: 5)
Xaa0 Xaa1 Xaa2 Xaa3 Xaa4 Cys$_1$ Cys$_2$ Gly Tyr Lys Leu Cys$_3$ Xaa8 Xaa9 Cys$_4$, where
Xaa0 is selected from Tyr, Trp, hPhe and a deletion;
Xaa1 is a deletion;
Xaa2 is selected from Arg, Ala, Asn, Lys, Phe, BHK, Orn, DArg, Nle, DLys, DMK, DAsn, Thr, ABZ, Nap, Cit, Val, Tyr, Trp, pGlu, DpGlu, Gln, Thr, Glu, Asp and a deletion;
Xaa3 is selected from Gly, Asp, and Ala;
Xaa4 is selected from Val, Leu, Nle, Ile, and Ala;
Xaa8 is selected from His, Arg, Trp, Nal, and a deletion;
Xaa9 is selected from Hyp, Pro, Ala, Tic, Pip, MeY, DMD, Phe, THZ, Glu, Nle, Tyr, and a deletion; and
wherein Cys$_1$ is connected to Cys$_4$ and Cys$_2$ is connected to Cys$_3$ by disulfide bonds.

2. A method according to claim 1 wherein Xaa8 is Arg or His.

3. A method according to claim 1 wherein Xaa9 is Hyp or Pro.

4. A method according to claim 1 wherein Xaa2 is selected from the group consisting of pGlu, Glu, Gln, Asn and Asp.

5. A method according to claim 1 wherein Xaa4 is selected from the group consisting of Leu, Nle, Ala, Ile and Val.

6. A method according to claim 1 wherein the selective inhibitor of the neuronal norepinephrine transporter comprises the following sequence of amino acids:

(SEQ ID NO: 6)
pGlu Gly Val Cys$_1$ Cys$_2$ Gly Tyr Lys Leu Cys$_3$ His Hyp Cys$_4$ wherein Cys$_1$ is connected to Cys$_4$ and Cys$_2$ is connected to Cys$_3$ by disulfide bonds.

7. A method according to claim 1 wherein the analgesic agent is an opioid analgesic or an N-type calcium channel blocker.

8. A method according to claim 7 wherein the opioid analgesic is selected from the group consisting of propoxyphene, meperidine, hydromorphone, hydrocodone, morphine, codeine, methadone, fentanyl, sufentanil, alfentanil, oxymorphone, oxycodone, hydrocodeine, levorphanol, heroin, morphine-6-glucuronide, levallorphan, 6-monoacetylmorphine and tramodol; their pharmaceutically active salts and their optical isomers.

9. A method according to claim 1 wherein the analgesic agent is a ω-conotoxin.

10. A method according to claim 9 wherein the ω-conotoxin is selected from:

SEQ ID NO: 167

CVID: CKSKGAKCSKLMYDCCSGSCSGTVGRC

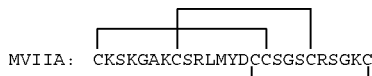

and derivatives and pharmaceutically acceptable salts thereof.

11. A method according to claim 1 wherein the effective amount of the inhibitor of the neuronal norepinephrine transporter is a sub-analgesic amount.

12. A method according to claim 1 wherein the effective amount of the analgesic agent is a sub-analgesic amount.

13. A method for the treatment or control of pain comprising administering a synergistic combination of an effective amount of a selective inhibitor of the neuronal norepinephrine transporter and an effective amount of an analgesic agent, wherein administration of said synergistic combination treats or controls pain in said subject; wherein the selective inhibitor of the neuronal norepinephrine transporter comprises the following sequence of amino acids:

(SEQ ID NO: 5)
Xaa0 Xaa1 Xaa2 Xaa3 Xaa4 Cys$_1$ Cys$_2$ Gly Tyr Lys Leu Cys$_3$ Xaa8 Xaa9 Cys$_4$ where
Xaa0 is selected from Tyr, Trp, hPhe and a deletion;
Xaa1 is a deletion;
Xaa2 is selected from Arg, Ala, Asn, Lys, Phe, BHK, Orn, DArg, Nle, DLys, DMK, DAsn, Thr, ABZ, Nap, Cit, Val, Tyr, Trp, pGlu, DpGlu, Gln, Thr, Glu, Asp and a deletion;
Xaa3 is selected from Gly, Asp, and Ala;
Xaa4 is selected from Val, Leu, Nle, Ile and Ala;
Xaa8 is selected from His, Arg, Trp, Nal and a deletion;
Xaa9 is selected from Hyp, Pro, Ala, Tic, Pip, MeY, DMD, Phe, THZ, Glu, Nle, Tyr, and a deletion; and
wherein Cys$_1$ is connected to Cys$_4$ and Cys$_2$, is connected to Cys$_3$ by disulfide bonds.

14. A method according to claim 13 wherein Xaa8 is Arg or His.

15. A method according to claim 13 wherein Xaa9 is Hyp or Pro.

16. A method according to claim 13 wherein Xaa2 is selected from the group consisting of pGlu, Glu, Gln, Asn and Asp.

17. A method according to claim 13 wherein Xaa4 is selected from the group consisting of Leu, Nle, Ala, Ile and Val.

18. A method according to claim 13 wherein the selective inhibitor of the neuronal norepinephrine transporter comprises the following sequence of amino acids:

(SEQ ID NO: 6)
pGlu Gly Val Cys$_1$ Cys$_2$ Gly Tyr Lys Leu Cys$_3$ His Hyp Cys$_4$ wherein Cys$_1$ is connected to Cys$_4$ and Cys$_2$ is connected to Cys$_3$ by disulfide bonds.

19. A method according to claim 13 wherein the analgesic agent is an opioid analgesic or an N-type calcium channel blocker.

20. A method according to claim 19 wherein the opioid analgesic is selected from the group consisting of propoxyphene, meperidine, hydromorphone, hydrocodone, morphine, codeine, methadone, fentanyl, sufentanil, alfentanil, oxymorphone, oxycodone, hydrocodeine, levorphanol, heroin, morphine-6-glucuronide, levallorphan, 6-monoacetylmorphine and tramodol; their pharmaceutically active salts and their optical isomers.

21. A method according to claim 13 wherein the analgesic agent is a ω-conotoxin.

22. A method according to claim 21 wherein the ω-conotoxin is selected from:

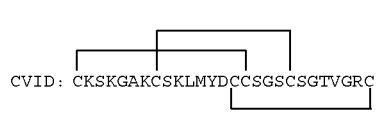

and derivatives and pharmaceutically acceptable salts thereof.

23. A method according to claim 13 wherein the effective amount of the inhibitor of the neuronal norepinephrine transporter is a sub-analgesic amount.

24. A method according to claim 13 wherein the effective amount of the analgesic agent is a sub-analgesic amount.

* * * * *